United States Patent [19]
Masubuchi et al.

[11] Patent Number: 5,460,168
[45] Date of Patent: Oct. 24, 1995

[54] ENDOSCOPE COVER ASSEMBLY AND COVER-SYSTEM ENDOSCOPE

[75] Inventors: Ryouji Masubuchi, Mizuho; Osamu Tamada, Hachioji; Yoshihiro Iida, Tama; Jin Kira, Tokyo; Hiroki Moriyama, Yokohama; Hidetoshi Saito, Hannou, all of Japan

[73] Assignee: Olympus Optical Co., Ltd., Tokyo, Japan

[21] Appl. No.: 172,643

[22] Filed: Dec. 23, 1993

[30] Foreign Application Priority Data

| Dec. 25, 1992 | [JP] | Japan | 4-347357 |
| May 11, 1993 | [JP] | Japan | 5-109503 |
| May 11, 1993 | [JP] | Japan | 5-109507 |
| May 13, 1993 | [JP] | Japan | 5-111869 |
| Aug. 3, 1993 | [JP] | Japan | 5-192580 |
| Aug. 3, 1993 | [JP] | Japan | 5-192581 |
| Aug. 23, 1993 | [JP] | Japan | 5-207483 |
| Aug. 24, 1993 | [JP] | Japan | 5-209555 |
| Aug. 25, 1993 | [JP] | Japan | 5-210611 |
| Aug. 26, 1993 | [JP] | Japan | 5-211563 |

[51] Int. Cl.$^6$ ............................................. A61B 1/00
[52] U.S. Cl. ....................... 600/123; 600/146; 600/107
[58] Field of Search ............................. 128/4, 6, 844, 128/917, 918, 919

[56] References Cited

U.S. PATENT DOCUMENTS 4,646,722  3/1987  Silverstein.

FOREIGN PATENT DOCUMENTS

| 58-44033 | 3/1983 | Japan. |
| 63-17450 | 5/1988 | Japan. |
| 64-5895 | 1/1989 | Japan. |

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

A cover-system endoscope comprises the main body of an endoscope and an endoscope cover assembly for covering the main body of the endoscope. The endoscope cover assembly includes a direction changing means such as a tube body, an erecting base having a hinge section or a balloon for erecting the erecting base in order to change the direction of a medical treatment instrument which is inserted through the medical treatment instrument channel.

12 Claims, 29 Drawing Sheets

FIG.14
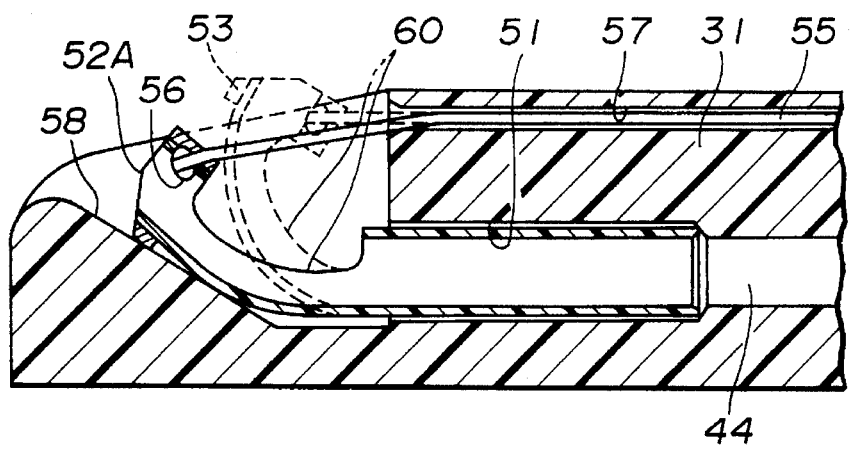
FIG.15(a)      FIG.15(b)
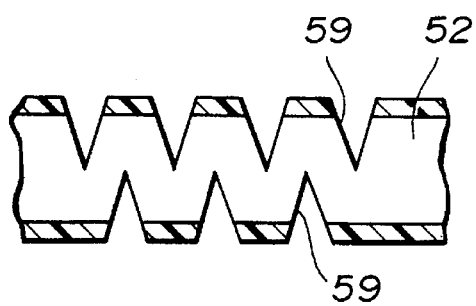    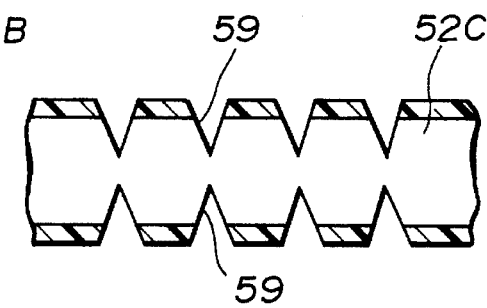
FIG.16
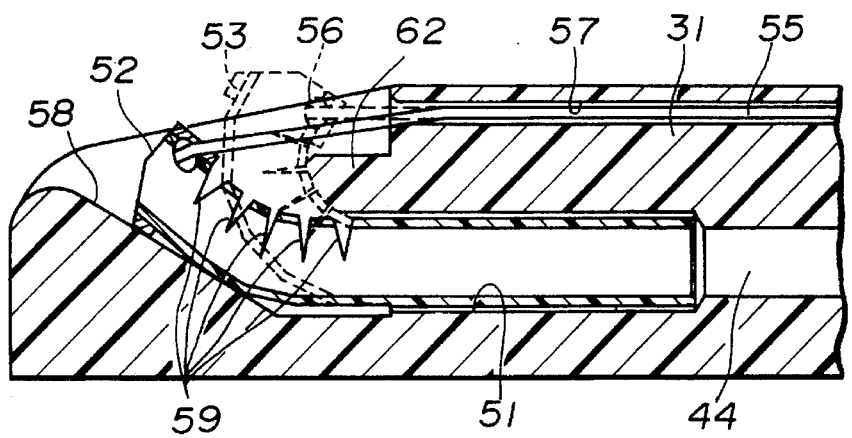

FIG.20(a)
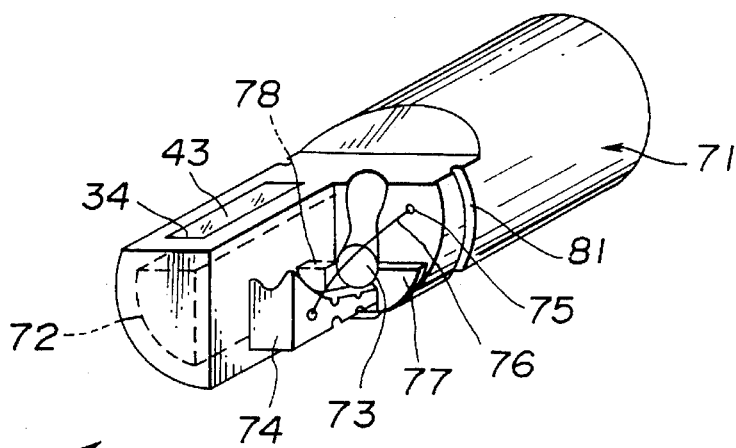
FIG.20(b)
FIG.20(c)
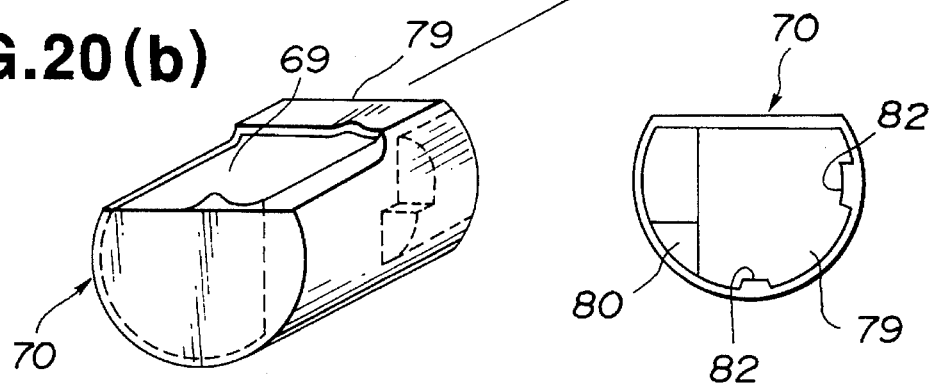
FIG.21
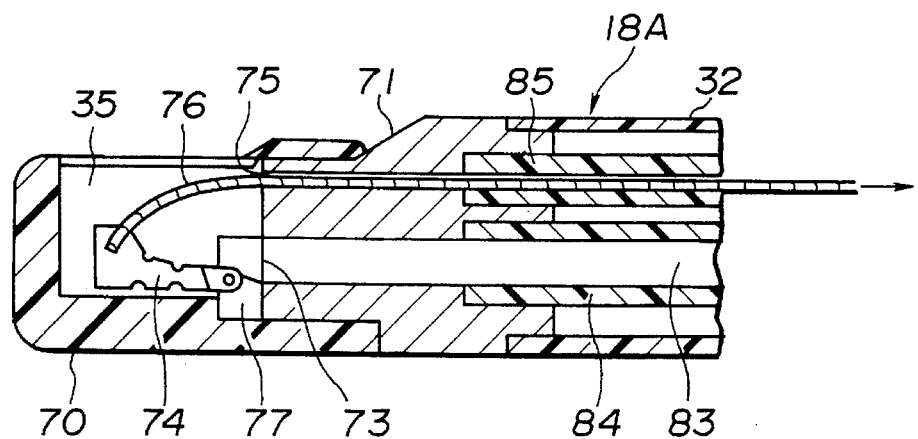

ENDOSCOPE COVER ASSEMBLY AND COVER-SYSTEM ENDOSCOPE

BACKGROUND OF THE INVENTION

1. Field of the Invention

The present invention relates to an endoscope cover assembly for covering an endoscope and a cover-system endoscope in which the endoscope is combined with the endoscope cover assembly.

2. Description of the Related Art

Recently, endoscopes have been widely used in the medical field. Because the endoscope is inserted into the human body, mucilage or dirt adheres to the insertion section of the endoscope, sometimes hindering observation or treatment. To remove the mucilage and dirt, a plurality of pipes for feeding water to the front end of the insertion section to clean the observational window, or for sucking dirt are provided in the insertion section of the endoscope.

After use on a patient in the medical field, an endoscope is cleaned or disinfected to prevent disease by infection.

Cleaning and infection procedures take a great deal of labor necessitating a relatively long time, thereby limiting the availability of endoscopes.

For this reason, so-called cover-system endoscopes have been recently used, according to which the endoscope is covered with an endoscope cover assembly which is discarded each time a treatment is completed, simplifying the cleaning and disinfection procedures after use.

U.S. Pat. No. 4,646,722 has disclosed a disposable endoscope cover assembly for covering the entire external surface of the insertion section of the endoscope when the endoscope is used, which is removed from the endoscope after use, eliminating the necessity of cleaning and disinfecting the endoscope.

Japanese Patent Laid-Open No. 2-54734 has disclosed an endoscope cover assembly for covering the external surfaces of an endoscope, which is disposable after use. Such high-efficiency cover-system endoscopes have been disclosed, which minimize the down time of the endoscope and reduce the idle time of doctors.

The above U.S. Pat. No. 4,646,722 has also disclosed a side-view type endoscope in which the endoscope cover assembly is expanded by operating an erecting mechanism provided at the front end of the insertion section of the endoscope in order to change the direction of an opening of a medical treatment instrument channel.

According to the construction described above, the endoscope cover assembly is interposed between the erecting mechanism and the medical treatment instrument to prevent contamination of the erecting mechanism.

However, the above systems have the following disadvantages. The first one concerns the durability of the endoscope cover assembly. When the medical treatment instrument is erected, the endoscope cover assembly must be expanded, thus requiring a small operating force. To achieve this purpose, it is necessary to make the endoscope cover assembly thin, but it is difficult to provide the endoscope cover assembly with sufficient strength to withstand this force. During the operation of the erecting mechanism, the endoscope cover assembly receives a local force, so that it is likely to tear. If it tears, the endoscope becomes subject to contamination so that the purpose of preventing contamination is lost.

Additionally, the endoscope cover assembly is sometimes pinched between the erecting mechanism and the endoscope front end component. In this case also, the endoscope cover assembly may be torn exposing the endoscope to contamination.

The second problem concerns the free-play allowance and assembly precision of the endoscope cover assembly which occur when the endoscope cover assembly is mounted on the aforementioned side-view type endoscope. The assembly position of the endoscope and the endoscope cover assembly may differ along the axis of the insertion section of the endoscope depending on the manufacturer of the endoscope cover assembly. Thus, in respective endoscope cover assembly products which are to be mounted in the endoscope, the erecting mechanism and the medical treatment instrument introducing channel are likely to be deviated from each other. Thus, when a clamp, which is one type of the medical treatment instruments, is erected, the erecting angle of the clamp may differ slightly depending on the kind of endoscope cover assembly product, sometimes precluding a required erecting angle. As a further problem, the erecting angle of the clamp may differ slightly. For example, a procedure for introducing the medical treatment instrument to a duodenal papilla in which the erecting mechanism is frequently used requires great precision and thus may be greatly affected by the aforementioned slight differences making it impossible to introduce the medical treatment instrument as desired.

A third problem occurs because it may be necessary to clean and disinfect the endoscope when the endoscope becomes contaminated by breakage of the endoscope cover assembly or the like. However, with the aforementioned construction, sufficiently cleaning and disinfecting the endoscope takes a great deal of labor because the construction of the endoscope is complicated and particularly because the erecting mechanism is exposed.

In addition to the constructions disclosed in U.S. Pat. No. 4,646,722, the following patent application Nos. have disclosed endoscopes which have erecting mechanisms for the medical treatment instrument.

Japanese Utility Model Laid-Open No. 63-17450 has disclosed an erecting base which is disposed parallel to the center of the field of view of an observational window with a wire for erecting the erecting base connected to a cutout provided at the erecting base. According to this construction, when the wire is pulled, the medical treatment instrument is pressed toward the center of the field of view to direct the medical treatment instrument to the center of the field of view.

According to the construction of the erecting base disclosed in Japanese Utility Model Laid-Open No. 63-17450, the wire is connected to a cutout provided on the erecting base. Thus, the wire approaches the inside face of the erecting base, that is, a face which substantially supports the medical treatment instrument. In this case, although there is no problem in protruding a medical treatment instrument having a relatively large diameter, a flexible medical treatment instrument is likely to be hooked by the wire, so that it cannot protrude to the front end of the endoscope.

If the pressing force of the wire is large, the flexible medical treatment instrument may be crushed thereby losing its function. For example, a tube injecting contrast medium which is used for imaging the pancreatic duct and bile duct is inserted from the duodenum into the duodenum mamilla, bile duct or pancreatic duct. Thus, a very flexible contrast tube may be crushed by the pressing force of the wire when the erecting base is erected, making it impossible to inject the contrast medium.

It is desirable to provide an endoscope having an erecting base which is capable of controlling the erection of the medical treatment instrument so that the medical treatment instrument is located in the center of the field of view of the observational window without being destroyed or damaged when the medical treatment instrument is erected. The same is demanded for the cover-system endoscope.

For example, Japanese Patent Laid-Open No. 64-5895 has disclosed an erecting base which is formed of an elastic material to guide the medical treatment instrument smoothly without avoiding a portion which bends sharply when the erecting base is erected.

The erecting base which is composed of the aforementioned elastic material is erected if the erecting wire connected to the erecting base is pulled; it is restored to its original position (placed down) if the erecting wire is released. However, because the aforementioned erecting base is formed of an elastic material formed of a sheet as thin as 0.03 mm–0.5 mm, it is twisted when the erecting wire is pulled, so that the direction of the protrusion of the medical treatment instrument may not be stabilized. Due to the twisting, sometimes the medical treatment instrument is not protruded properly, and thus this erecting base has room for improvement.

The following problems exist concerning the medical treatment instrument which will be erected by the erecting mechanism.

There are a variety of medical treatment instruments available including a flexible one like the aforementioned contrast medium tube made of resin and another requiring a large force when it is bent like a basket clamp for destroying calculus. Depending on the type of medical treatment instrument, the force required for erecting the instrument varies.

Of the aforementioned cover-system endoscopes, for example, a type employing a side-view type endoscope is suitable for treatment inspecting the bile duct system through duodenum Vater's mamilla. In most cases, the treatment uses flexible instruments and consists of imaging the bile duct, cutting off the mamilla and the like. A basket clamp or the like which requires a large erecting force is seldom used.

Depending on the object and purpose of observation, different medical treatment instruments are used. In erecting mechanisms which erect an instrument with a uniform driving force, it is difficult to adjust the mechanism so that the instrument is erected by a suitable force. Moreover, a high-level skill is required.

Further, the cover-system endoscope has the following problems as well as those described above.

Generally, a reusable type endoscope is used several hundred times by cleaning and disinfecting it after each use. That is, such endoscopes are rigidly constructed so as to withstand several hundred treatments, making them expensive. Even if the initial cost of the medical treatment instrument is increased to some extent, the overall cost for operating the endoscope system is not greatly affected.

On the other hand, if the same structure as the medical treatment instrument guiding device of the reusable type endoscope is provided on the endoscope cover assembly, the cost of the endoscope cover assembly increases.

The cost of the endoscope cover assembly in the cover-system endoscope must be reduced because the endoscope cover assembly is disposed of and replaced each time a treatment is finished. Thus, it is desirable that used parts be as inexpensive as possible.

Next, the construction for erecting the aforementioned erecting mechanism will be described below. An erecting mechanism disclosed in Japanese Utility Model Laid-Open No. 63-17450 is erected by pulling an erecting wire for which an operating member needs to be provided on the operator's side. It is desirable for the aforementioned operating member to be easily operable. Because the endoscope cover assembly is detachable from the endoscope, it is important that the aforementioned operating member not be an obstacle in detaching or attaching it.

Further, because operations for curving the endoscope sometimes must be performed while the erecting mechanism is operated, if it takes a great deal of labor to perform both operations, a medical treatment may take a long time and in some cases, the treatment may be insufficient. This is the reason that a cover-system endoscope which facilitates operating the aforementioned erecting mechanism and curving the endoscope is demanded.

In addition to those described above, the following problems can be addressed. That is, because, according to the cover-system endoscope, the endoscope is covered with the endoscope cover assembly, the endoscope is painful to patients when the diameter of the insertion section covered with the endoscope cover assembly increases. Thus, it is desirable to reduce the diameter of the insertion section while maintaining the erecting function. The reduction of the diameter leads to a reduction of the required inspection time. It is also necessary for the insertion section to be inserted smoothly with the endoscope cover assembled with the endoscope cover assembly.

If a gap is caused between the observational window/illumination window of the endoscope and the transparent cover of the endoscope cover assembly when the endoscope is inserted and mounted in the endoscope cover assembly, the following problem is generated. That is, part of the illumination light transmitted from the illumination window of the endoscope is reflected by the inside face of the transparent cover and the reflected light enters the observational window, thereby causing a flaring reflection in observed images.

SUMMARY OF THE INVENTION

The first object of the present invention is to provide an endoscope cover assembly which is capable of changing the direction of the protrusion of a medical treatment instrument to a predetermined position and which has sufficient strength.

The second object of the present invention is to provide an endoscope cover assembly which is capable of changing the direction of the protrusion of a medical treatment instrument to a predetermined position without greatly deviating the erecting angle of the medical treatment instrument largely depending on the kind of endoscope cover assembly.

The third object of the present invention is to provide an endoscope cover assembly in which the construction for changing the direction of a medical treatment instrument is relatively simplified to reduce the cost of manufacturing.

The fourth object of the present invention is to provide a cover-system endoscope which is capable of changing the direction of the protrusion of a medical treatment instrument to a predetermined position and which has an endoscope cover assembly which is not likely to be damaged when the direction of the protrusion of the medical treatment instrument is changed.

The fifth object of the present invention is to provide a cover-system endoscope which is capable of precisely changing the direction of the protrusion of a medical treatment instrument.

The sixth object of the present invention is to provide a cover-system endoscope which is capable of changing the direction of the protrusion of a medical treatment instrument to a predetermined position without greatly deviating the erecting angle of the medical treatment instrument depending on the kind of endoscope cover assembly.

The seventh object of the present invention is to provide a cover-system endoscope which has a construction capable of changing the direction of a medical treatment instrument, the construction largely precluding twisting of the medical treatment instrument when the direction of the medical treatment instrument is changed and being capable of protruding the medical treatment instrument to a desired direction securely.

The eighth object of the present invention is to provide a cover-system endoscope in which the medical treatment instrument is not crushed when the direction of the erection of the medical treatment instrument is changed even if the instrument is flexible.

The ninth object of the present invention is to provide a cover-system endoscope which is constructed so that the shape of the insertion section is simple, thereby minimizing the labor required for cleaning and disinfection even if the endoscope cover assembly is damaged.

The tenth object of the present invention is to provide a cover-system endoscope which is capable of changing the direction of the protrusion of the medical treatment instrument so as to guide it to the field of view of the endoscope so that it can be observed.

The eleventh object of the present invention is to provide a cover-system endoscope in which the construction for changing the direction of a medical treatment instrument is relatively simplified to reduce the manufacturing cost.

The twelfth object of the present invention is to provide a cover-system endoscope in which the construction for changing the direction of the protrusion of the medical treatment instrument is selectable corresponding to differences of the driving force required for changing the direction of the protrusion of the medical treatment depending on respective medical treatment instruments so as to obtain a desired erecting angle, the cover-system endoscope not being likely to damage or crush the medical treatment instrument.

The thirteenth object of the present invention is to provide a cover-system endoscope in which a means for changing the direction of a medical treatment is easy to handle and highly operable.

The fourteenth object of the present invention is to provide a cover-system endoscope in which the means for changing the direction of the medical treatment instrument is not an obstacle in attaching or detaching the endoscope cover assembly to/from the endoscope.

The fifteenth object of the present invention is to provide a cover-system endoscope in which when operations for changing the direction of the medical treatment instrument and for curving the endoscope are performed alternately, it is possible to switch those operations easily, securing a high operability.

The sixteenth object of the present invention is provide a cover-system endoscope which has a function for changing the direction of a medical treatment instrument and in which the diameter of the insertion section can be reduced as much as possible even when an endoscope cover assembly is mounted thereon.

The seventeenth object of the present invention is to provide a cover-system endoscope which can be inserted easily when an endoscope cover assembly is mounted on the endoscope.

The eighteenth object of the present invention is to provide a cover-system endoscope which has a function for changing the direction of the medical treatment instrument and a simple construction for preventing a flaring reflection due to the entering of illumination light into an observational optical system.

According to a preferred embodiment of the present invention, the cover-system endoscope comprises the main body of an endoscope containing an insertion section and an operating unit and an endoscope cover assembly which covers at least the insertion section of the main body of the endoscope and contains a medical treatment instrument channel through which a medical treatment instrument is inserted, the endoscope cover assembly containing a direction changing means for changing the direction of a medical treatment instrument which is introduced through the medical treatment instrument channel and then protruded from the medical treatment instrument channel opening.

The other features and advantages of the present invention will be made evident in a detailed description below.

BRIEF DESCRIPTION OF THE DRAWINGS

FIG. 14 is a sectional view showing the construction of the front end of the insertion section covering portion of the third embodiment.

FIGS. 15(a) and 15(b) is an explanatory drawings showing the construction of the erecting tube related to the fourth embodiment.

FIG. 16 is a sectional view showing the construction of the front end of the insertion section covering portion of the fifth embodiment.

FIGS. 20(a), 20(b) and 20(c) are is a perspective views showing the construction of the front end cover component.

FIG. 21 is a side sectional view showing the front end of the insertion section covering portion.

FIG. 26 is a top view of the erecting base.

FIG. 27 is a side view of the erecting base.

FIG. 31 is a top view of the cover showing the erecting action of the erecting tube.

FIG. 32 is a side view showing the movement of the erecting tube.

FIG. 45(a) is a view showing the construction of the erection control unit; and FIG. 45(b) is a view showing the construction of a curving mechanism.

FIGS. 46(a) and 45(b) are related to the fifteenth embodiment; FIG. 46(a) is a top view of the erection control unit.

FIG. 47(a) is a top view of the erection control unit; and FIG. 47(b) is a side view of (a).

FIG. 56 is a longitudinal sectional view showing the construction of the front end of the insertion section covering portion.

FIG. 57 is a longitudinal sectional view showing the insertion section covering portion fit to the endoscope.

DETAILED DESCRIPTION OF THE PREFERRED EMBODIMENTS

The first embodiment of the present invention will be described with reference to the accompanying drawings 1–7.

Figure 1:
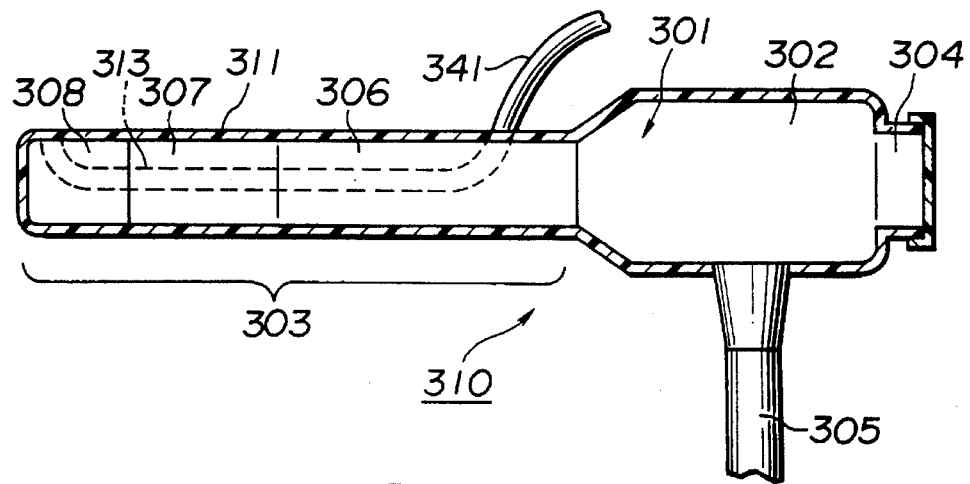
FIG. 1 is a schematic drawing of the cover-system endoscope related to the first embodiment of the present invention.

FIG. 1 shows a schematic construction of a cover-system endoscope 310. The cover-system endoscope 310 comprises a side view type endoscope 301, and an endoscope cover assembly 311 for covering the endoscope 301 and which is disposable. The endoscope 301 is connected to an operating unit 2 on the operator's side, for example, an insertion section which is to be inserted into a human body and an eye-piece portion which enables visual observation of the internal structure of the human body. In the endoscope 301, a universal cord 305 which is to be connected to a light source (not shown) extends from the side of the operating unit 302.

The insertion section 303 comprises a long flexible tube 306 which extends from the operating unit 302, a curve portion 307 which may be curved, and a side view type front end component 308 which are connected to each other successively.

The operating unit 302, the insertion section 303 and the eye-piece portion, of the endoscope 301 are covered with the endoscope cover assembly 311.

Figure 2:
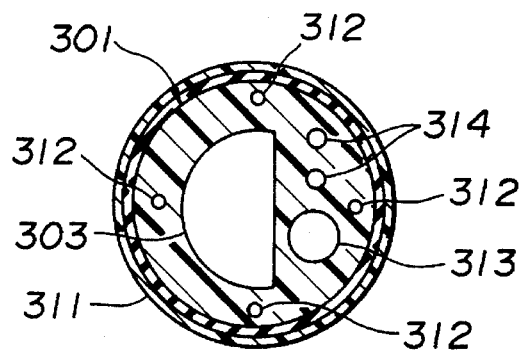
FIG. 2 is a sectional view showing the internal construction of the endoscope insertion section on which a cover is mounted.

FIG. 2 is a sectional view of the insertion section 303 which is covered with the endoscope cover assembly 311. Inside the insertion section 303, four operating wires 312 for operating the curve portion 307 to be curved, a medical treatment instrument introducing channel 313, and an air/water feeding channel 314 are disposed. Medical treatment instruments, including a clamp, a myzesis instrument, a cautery knife, an electrode knife, ultrasonic probe and a catheter, are inserted into the medical treatment instrument introducing channel 313. The medical treatment instruments for use are not restricted to the aforementioned instruments.

Figure 3:
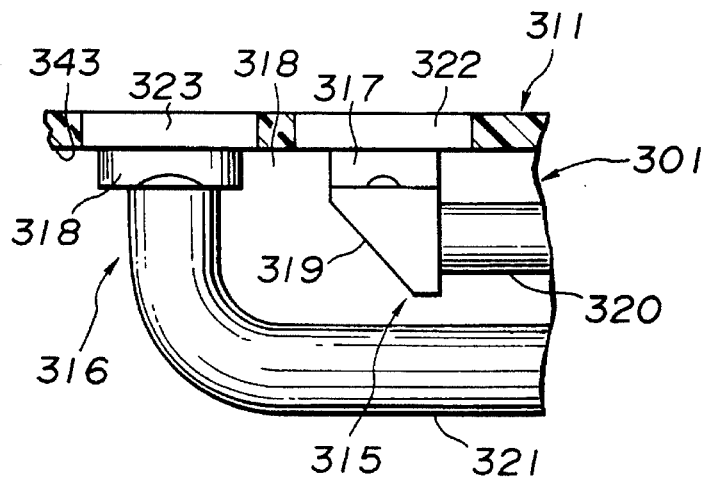
FIG. 3 is a longitudinal sectional view containing the object optical system of the endoscope cover assembly in which the endoscope is inserted.

FIG. 3 illustrates an object optical system 315 and an illuminating optical system which are disposed in the front end component 308 of the endoscope 301. An essentially flat surface 343 is formed on the circumference of the front end component of the endoscope so as to face the field of view. An observational objective lens 317 of the object optical system and an illumination lens 318 of the illuminating optical system 316 are disposed on this surface 343 so that they are water-tight.

Inside the objective lens 317, an end of an image guide fiber 320 is disposed so as to face the objective lens 317 via a prism, and inside the illumination lens 318 an end of a light guide fiber 321 is disposed so as to face the illumination lens 318.

On the endoscope cover assembly 311, an observational cover lens 322 and an illumination single-fiber lens 323 are disposed so as to face the objective lens 317 and the illumination lens 318 respectively when the endoscope cover assembly 311 is fit to the endoscope 301. The diameter of the observational cover lens 322 is larger than that of the objective lens 317. When the endoscope cover assembly 311 is fit to the endoscope 301, the observational objective lens 317 and the observational cover lens having a larger diameter than that of the observational objective lens are disposed so that they face each other, and further, the illumination lens 318 and the illumination single-fiber lens 323 are also disposed so that they face each other. Because the diameter of the observational cover lens 322 is larger than that of the objective lens 317, the field of view of the objective lens 317 is not disturbed by the endoscope cover assembly 311. As regards the illuminating optical system 316, because the single-fiber lens 323 is disposed in the endoscope cover assembly 311, it is possible to prevent illumination light from leaking to the object optical system 315 through the endoscope cover assembly 311.

Figure 4:
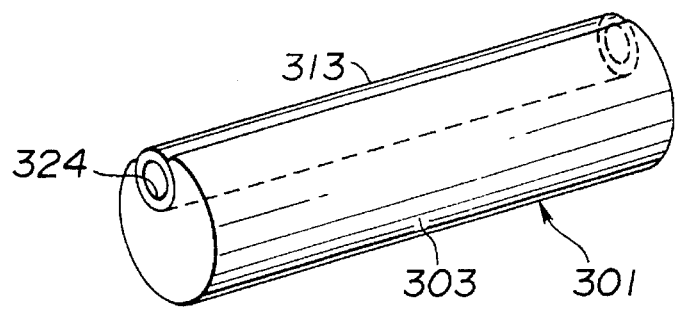
FIG. 4 is a perspective view showing a medical treatment instrument introducing-channel-mounting-groove which is formed in the insertion section of the endoscope.

As shown in FIG. 4, in the external surface of the insertion section 303, a mounting groove 324 for the medical treatment instrument introducing channel 313 is formed essentially linearly along the axis of the insertion section 303. The endoscope cover assembly 311 is fit so that the medical treatment instrument introducing channel 313 is embedded within the mounting groove 324. Thus, when the endoscope cover assembly 311 is fit to the endoscope, the medical treatment instrument introducing channel 313 is fixed in the insertion section 303, thereby preventing the medical treatment instrument introducing channel 313 from sliding along the circumference.

A beginning end of the medical treatment instrument introducing channel 313 on the operator's side extends out near the portion in which the insertion section 303 of the endoscope 301 is combined with the operating unit 302. The portion of the medical treatment instrument introducing channel 313 which extends out at the beginning end acts as an introducing portion 341 which is used for introducing a medical treatment instrument, such as a clamp.

Figure 5:
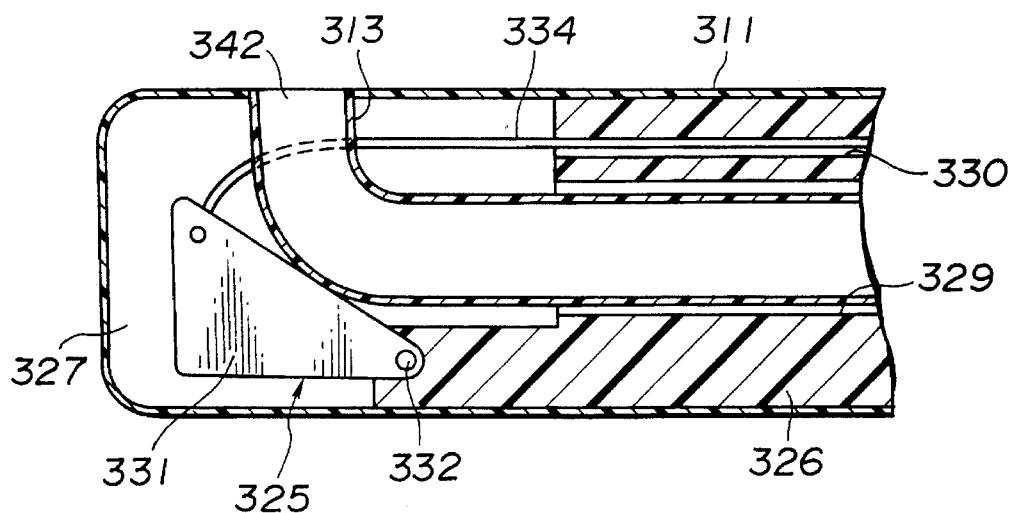
FIG. 5 is a longitudinal sectional view showing an erecting mechanism of the endoscope cover assembly.

As shown in FIG. 5, the medical treatment instrument introducing channel 313 is formed integratedly with the endoscope cover assembly 311. The endoscope cover assembly 311 also contains an erecting device 325 which is a direction changing means for erecting a medical treatment instrument introduced into the medical treatment instrument introducing channel 313 in the direction of the field of view of the main body of the endoscope 301. In the front end of the endoscope cover assembly 311, a holding member 326 which holds the front end component 308 of the endoscope 301 is disposed in front of the curve portion 307 and an air tight chamber 327 is formed in front of the holding member 326.

Figure 6:
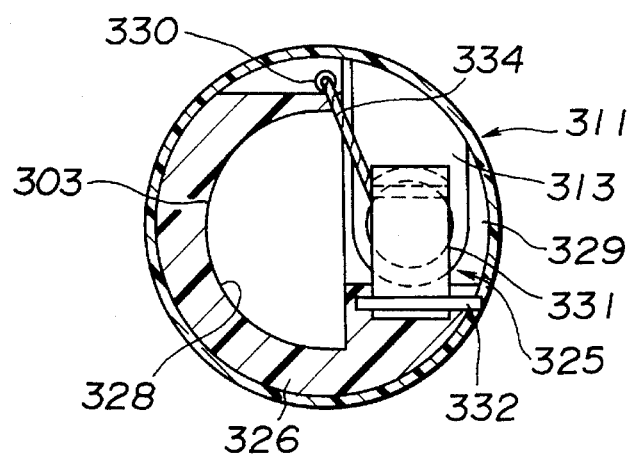
FIG. 6 is a cross sectional view showing the erecting mechanism of the endoscope cover assembly.

As shown in FIG. 6, a guide pipe 328, a guide pipe 329 for the medical treatment instrument introducing channel 313, and a wire guide pipe 330 are formed in the holding member 326. Further, an end of the erecting base 331 which is formed in the shape of an essentially triangular column is rotatably supported in front of the guide pipe 329 for the medical treatment instrument introducing channel 313. An end of the medical treatment instrument channel 313 inserted through the guide pipe 329 is curved within the air tight chamber 327 and connected to the main body of the endoscope cover assembly 311.

The insertion section 303 of the endoscope is inserted into the guide pipe 328 for the endoscope. The guide pipe 328 is formed so that the cross section of at least its end is a semicircle as shown in FIG. 6. Because the medical treatment instrument introducing channel 313 is connected to the main body of the endoscope cover assembly 311 only at a channel opening 342, the medical treatment instrument introducing channel 328 is capable of moving freely within a limited range of the inside of the endoscope cover assembly.

Figure 7A:
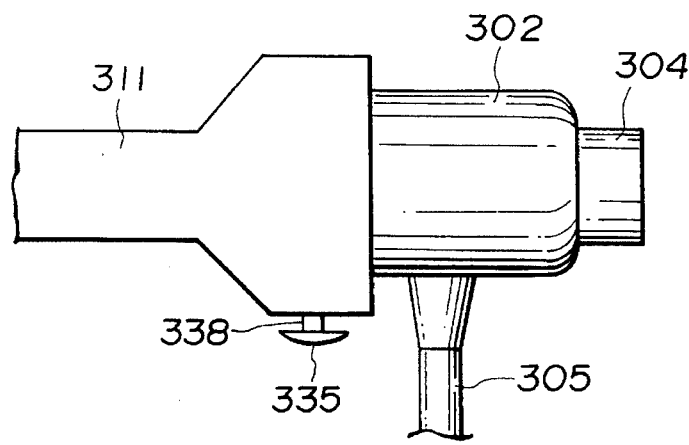
FIG. 7(a) is a side view showing the mounting condition of an erecting base operating knob.

The erecting device 325 is structured so that the erecting base 331 can move in a circle relative to the rotating shaft 332 which is supported by the erecting base 331. An end of an erecting wire 334 is fastened to the other end of the erecting base 331. As shown in FIG. 7(a), a beginning end of the erecting wire 334 is connected to an erecting base operating knob 335 which is disposed near the operating unit on the operator's side of the endoscope cover assembly 311. The erecting base 331 is erected almost along the axis of the insertion section when the erecting wire 334 is pulled.

When placing the endoscope cover assembly 311, first of all, the erecting wire 334 is inserted through the guide pipe 330 of the holding member 326, and second, the medical treatment instrument introducing channel 313 is inserted through the guide pipe 329 of the holding member 326. Subsequently, the holding member 326 and the erecting device 325 are covered with the main body of the endoscope cover assembly 311 and then the erecting wire 334 can be connected to the erecting base operating knob 335.

Figure 7B:
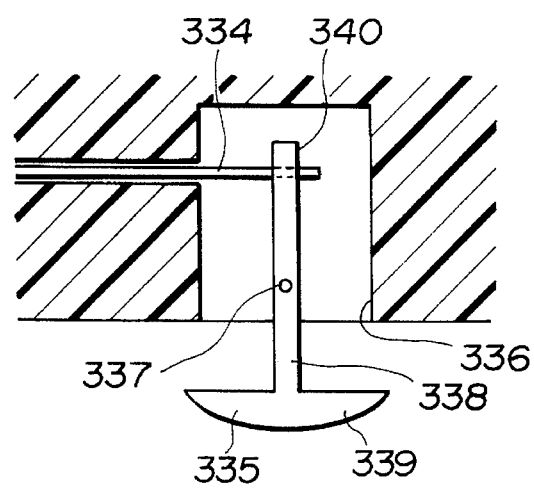
FIG. 7(b) is a longitudinal sectional view showing the internal construction of the erecting base operating knob.

FIGS. 7(b), (c) are sectional views showing essentially the construction of the erecting base operating knob 335. As shown in the sectional view of FIG. 7(b), a mounting hole 336 for the erecting base operating knob 335 is formed on the operator's side of the endoscope cover assembly 311. In the mounting hole 336, a rotating lever 338 is rotatably supported with respect to a fixed pin 337. An end of the rotating lever 338 protrudes out of the mounting hole 336, acting as a knob head 339 of the operating knob 335.

Figure 7C:
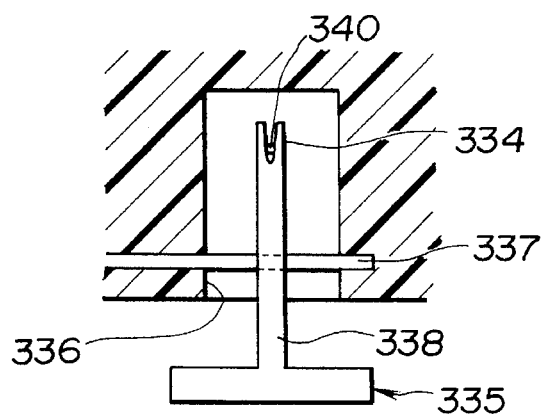
FIG. 7(c) is a cross sectional view showing the internal construction of the erecting base operating knob.

On the other end of the rotating lever 338, an essentially slotted wire locking portion 340 is provided as shown in the cross sectional view of FIG. 7(c). The locking portion 340 of the rotating lever 338 locks the beginning end of the erecting wire 334.

When locking the erecting wire 334 onto the locking portion, it is permissible to lock the erecting wire 334 onto the locking portion 340 of the rotating lever 338 outside of the endoscope cover assembly before the knob 335 is fastened to the mounting hole 336 of the endoscope cover assembly 311. It is also permissible that, with the knob 335 fastened within the mounting hole 336 of the endoscope cover assembly 311, the erecting wire 334 is secured by a relatively longer length for the end of the erecting wire 334 on the operator's side so as to protrude out of the endoscope cover assembly 311, and then the wire 334 is locked onto the locking portion 340 of the rotating lever 338 by handling the erecting wire 334 from outside of the endoscope cover assembly 311.

The locking portion 340 of the rotating lever 338 is not restricted to the slot type as shown in FIG. 7(c) and it is permissible to provide such a structure to elastically lock the wire 334 onto the rotating lever 338 by means of a grip or the like.

Meanwhile, the locking structure described above may be applied to the portion in which the erecting base 331 is to be connected to the erecting wire 334. In this case, it is permissible to fix the erecting wire 334 to the knob 335 by soldering before the knob 335 is fastened to the endoscope cover assembly 311, insert the erecting wire 334 from an opening on the operator's side of the guide pipe 330 of the endoscope cover assembly 311 to make the erecting wire 334 protrude out of the opening on the front end, and then lock the erecting wire 334 onto the erecting base 331.

Next, the operation of the construction described above will be described. When a side view type endoscope 301 is used, as shown in FIG. 1, the endoscope cover assembly 311 is mounted so as to cover the insertion section 303 and the operating unit 302 of the endoscope 301. With this state, the insertion section 303 of the endoscope 301 is inserted into a body cavity of a patient.

A medical treatment instrument, such as a clamp, is inserted from the medical treatment instrument introducing portion 341 at the beginning end of the medical treatment instrument introducing channel 313, introduced through the medical treatment instrument introducing channel 313 up to the front end of the insertion section 303 of the endoscope 301, and then protruded out of the endoscope 301 through the channel opening 342.

When the direction of the front end of a medical treatment instrument, such as a clamp, which protrudes out of the endoscope 301 is adjusted, the erecting base operating knob 335 is operated. Interlocked with the operation of the erecting base operating knob 335, the erecting wire 334 is pulled or pushed so that the angle of the erecting base 331 is changed to a desired angle corresponding to the movement of the erecting base wire 334.

Further, the medical treatment instrument introducing channel 313 which is interlocked with the rotation of the erecting base 331 is pushed by means of the erecting base 331 so that the direction of the channel opening 342 (opening angle) of the medical treatment instrument introducing channel 313 is changed, thereby changing the erecting angle of a medical treatment instrument which is inserted through the medical treatment instrument introducing channel 313.

According to the present embodiment, the medical treatment instrument introducing channel 313 and the erecting base 331 which erects a medical treatment instrument introduced through the channel 313 in the direction of the field of view of the main body of the endoscope 301 are provided on the endoscope cover assembly. Thus, it is possible to suppress a dispersion of the erecting angle of a medical treatment instrument which may be caused due to a combination of the endoscope 301 and the endoscope cover assembly 311. In the present embodiment, because the erecting device 325 is provided in the endoscope cover assembly 311, a medical treatment instrument is erected with the cover interposed, and therefore it is not necessary to take special measures to thin the cover. Thus, in the present embodiment, it is possible to form a solid cover.

Additionally, it is not necessary to provide the endoscope with the erecting device 325 for erecting a medical treatment instrument in the direction of the field of view of the main body of the endoscope 301. Thus, it is possible to simplify the construction of the insertion section 303 of the endoscope 301, and further, if the endoscope cover assembly 311 is broken so that the endoscope is stained, it is easy to clean and disinfect the endoscope 301.

Further, because the erecting base operating knob 335 is disposed on the endoscope cover assembly 311 and is disposable, no cover which covers the erecting base operating knob 335 is required. Thus, the erecting base operating knob 335 can be operated directly, thereby facilitating precision operations which are required for, for example, cannulation. Also, it is not necessary to attach and detach a cover for covering the erecting base operating knob 335, thereby simplifying the construction of the erecting base operating knob 335.

Although the present embodiment provides a construction that the guide pipe 329 for the medical treatment instrument introducing channel 313 is formed in the holding member 326 within the endoscope cover assembly 311, and the medical treatment instrument introducing channel 313 is inserted through the guide pipe 329, other constructions which will be described below are also permissible.

According to the present embodiment, most of the medical treatment instrument introducing channel 313 is formed by the guide pipe 329 of the holding member 326. Further, it is permissible to form a tube which extends from the portion where the channel opening 342 is connected to the main body of the endoscope cover assembly 311 up to the opening on the front end of the guide pipe 329, so that this tube may be substituted for the movable portion of the medical treatment instrument introducing channel 313.

Figure 8:
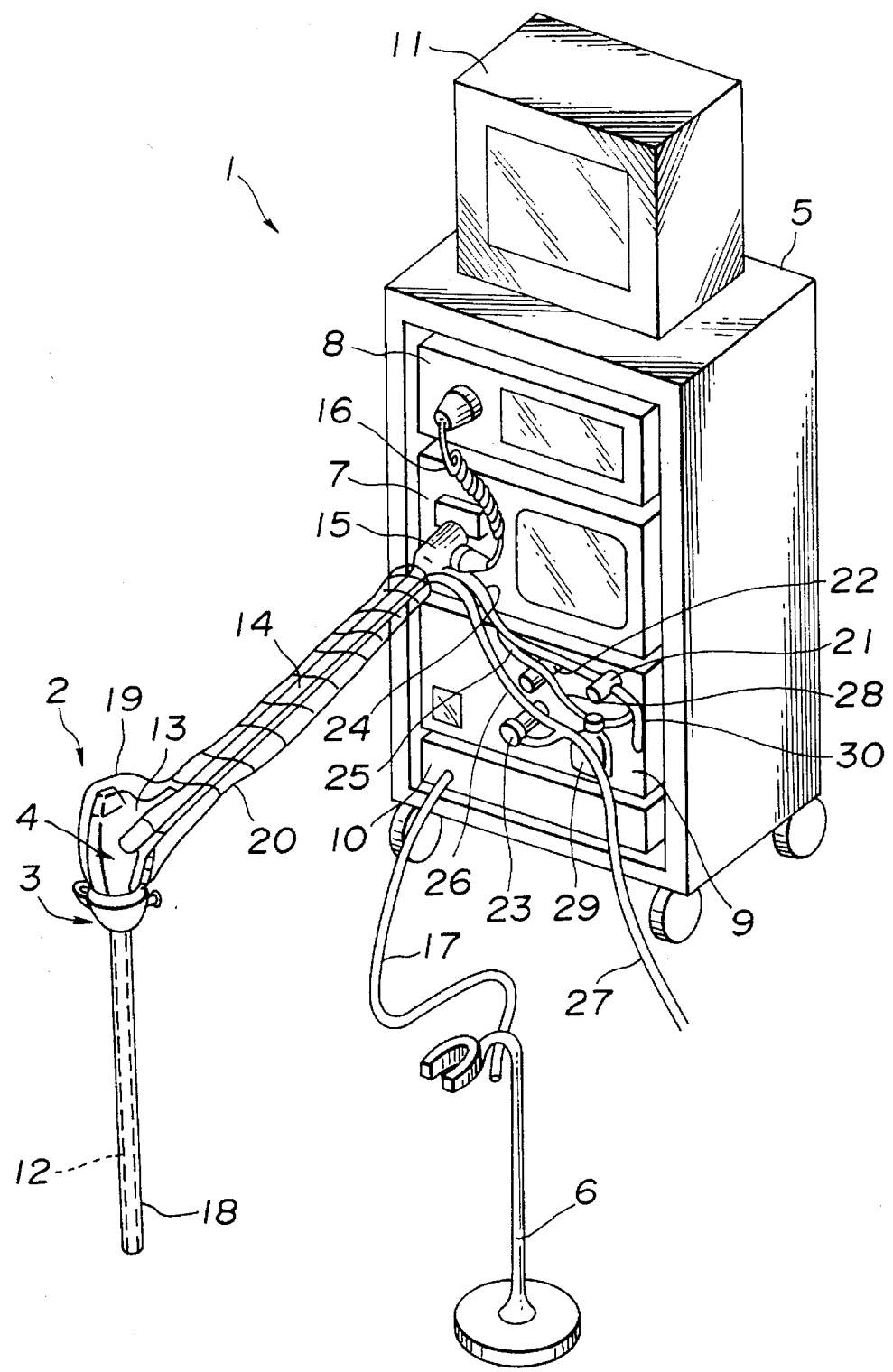
FIG. 8 is a drawing showing the entire construction of the endoscope cover assembly system related to the second embodiment and the endoscope apparatus.
Figure 9:
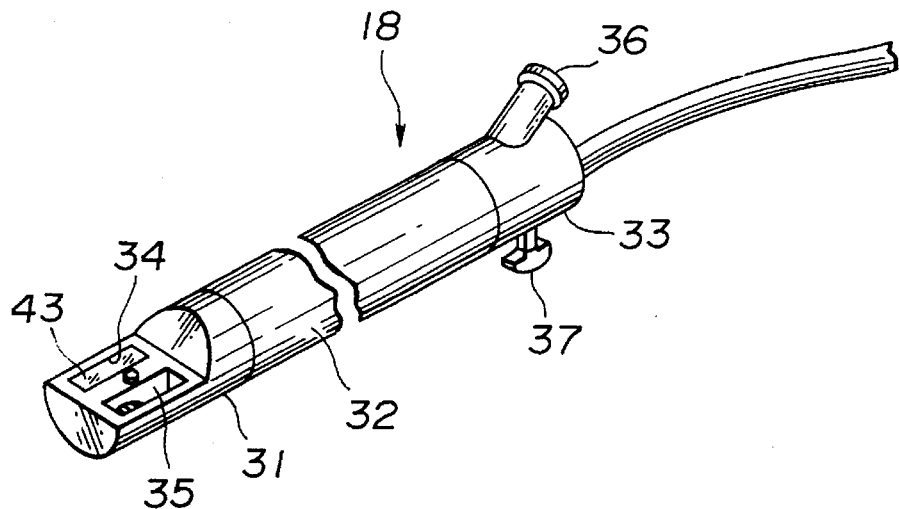
FIG. 9 is a perspective view showing the entire construction of an insertion section covering portion.
Figure 10:
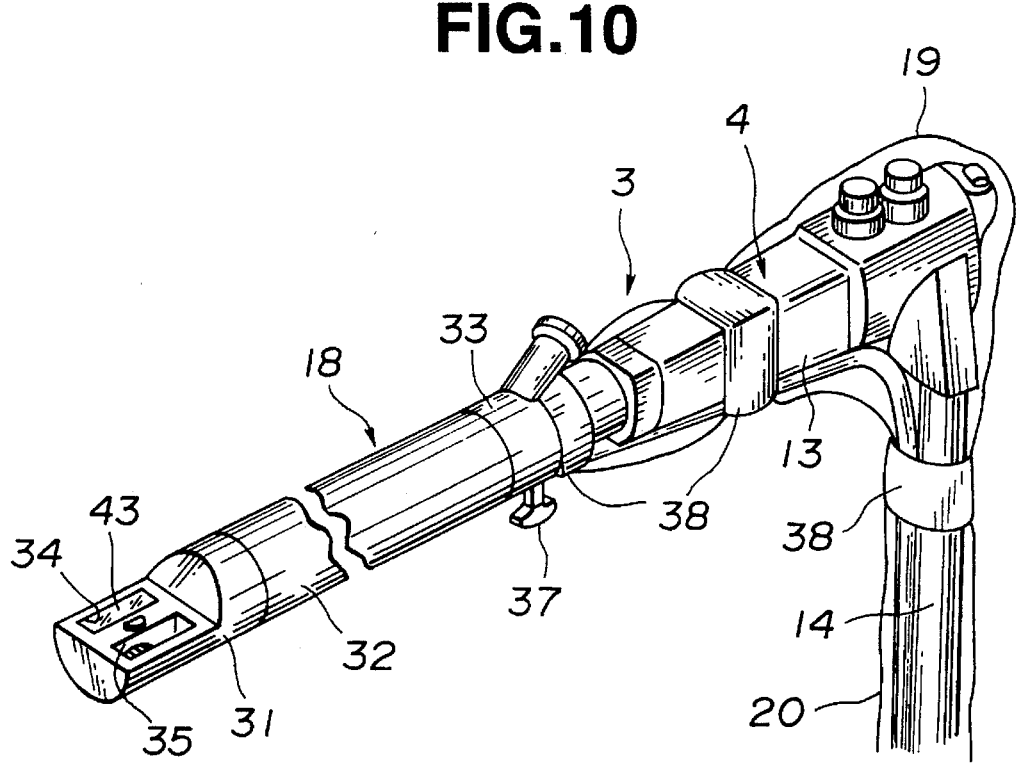
FIG. 10 is a perspective view showing the insertion section covering portion mounted on the endoscope.
Figure 11:
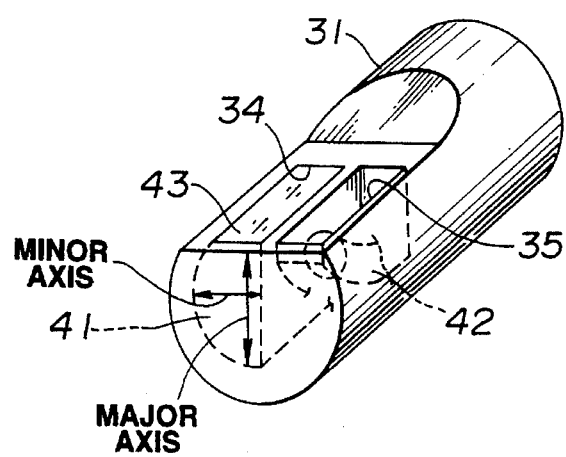
FIG. 11 is a perspective view showing the construction of the front end of the insertion section covering portion.
Figure 12:
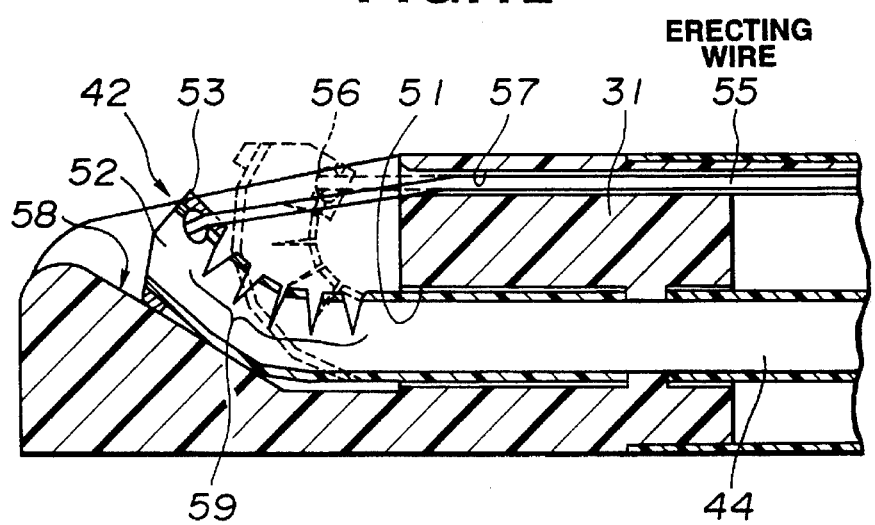
FIG. 12 is a sectional view showing the construction of the front end of the insertion section covering portion.
Figure 13:
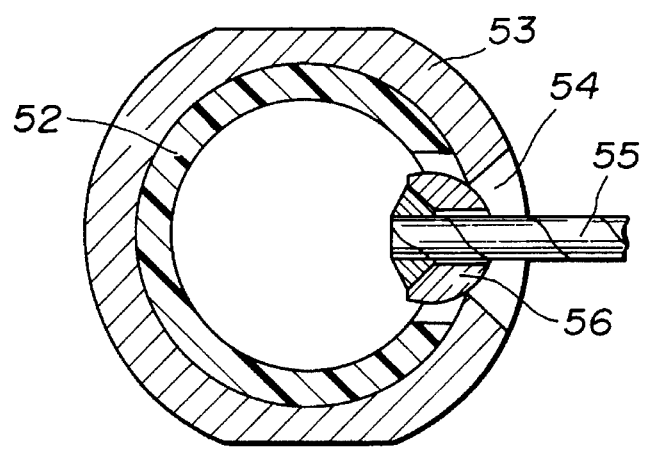
FIG. 13 is a sectional view showing the portion in which a wire is connected to a wire fixing member.

FIGS. 8–13 are related to the second embodiment of the present embodiment. FIG. 8 is a view showing the entire construction of the cover-system endoscope and the endoscope apparatus. FIG. 9 is a perspective view showing the entire construction of the insertion section covering portion. FIG. 10 is a perspective view showing the condition in which the insertion section covering portion is mounted on the endoscope. FIG. 11 is a perspective view showing the construction of the end part of the insertion section covering portion. FIG. 12 is a sectional view showing the construction of the end part of the insertion section covering portion. FIG. 13 shows the portion in which the wire is connected to a wire attaching member.

As shown in FIG. 8, the endoscope apparatus 1 contains the cover-system endoscope 2. The cover-system endoscope 2 comprises an endoscope cover assembly having channels 3 (hereinafter referred to as an endoscope cover assembly) in which an air/water feeding channel, a suction pipe, a medical treatment instrument introducing channel and the like are provided as well as a cover-type endoscope 4 which is to be mounted on the endoscope cover assembly 3.

When endoscope inspection is performed, the insertion section and the other parts of the cover-type endoscope 4 are covered with a clean endoscope cover assembly 3. After the inspection, the endoscope cover assembly 3 is disposed and, on the other hand, the cover-type endoscope is covered with the clean endoscope cover assembly 3 and thus can be used repeatedly. Thus, if the removal of the endoscope cover assembly 3, after inspection is performed without any mistakes (for example, staining the cover-type endoscope 4), it is not necessary to clean and disinfect the cover-type endoscope 4.

The endoscope apparatus 1 comprises the cover-system endoscope 2, a cart containing various peripheral devices to which the cover-system endoscope 2 is connected, and a cover holding device 6 for holding the cover-system endoscope 2.

The cart 5 contains a light source unit 7 which supplies illumination light to the cover-type endoscope 4, a video processor 8 which performs signal processing for an imaging means of the cover-type endoscope 4, a fluid control unit 9 which controls feeding of water/air through the fluid pipe provided on the endoscope cover assembly 3, and an endoscope cover assembly expanding device (hereinafter referred to as an expanding device) 10 which is used for mounting the cover-type endoscope 4 onto the endoscope cover assembly 3. Additionally, a monitor 11 which displays endoscope images receiving image signals from the video processor 8 is mounted on the top of the cart 5.

The cover-type endoscope 4 contains an endoscope insertion section 12 which is narrow, long and flexible, an operating unit 13 which is provided on the beginning end on the operator's side of the endoscope insertion section 12, acting as a large-diameter grip, and a universal cord 14 which extends from the side of the operating unit 13. The universal cord 14 is provided with a connector 15 on the end.

The cover-type endoscope 4 is detachably connected to the light source unit 7 via the connector 15 and the light source unit 7 supplies illumination light to the cover-type endoscope 4. The video processor 8 is detachably connected to the cover-type endoscope 4 via a signal cable 16 which extends from the side of the connector 15, drives the imaging means incorporated in the cover-type endoscope 4, performs signal processing of signals output from the imaging means to convert the signals to standard image signals and then outputs the standard image signals to the monitor 11.

An expanding tube 17 is connected to the expanding unit and the expanding unit 10 expands the endoscope cover assembly 3 by feeding air into the endoscope cover assembly via the expanding tube 17, thereby making it easy to mount and remove the endoscope cover assembly on and from the cover-type endoscope 4. The cover holding device 6 holds the beginning end of the endoscope cover assembly 3 for the cover-type endoscope to be inserted or removed into/from the endoscope cover assembly, respectively.

The endoscope cover assembly 3 comprises the insertion section covering portion 18 of soft material, an operating unit covering portion 19 composed of thin, flexible polymeric material such as vinyl chloride and a universal cord covering portion 20. The covering portions 18, 19 and 20 cover the endoscope insertion section 12, the operating unit 13 and the universal cord 14 of the cover-type endoscope 4.

The fluid control unit 9 contains an air feed control valve 21, a water feed control valve 22 and a suction control valve 23. Air feed, water feed and suction are controlled by these solenoid valves. An air feed pipe 24, a water feed pipe 25 and a suction pipe 26 which extend from the insertion section covering portion 18 are connected to the air feed control valve 21, the water feed control valve 22 and the suction control valve 23, respectively.

A suction tube 27 is connected to the suction control valve 23 and the end of the suction tube 27 is connected to a suction device (not shown) in order to suck unnecessary body fluid through the endoscope end. A water feed tube 28 is connected to the water feed control valve 22 and the end of the water feed tube is connected to a water tank 29. Two air feed tubes 30 extend from the fluid control unit 9 and are connected to the air control valve 21 and the water tank 29.

FIG. 9 shows the entire construction of the insertion section covering portion 18 of the endoscope cover assembly 3. The insertion section 18 comprises a front end cover component 31, cover skin 32 and an endoscope operating unit fixing mouth portion (hereinafter referred to as a mouth portion) for fixing the operating unit 13 of the endoscope thereto, which are connected to each other in order from the front end of the insertion section covering portion so that they are water tight.

As shown in FIG. 11, an observational opening 34 and a channel opening 35 are disposed in the front end cover component 31. A transparent cover glass 43 is disposed in the observational opening 34 so that it faces an observational window and an illumination window of an endoscope which is to be inserted in the inside of the cover, thereby making it possible to irradiate illumination light to and observe an inspected body portion. That is, the cover-type endoscope used in the present embodiment is of side view type.

As shown in FIG. 9, the mouth portion 33 is provided with a medical treatment instrument inserting port 36 which communicates with a medical treatment instrument channel 44 which is provided internally as shown in FIG. 12 and a medical treatment instrument erecting lever 37 which is a means for erecting a medical treatment instrument such as a clamp which is inserted through the medical treatment instrument channel 44 from this medical treatment instrument inserting port. The medical treatment instrument erecting lever 37 is for driving a direction changing means which is disposed at the front end cover component 31 and will be described later.

FIG. 10 shows the condition in which the endoscope cover assembly 3 is mounted on the cover-type endoscope 4.

The insertion section 12 of the cover-type endoscope is inserted into the insertion section covering portion 18 and the operating unit of the endoscope is covered with the operating unit covering portion 19. After a universal cord 14 is covered with a universal cord covering portion 20, fixing tapes are wound around joint parts of the respective covers to fix the covers. As a result, the respective parts of the cover-type endoscope 4 are covered with the endoscope cover assembly 3 (covering portions 18, 19, 20) so that they are water tight, thereby being protected from the external environment.

FIG. 11 shows the construction of the front end component 31 of the endoscope cover assembly 4.

The front end component 31 is composed of hard resin, communicating with the endoscope insertion channel provided within the insertion section covering portion 18, and includes an endoscope front end insertion hole 41 with which the endoscope front end is engaged, and a medical treatment instrument guiding device 42 which is a direction changing means disposed at the front end of and communicating with the medical treatment instrument channel 44. As shown in FIG. 11, the cross section of the endoscope front end insertion hole 41, taken perpendicularly to the axis is a semicircle a part of which is cut out. The cross section of the endoscope front end insertion hole 41 has major and minor axes, so that the cover glass 43 is disposed on the extending side of the major axis and the medical treatment instrument guiding device 42 is disposed along the extending line of the minor axis. This arrangement allows the components incorporated in the insertion portion to be arranged effectively in the cross section of the insertion portion front end. Thus, when the endoscope 4 is mounted in the insertion section covering portion 18, the external shape of the insertion section is formed in an almost circular shape (circle a part of which is cut out because the endoscope is of side view type), so that ease of insertion of the endoscope is not limited.

The medical treatment instrument guiding device 42 is open to outside. On the observational opening 34 provided on the side of the endoscope front end insertion hole 41, the cover glass 43 is provided to allow light to be transmitted therethrough, separating the endoscope front end provided inside from the external environment.

FIG. 12 shows a sectional view of the medical treatment instrument guiding device 42, taken along the axis of the insertion portion. The second embodiment presents a simpler construction in which the medical treatment instrument 42 is formed of a tube body having cutouts as described below.

An erecting tube fixing hole 51 which opens to a slope of the front end of the front end cover component 31 communicates with the suction tube 27. The beginning end of the erecting tube 52 which forms the medical treatment instrument guiding device 42 is inserted into and fixed to the erecting tube fixing hole 51. The erecting tube 52 communicates with the suction tube 27 and guides the front end of a medical treatment instrument inserted through the suction tube 27.

As shown in FIG. 13, a ring shaped wire fixing member 53 is provided on the front end of the erecting tube 52. Some measure for preventing light reflection, for example, use of black material or coating the surface with black, is taken to the wire fixing member 53 to minimize an influence of reflected illumination light upon observation when the erecting tube 52 is curved so as to enter into the field of view of the endoscope.

A conically dented wire insertion hole 54 is provided on the wire fixing member 53 and the wire insertion hole 54 allows the front end of the erecting wire 55 which is a communicating means to be inserted therethrough. The front end of the erecting wire 55 is seized by means of a substantially spherical wire stopper 56 so as to be connected to the wire fixing member 53. The wire stopper 56 is fixed to the front end of the erecting wire by using adhesive or welding. The diameter of the wire stopper 56 is larger than that of the wire insertion hole 54 so as to prevent the erecting wire from being loose.

The erecting wire 55 and the wire stopper 56 are not fastened to the wire stopper 53, so that the erecting wire 55 is three-dimensionally rotatable via the spherical surface of the wire stopper 56.

The erecting wire 55 extends into the insertion section covering portion 18 through a wire introducing hole 57 provided in the front end cover component 31 and further is connected to the medical treatment instrument erecting lever 37 disposed at the mouth portion 33. Thus it is possible to erect the erecting tube which is substantially linear so as to be curved as shown in FIG. 12 by operating the medical treatment instrument erecting lever 37 to pull and push the erecting wire 55 and thus it is possible to change the direction of the protrusion of a medical treatment instrument (not shown) which protrudes from the front end of the erecting tube 52.

V-shape grooves 59 are provided on a single side of the erecting tube 52, which the erecting wire 55 is fastened onto and is near the front end of the erecting tube 52. That is, the V-shape grooves are provided on the portion which will be curved when the erecting wire 55 is pulled or pushed.

As regards the V-shape groove 59, assuming the diameter of the erecting tube 52 is d, it is desirable that the depth of the groove is 0.25d–0.75d, a pitch between the grooves is 1 mm–3 mm, the number of the grooves is 2–6 and the angle of the V-shape groove is 15°–45°. An inclined surface 58 is provided in the front end cover component 31 for the erecting tube 52 so as to be placed at an angle of 10°–40° with respect to the axis of the insertion section covering portion 18.

Next, the operation of the second embodiment will be described below.

For treatment with an endoscope, an endoscope operator inserts a medical treatment instrument from the medical treatment instrument inserting port 36, introduces the instrument through the suction tube 27, the front end cover component 31 and the erecting tube 52, and then makes the front end of the instrument protrude into the body cavity. Then he operates the medical treatment instrument erecting lever 37 provided on the mouth portion 33 in order to introduce the front end of the medical treatment instrument to a desired treatment portion of the body cavity. The erecting wire 55 is pushed or pulled by operator's operating the medical treatment instrument erecting lever 37 and accompanied with this movement, the wire fixing member 53 which is rotatably connected to the erecting wire 55 is moved back and forth.

Therefore, the erecting tube 52 is curved as shown in FIG. 12. If a tube body is curved step by step, the tube body buckles when a bending stress exceeding a specific level is applied. However, in the second embodiment, the stress is dissipated because the tube 52 contains the V-shape groove 59, so that the sectional view of the tube 52 is deformed only slightly but the tube does not buckle. Thus even when the tube is curved, it is possible to secure a tube cavity.

That is, if the erecting tube 52 is curved so that the direction of the protrusion of the medical treatment instrument is changed, the hollow condition of the erecting tube 52 is maintained so that the medical treatment instrument can be inserted and removed securely. Because the erecting tube 52 is partially cut out, the tube can be curved by a smaller pulling force of the erecting wire 55. Thus it is possible to reduce the operating force of the medical treatment instrument erecting lever 37.

According to the second embodiment, it is possible to guide the direction of medical treatment instrument's protrusion by means of a simpler construction because the direction changing means is composed of a tube body. Additionally, because the V-shape grooves are provided on the tube body, the tube body does not buckle when it is curved, so that it is possible to move a medical treatment instrument back and forth smoothly. The present embodiment is capable of providing a cheap endoscope cover assembly and cover-system endoscope because the direction changing means is structured in a simple way.

Next, the third embodiment of the present invention will be described with reference to FIG. 14.

According to the third embodiment, an erecting tube 52A having a cutout section 60 which is provided so that the cross section perpendicular to the axis of the tube is semicircle instead of the V-shape groove 59 provided on the erecting tube 52 according to the second embodiment is mounted.

According to the present embodiment, the tube deformation level is increased as compared with the second embodiment (the function of maintaining the hollow status is decreased), however, the force required for operating the medical treatment instrument erecting lever is largely reduced. The construction, the operation and the effect of the third embodiment are the same as the second embodiment, thus the explanation about these is omitted.

Next, the fourth embodiment of the present invention will be described with reference to FIG. 15.

Although the V-shape grooves 59 are provided on only a single side of the erecting tube 52 according to the second embodiment, the fourth embodiment uses erecting tubes 52B, 52C having the V-shape grooves provided on both sides.

As regards the construction described above, it is permissible to provide the V-shape grooves 59 so that the bottoms of the V-shape grooves on the corresponding sides are alternate as shown in FIG. 15(a) and it is also permissible to provide the V-shape grooves that the bottoms face each other as shown in FIG. 15(b). The present embodiment has almost the same operation and effect as the second embodiment. The construction, the operation and the effect of the present embodiment are the same as the second embodiment, thus the explanation about them is omitted.

Next, the fifth embodiment of the present invention will be described with reference to FIG. 16.

According to the fifth embodiment, in addition to the construction of the second embodiment, a curved stopper 62 is provided at the front end cover component so that the curved stopper runs along the inscribing circle of the erecting tube 52. The description about the same construction and operation as the second embodiment is omitted while the same reference numerals are given to corresponding parts.

In addition to the effects of the second embodiment, by providing the curved stopper 62, the fifth embodiment provides such an effect that the erecting tube is not curved over its specific angle to prevent the erecting tube from being buckled when the erecting wire 55 is pulled excessively.

In the second–sixth embodiments, the wire is pulled to erect the erecting tube. On the other hand, when placing down the erecting tube, the wire is slacked and the restoring forces of the erecting tube and a medical treatment instrument inserted through the erecting tube are used.

The restoring forces of some medical treatment instruments from the state of being bent to that of being straight are weak and some medical treatment instruments are not placed down sufficiently. The sixth embodiment having a construction for solving this problem will be described with reference to FIG. 17.

In the sixth embodiment, instead of the erecting tube 52 of the second embodiment, a tube having a coil wound around the circumference of its end is provided.

Figure 17:
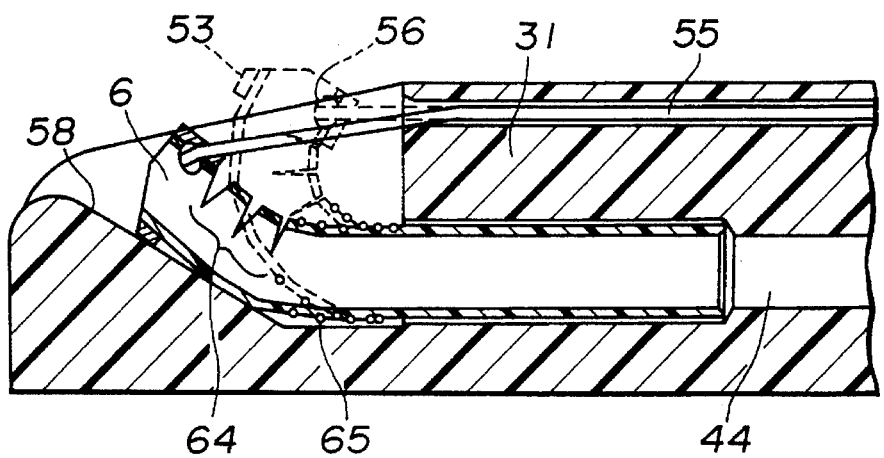
FIG. 17 is a sectional view showing the construction of the front end of the insertion section covering portion of the sixth embodiment.

The erecting tube 63 shown in FIG. 17 has V-shape grooves provided in the range which is curved by the operation for erecting. Further, the erecting tube 63 has a coil 65 wound around the leading section of the curve portion. The description of the same construction and the operation of the present embodiment as the second embodiment is omitted while the same reference numerals are attached to corresponding parts.

According to the previous embodiment, in addition to the effect of the second embodiment, the coil 65 is also curved when the erecting tube 63 is curved. At this time, a force of restoring to the state of being straight is accumulated in the coil 65. When placing down the erecting tube 63, a restoring force of the coil 65 to the state of being straight as well as a pushed force of the erecting wire are applied so as to secure a sufficient force for placing down the erecting tube 63.

Next, an example in which the connection of the erecting tube and the wire has been modified will be described with reference to FIGS. 18 and 19.

Different from the construction shown in FIG. 6, the present modified example has a ring-like member at the end of the wire and the end of the erecting tube is inserted through the ring-like member. The description of the same construction and operation as the second embodiment is omitted while the same reference numerals are attached to corresponding parts and only different points from the second embodiment will be described.

Figure 18:
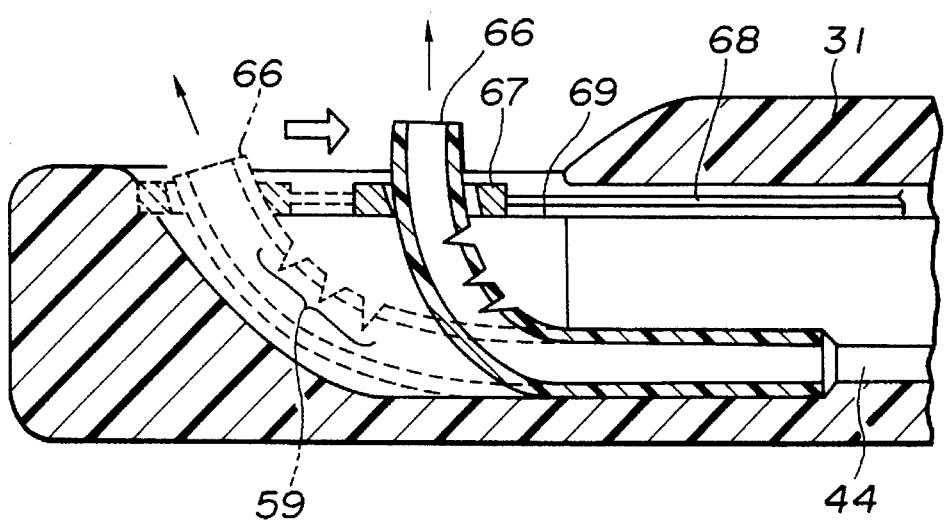
FIG. 18 is a sectional view showing the construction of the front end of the insertion section covering portion of an modified example.
Figure 19:
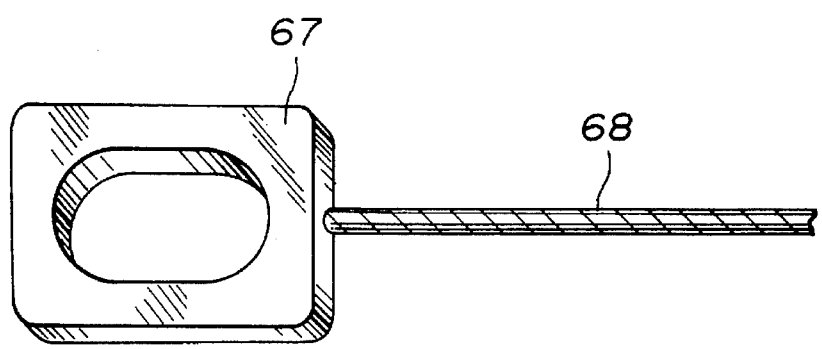
FIG. 19 is a perspective view showing an erecting tube guiding member which is used in the modified example.

As shown in FIG. 18, only the operating-unit-side end of the erecting tube 66 is fixed to the erecting tube fixing hole of the front end cover component 31. The other end of the erecting tube 66 runs through a hole provided on the erecting tube guiding member 67. As shown in FIG. 19, an end of the wire 68 is fixed to the erecting tube guiding member 67. The erecting tube guiding member 67 is adapted so as to move on a rail 69 provided in the front end cover component 31 freely when the wire 68 is pulled or pushed.

Figure 22A:
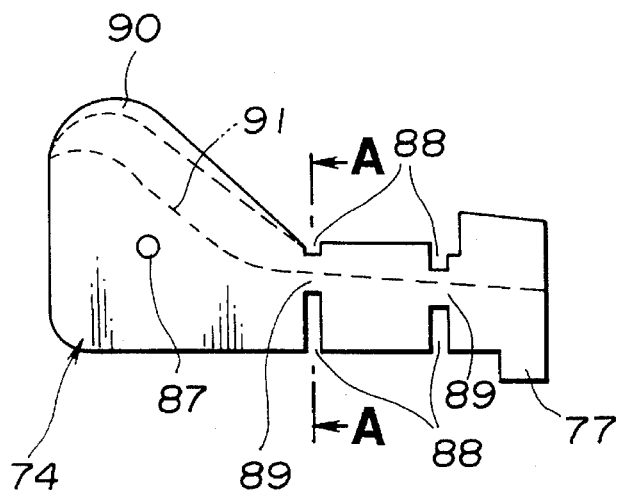
FIG. 22(a) is a drawing showing the construction of the erecting base.
Figure 22B:
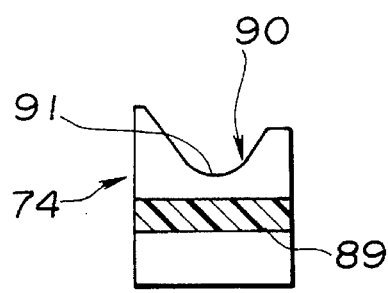
FIG. 22(b) is a cross-section of FIG. 22(a) taken along the line A—A.
Figure 23:
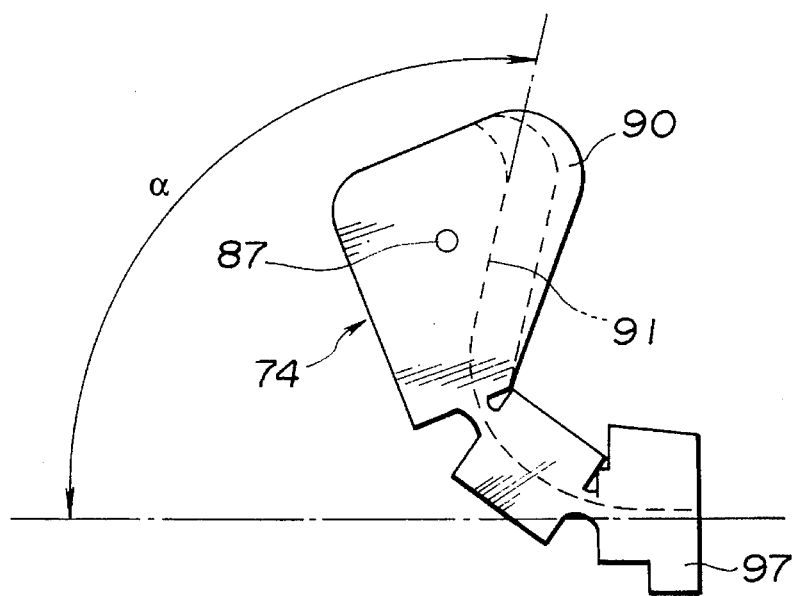
FIG. 23 is an explanatory drawing showing the operation of the erecting base.

The construction and the operation of the present embodiment are as the same as the second embodiment, thus the description of them is omitted. FIGS. 20–24 are related to the seventh embodiment of the present invention. FIG. 20 is a perspective view showing the construction of the front end cover component. FIG. 21 is a side sectional view of the insertion section covering portion. FIG. 22 is a diagram showing the construction of the erecting base. FIG. 23 is a diagram explaining the movement of the erecting base. FIG. 24(*a*) is a front view of the front end showing the positional relation between the erecting base and a hard member. FIG. 24(*b*) is a view of the direction of the arrow C in FIG. 24(*a*). FIG. 24(*c*) is a front view of the front end when the erecting base is erected. FIG. 24(d) is a view of the direction of the arrow D in FIG. 24(*c*).

The seventh embodiment has an insertion section covering portion 18A which has a different direction changing means instead of the insertion section covering portion 18 of the eighth embodiment. As regards the erecting device, although the eighth embodiment employs a tube like erecting device, the present uses a embodiment employs a trapezoid member in which a hinge is formed. The description of the same construction and the operation as the eighth embodiment is omitted while the same reference numerals are attached and thus only different points from the eighth embodiment will be described.

The insertion section covering portion 18A has a front end cover component 31A instead of the front end cover component 31 of the insertion section covering portion 18 shown in FIG. 11.

The construction of the front end cover component 31A is shown in FIGS. 20(*a*), (*b*) and (*c*).

The front end cover component 31A comprises an external cap 70 composed of polymeric material shown in FIG. 20(*b*) and a hard member 71 shown in FIG. 20(*a*). The hard member 71 communicates with the endoscope insertion channel provided in the insertion section covering portion 18A and contains an endoscope front end inserting hole 72 with which the endoscope front end engages and a channel opening 73 which communicates with the medical treatment instrument channel. Further, the hard member 71 contains an erecting base 74 which is disposed in front of the channel opening 73 forming a direction changing means and a metallic wire 76 which is introduced into a wire introducing hole 75 disposed near the channel opening 73 while one end of the wire is connected to the erecting base 74.

The erecting base 74 is disposed so that it is off the center axis of the cross section of the cap 70.

The erecting base 74 has an operator's side fixing portion and one end of the operator's side fixing portion 77 is fixed to an engagement groove 78 provided in the, hard member 71.

The cap 70 has a front end opening 69 and can be inserted into the front end of the hard member 71. At this time, the cover glass of the observational opening 34 and the erecting base 74 are introduced to the front end opening 69. A cap operator's side opening 79 as shown in FIG. 20(*c*) is formed at the insertion end of the cap 70 shown in FIG. 20(*b*). In the cap operator's side opening 79, a fixing groove 80 which engages with the other end of the operator's side fixing portion 77 of the erecting base 74 is provided. At the edge of the cap operator's side opening 79, a plurality of locking portions 82 which engage with an engagement groove provided along the circumference of the hard member 71 are provided. By placing the cap 70 from the front end of the hard member 71, the locking portions 82 engage with the engagement groove 81. The fixing groove 80 of the cap 70 presses the operator's side fixing portion 77 of the erecting base 74 onto the hard member 71 in order to restrict a movement along the circumference by means of the engagement groove 78 and the inside surface of the cap 70. As a result, the operator's side fixing portion of the erecting base 74 is completely fastened. When the cap 70 is fixed to the hard member 71, a channel opening 35 is formed as shown in FIG. 21.

The front end of the insertion section covering portion 18A has a section taken along the axis as shown in FIG. 21. In the insertion section covering portion 18A, the front end of the channel tube 84 constituting the medical treatment channel 83 is connected to the hard member 71 so as to communicate with the channel opening 73. The wire tube 85 is connected to the hard member 71 so as to communicate with the wire introducing hole 75. The wire 76 passes through the insertion section covering portion 18A and further through the wire tube 85 which is connected to the hard member 71 and the operator's end of the wire 76 extends to the mouth portion 33.

In the insertion section covering portion 18A, an endoscope channel (not shown) is provided along the channel tube 84 for the medical treatment channel 83 so as to communicate with the endoscope front end insertion hole 72 within the hard member 71. Thus, the cover-type endoscope can be inserted thereinto.

FIGS. 22 and 23 show the construction and the movement of the erecting base 74.

The erecting base 74 is made of a flexible polymeric material such as polypropylene. As shown in FIG. 22(*a*), the erecting base 74 has a wire fixing hole 87 for fixing the wire 76 to the side at the end of the erecting base. Further, in the middle of the erecting base 74, the erecting base 74 has two grooves which face grooves provided on the other side. Two hinge portions 89 which are provided by thinning the thickness by means of the four grooves are deformed when the wire 76 is pulled by the action of the medical treatment instrument lever 37 at the mouth portion 33, as shown in FIG. 23, so that the erecting base can be erected. That is, the erecting base is curved. Meanwhile, the material of the erecting base 74 is not restricted to flexible materials and, for example, it is permissible to construct the hinge portion 89 using metals formed in the shape of a sheet.

The deformation of the hinge portion is restricted to such angles until both ends of the grooves 88 contact each other. In the present embodiment, for example, two grooves 88 are formed so that the hinge sections can be bent at 20°–45°, respectively. In the present embodiment, an erecting angle α of 70°–120° with respect to the axis of the endoscope cover assembly 3 can be realized. The dotted line shown in FIG. 23 indicates the bottom 91 of a medical treatment instrument 90. The medical treatment instrument inserting/removing 90 is formed in the shape of the letter U as shown in FIG. 22(*b*) showing a sectional view taken along the line A—A in FIG. 22(*a*). Of the two tops of the U-shaped grooves, the top on the cover glass side 34 is formed to be lower than the other top.

FIGS. 24(*a*)–(*d*) show the positional relationship between the erecting base 74 and the hard member 71. FIG. 24(*a*) is a view of the erecting base 74 and the hard member 74 viewed from the front end. FIG. 24(*b*) is a view taken in the direction of the arrow C in FIG. 24(*a*) and also shows the cap 70.

The erecting base 74 is disposed parallel with a wall 71*a* of the hard member 71 which is vertical to the surface on which the cover glass 43 is mounted. Therefore, the erecting base 74 is placed parallel to the center of field of view of the cover glass 43 constituted of the illumination window 43a and the observational window 43b. A wire insertion hole 75 is provided so that a line connected from a bending point 76a of the wire 76 to the wire insertion hole 75 is parallel to the side face of the erecting base 74 and outside of the erecting base 74. Additionally, the wall 71a and the erecting base 74 are arranged so that they have a specified gap t therebetween.

Figure 24A:
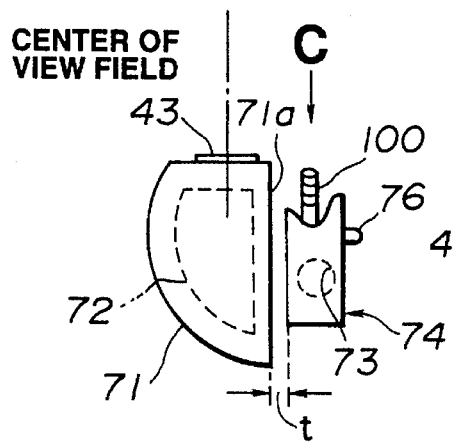
FIG. 24(a) is a front view of the front end showing the positional relationship between the erecting base and the main body of a hard member.
Figure 24B:
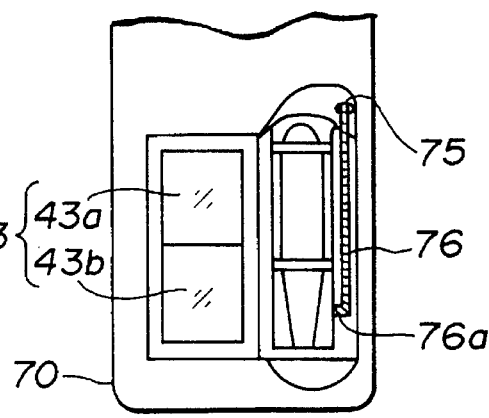
FIG. 24(b) is a view taken along the arrow C in FIG. 24(a)
Figure 24C:
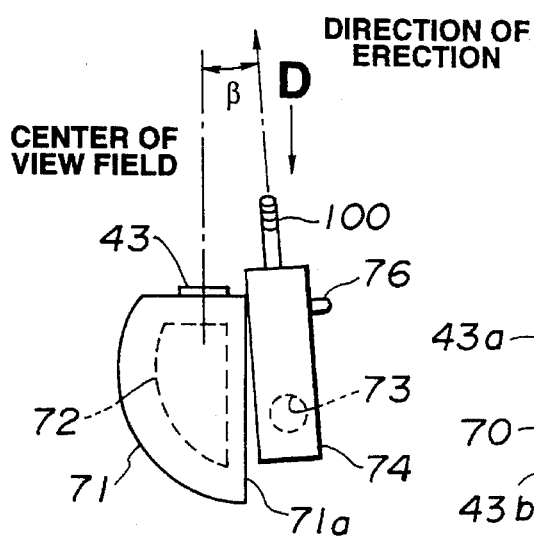
FIG. 24(c) is a front view of the front end showing the erecting base erected.
Figure 24D:
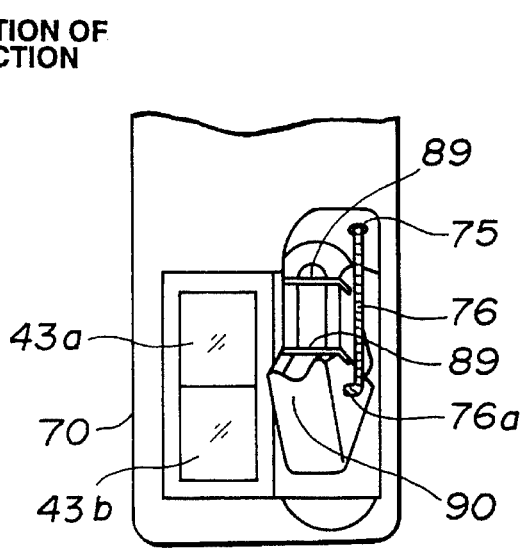
FIG. 24(d) is a view taken along the arrow D in FIG. 24(c).

FIG. 24(c) is a view taken from the front end when the erecting base 74 is erected. FIG. 24(d) is a view in the direction of the arrow D in FIG. 24(d).

If the wire 76 is pulled continuously, the hinge section 89 is deformed so that the erecting base 74 is erected up to the angle α shown in FIG. 23 and a pulling tension is applied to only one side of the erecting base 74 by means of the wire 76 so that the hinge section 89 of the erecting base 74 is slightly twisted along the circumference of the endoscope. Due to the slight twisting of the hinge section 89, the erecting base 74 is inclined along the circumference of the endoscope and contacts a part of the wall 71a as shown in FIGS. 24(c), (d). With this condition, an angle β is formed between the center of the field of view and the direction of erection of the erecting base 74 as shown in FIG. 24(c). By setting the gap t so that the angle β is 2°–10°, it becomes easy to observe through the endoscope and operate the medical treatment instrument 100.

When using the cover-type endoscope according to the construction described above, a disinfected clean endoscope cover assembly 3 is mounted onto the cover-type endoscope. The cover-type endoscope 4 is inserted into an inspection portion in the body cavity as the cover-system endoscope which is separated from external environment. the medical treatment instrument 100 inserted through the medical treatment instrument inserting hole 36 protrudes out of the channel opening 35. To carry out biopsy for an inspection part, the wire 76 is pulled by means of the medical treatment instrument erecting lever 37 to deform the hinge section, erecting the erecting base to change the direction of the protrusion of the medical treatment instrument 100. At this time, the erecting base 74 is erected parallel to the center of the field of view and then slightly twisted along the circumference of the hinge section 89 so that the erecting base 74 is inclined at the angle β with respect to the center of the field of view. As a result, the protrusion of the medical treatment instrument 100 can be directed to the center of the field of view in order to perform medical treatment. Because the top nearer the center of the field of view is formed to be lower than the other top, an approach for introducing the medical treatment instrument to the center of the field of view is slightly shorter than otherwise.

On the other hand, when the wire 76 is slacked, the erecting angle decreases due to a restoring force of hinge section's elasticity. In this manner, it is possible to adjust the erecting angle by pulling or slacking the wire 76.

After a treatment, by operating the medical treatment instrument erecting lever 37 in reverse direction, the wire 76 is slacked to place down the erecting base 74.

After use, the endoscope cover assembly 3 is thrown out.

By using the endoscope cover assembly 3 according to the present embodiment, it becomes unnecessary to clean or disinfect the cover-type endoscope each time inspection is performed, so that the cover-type endoscope 4 can be always used in clean state by simple operation repeatedly.

Because the erecting base 74 of the present embodiment is formed of a flexible material and contains two hinge sections 89, when the erecting base 74 is erected, there is no portion where the medical treatment instrument is bent sharply. Thus, it is possible to erect the medical treatment instrument smoothly without damages.

Further, according to the present embodiment, the portion which will be curved in the erecting base 74 is only the hinge section. Therefore, the twisting of the erecting base 74 is smaller as compared with the case in which the entire erecting base is made of a thin elastic material. For this reason, it is possible to make the medical treatment instrument protrude in a target direction securely. By setting a target direction in this manner, it is possible to direct the medical treatment instrument to the center of the field of view by hinge section's deformation to the center of the field of view and hinge section's inclination along the circumference. Thus, it is not necessary to make the medical treatment instrument contact an inspection portion by means of a wire and thus there is no possibility that the soft medical treatment instrument will be damaged.

In the endoscope according to the present embodiment, by providing the erecting base with at least a hinge section, the medical treatment instrument is prevented from being entirely twisted and further, a twisting which is caused slightly is used positively. That is, the endoscope of the present embodiment is arranged so that the erecting base 74 is inclined toward the center of the field of view of the observational window and then erected by means of the wire which is placed outside of the erecting base and connected to the erecting base to pull the erecting base and by means of the wire introducing hole which is disposed to apply a slight twisting force or bending moment to the erecting base via the wire so as to incline the erecting base to the center of the field of view for observation when the wire is pulled.

According to the present embodiment, the inclination angle β of the erecting base 74 toward the center of the field of view when the erecting base is erected is determined depending on the gap t between the wall 71a and the erecting base 74, so that a slight twisting of the hinge section 89 of the erecting base 74 along the circumference is restricted. As a result, it is possible to erect a hard medical treatment instrument as well as a flexible medical treatment instrument in a specified direction, so that operators can operate the medical treatment instrument very easily. Because the erecting base 74 is made of a polymeric material in the present embodiment, even if the electric conductive portion of a high-frequency treatment instrument (for example, papillotomy knife) touches the erecting base, the erecting base is not broken.

Further, in the present embodiment, the construction of the front end cover component is simple, and thus the outside diameter of the component is not increased over a specific one.

Although according to the present embodiment, the wire is made of metal, it is permissible to make the wire of a polymeric material. As an effect of this case, the electric insulating property of the endoscope cover assembly 3 is increased.

As regards the arrangement of the erecting base, it is permissible to arrange the erecting base in an order reverse to the present embodiment. In this case, the endoscope channel is also arranged reversely.

Figure 25A:
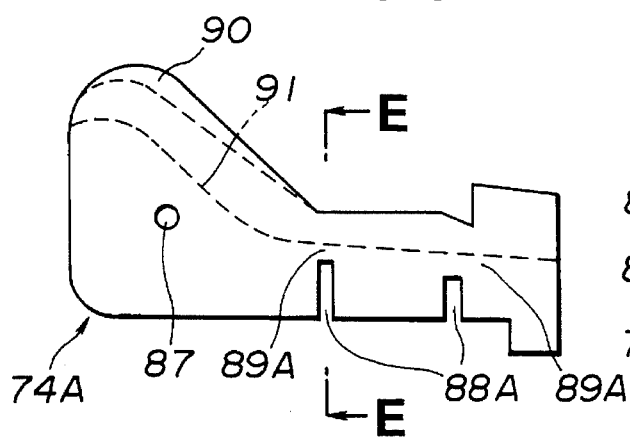
FIG. 25(a) is a side view of the erecting base related to the first modified example of the seventh embodiment.
Figure 25B:
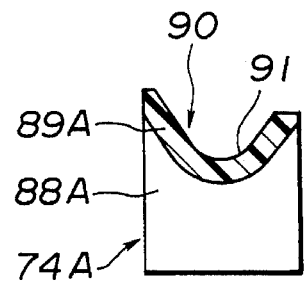
FIG. 25(b) is a sectional view taken along the lines E—E in FIG. 25(a).

FIG. 25 shows the erecting base related to the first modified example. FIG. 25(a) is a side view of the erecting base and FIG. 25(b) is a sectional view taken along the line

E—E.

Different from the seventh embodiment, the erecting base 74A of the present embodiment has no grooves 88 on the upper side and two grooves 88A on only the lower side. The description of the same construction and operation as the seventh embodiment is omitted while the same reference numerals are attached.

In the erecting base 74A, as shown in FIG. 25(b), as regards the groove 88A, the medical treatment instrument inserting/removing groove 90 side is formed along the shape of the inserting/removing groove 90 so as to provide the hinge section with almost the same thickness.

According to the construction described above, it is possible to form the medical treatment instrument inserting/removing groove 90 very smoothly so that the medical treatment instrument can be inserted or removed smoothly. Additionally, because the thickness of the hinge section 89A is almost uniform, it is possible to erect the medical treatment instrument as smoothly as the seventh embodiment.

The construction, the operation and the effect of the present embodiment are the same as the seventh embodiment, and thus the description of them is omitted.

Figure 26:
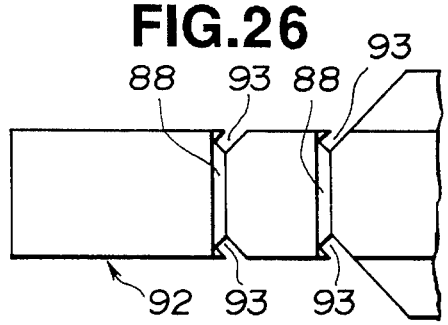
FIGS. 26 and 27 are related to the second modified example of the seventh embodiment.
Figure 27:
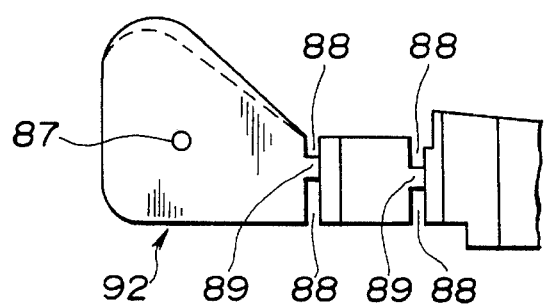

FIGS. 26, 27 show erecting bases related to the second modified examples of the seventh embodiment. FIG. 26 shows the top view of the erecting base and FIG. 27 shows the side view of the erecting base.

The present modified example has another erecting base 92 instead of the erecting base 74. The erecting base 92 has the grooves 88 like the seventh embodiment and the hinge section 89. As shown in FIG. 26, the erecting base 92 has oblique grooves 93 on both ends of the grooves 88. The oblique grooves 93 are formed so that they run obliquely from the operator's side of the erecting base 92 to the front end.

As regards the erecting base 92 of the construction described above, when the hinge section 89 is bent to erect the erecting base 92, the upper portion of the oblique groove 93 (the portion above the hinge section 89 shown in FIG. 27) is closed and engaged via the oblique groove 93. Thus, even if a sharp twisting force is caused in a part of the erecting base, the twisting is restricted due to the engagement described above.

Because the present modified example is constructed to be highly resistant to twisting, the stiffness of the material of the erecting base 92 is not required so much and thus a cheap material can be used.

The construction, the operation and the effect of the present modified example are the same as the seventh embodiment and thus the description about them is omitted.

Figure 28:
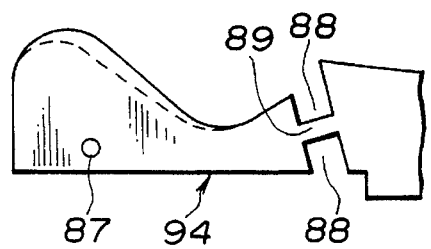
FIG. 28 is a drawing showing the construction of the erecting base related to the third modified example of the seventh embodiment.

FIG. 28 shows an erecting base related to the third modified example.

The erecting base 94 shown in FIG. 28 has only one section in which the grooves facing each other are provided and these facing grooves are formed obliquely with respect to the axis of the endoscope cover assembly. Because the erecting base 94 of this modified example is constructed so that only one hinge section is bent, it operates in the same manner as an erecting base which is used in conventional endoscopes and erected by rotational movement. This embodiment can be used in the same manner as conventional reuse type (without a cover) endoscope and allows operators to handle the endoscope very easily.

Figure 29:
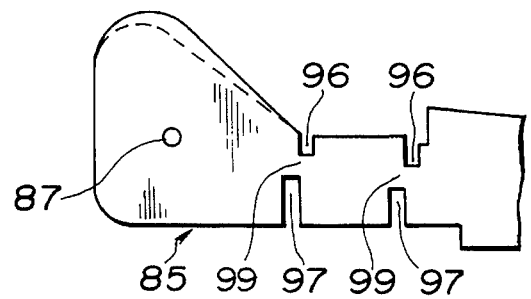
FIG. 29 is a drawing showing the construction of the erecting base related to the fourth modified example of the seventh embodiment.

FIG. 29 shows an erecting base related to the fourth modified example.

Although the erecting base 95 shown in FIG. 29 has the same number of grooves as that shown in FIG. 22, the grooves are provided so that they do not face each other. That is, in the erecting base 97 described above, lower grooves 97 are provided so that they are deviated slightly to the front end from the upper grooves 96. In the hinge section formed between the grooves 96 and 97, the volume of a portion having a minimum thickness can be reduced. The hinge section is as easy as the previous modified example to bend and the mechanical strength is improved thereby improving the durability.

The construction, the operation and the effect of the present modified example are the same as the seventh embodiment and thus the description about them is omitted.

Figure 30:
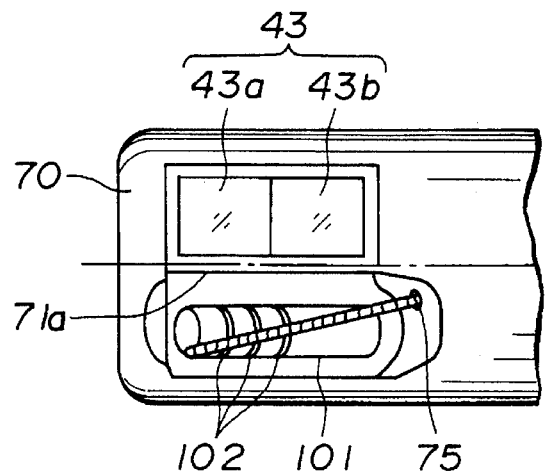
FIGS. 30–32 are related to the eighth embodiment and FIG. 30 is a top view of the cover showing an erecting tube.
Figure 31:
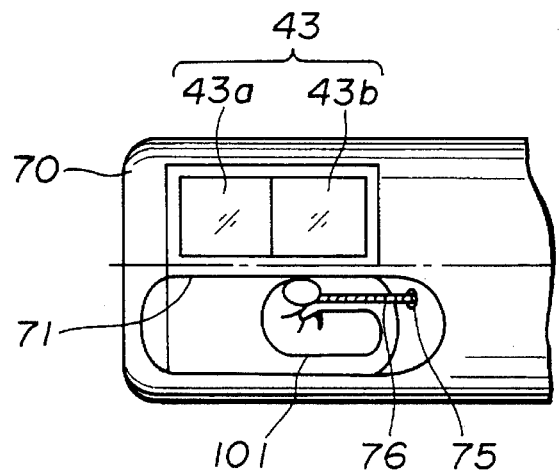
Figure 32:
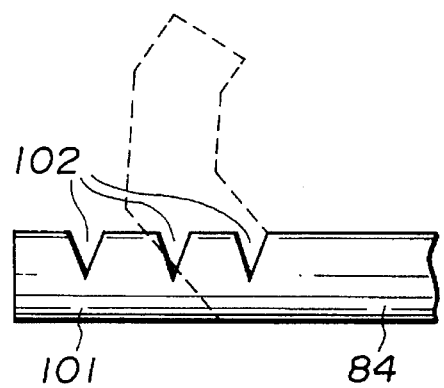

FIGS. 30–32 are related to the eight embodiment of the present embodiment. FIG. 30 is a top view of the cover showing an erecting tube. FIG. 31 is a top view of the cover showing the movement of the erecting tube and FIG. 32 is a side view showing the movement of the erecting tube.

The present embodiment is different from the seventh embodiment in respect to only the erecting base and thus only the erecting base will be explained. As for the same construction and the operation as the seventh embodiment, the description is omitted while the same reference numerals are attached.

As regards the direction changing means shown in FIG. 30, the erecting tube 101 extends from the channel tube 84 as shown in FIG. 32 toward the cap 70 and has three cutouts 102 on its upper portion. This erecting tube 101 can be referred to as an erecting base having a cover. By forming the cutouts 102, the hinge sections are formed in the erecting tube 101.

As shown in FIG. 30, an end of the wire 76 is inserted into the wire introducing hole 75 provided near the center of the hard member 71 relative to the erecting tube 101 and connected to the erecting lever 37. The wire 76 is connected to the front end of the erecting tube 101 which is the farthest from the center of the hard member 71.

If the wire 76 is pulled in the construction described above, the erecting tube 101 is erected as shown by the dotted line in FIG. 32 so that the erecting base 97 is twisted toward the center of the hard member 71 as shown in FIG. 31, thereby inclining a medical treatment instrument toward the center of the field of view.

Because, according to the present embodiment, the erecting tube 101 is formed so that it extends from the channel tube 84, a tube continues smoothly from the medical treatment channel 84 to the erecting tube 101, so that there is no fear that the medical treatment instrument may be hooked, allowing operators to use conveniently.

Additionally, because, in the present embodiment, the erecting tube 101 is formed of the channel tube 84, the number of required parts can be reduced, thereby making it possible to provide a cheap endoscope.

Further, the angle of the inclination of the erecting tube 101 is restricted to that until the erecting tube 101 contacts the wall 71a, so that it is possible to always obtain a specific angle regardless of the hardness of the medical treatment instrument. For this reason, this embodiment provides a high operability for operators.

Although, according to the present embodiment, the erecting tube 101 is formed by providing the channel tube 84 with the cutouts 102, it is permissible to form a construction having no cutout by forming the channel tube 84 of a softer material such as fluororesin or polyethylene.

Figure 33A:
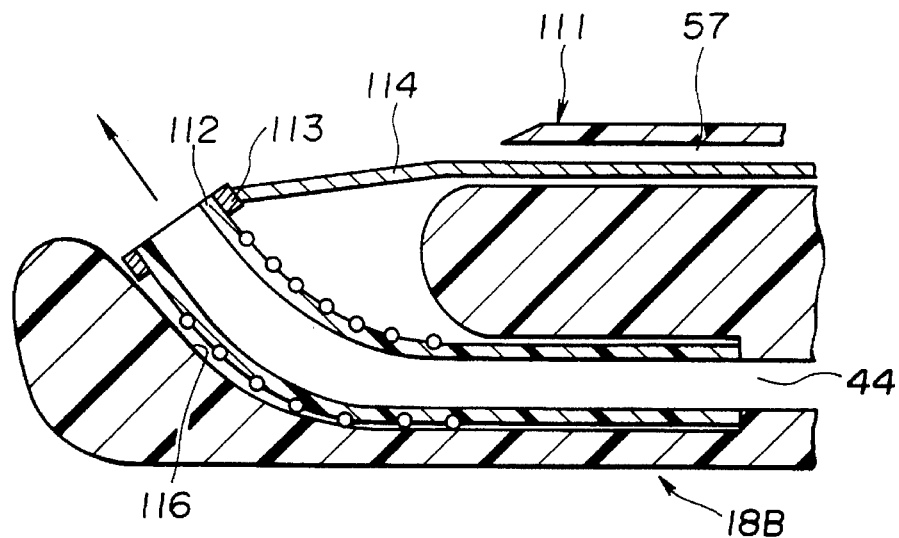
FIGS. 33(a) and 33(b) are is a sectional views of the front end of the insertion section covering portion related to the ninth embodiment.
Figure 33B:
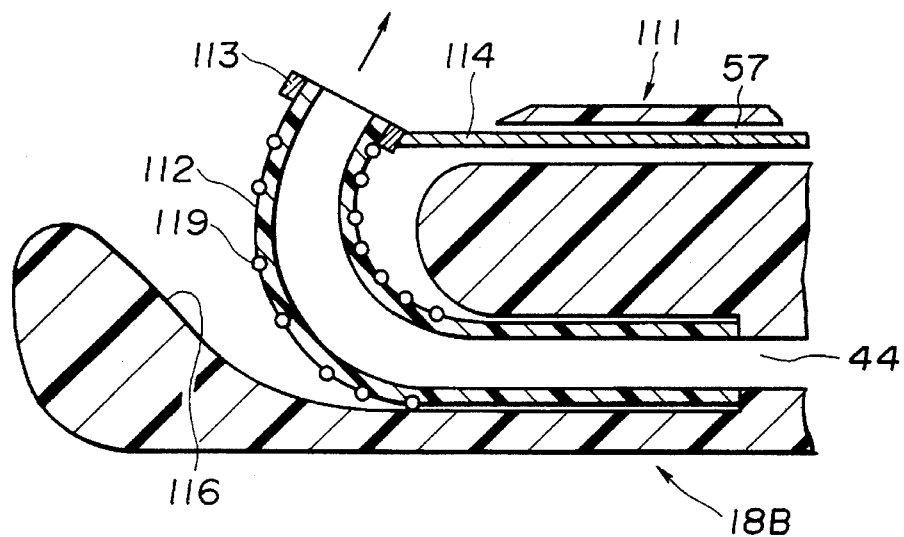
Figure 34:
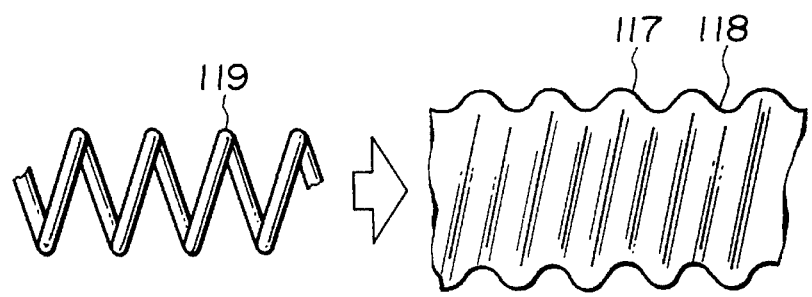
FIG. 34 is an explanatory drawing showing examples of the construction of the erecting tube which is employed in the erecting mechanism.

FIGS. 33 and 34 are related to the ninth embodiment of the present invention. FIG. 33 shows a tube body which is provided on the insertion section covering portion and reinforced and FIG. 33 (a) shows the time when the tube body is placed down. FIG. 33(b) shows the time when the tube body is erected. FIG. 34 shows an example of the erecting tube which is used in the erecting device.

The present embodiment has an insertion section covering portion 18B having a different direction changing means instead of the insertion section covering portion 18 of the second embodiment. Because the construction and the operation of the present embodiment are the same as the second embodiment, only different construction and operation will be described.

The insertion section covering portion 18B of the present embodiment has a front end cover component 111 instead of the front end cover component 31 shown in FIG. 9. The beginning end of an erecting tube 112 is bonded to the front end opening of the medical treatment instrument channel 44. A wire fixing member 113 is fixed to the front end of the erecting tube 112. The front end of an erecting wire 114 which pulls or pushes the erecting tube 112 is connected to the wire fixing member 113. The erecting wire 114 is connected to the medical treatment instrument erecting lever 37 provided at the mouth portion 33 via the wire introducing hole 57 provided in the front end cover component 111.

In the front end cover component 111, a slope surface 116 which curves the erecting tube 112 at 10°–40° with respect to the axis of the endoscope cover assembly is provided.

The erecting tube 112 is composed as follows.

The erecting tube 112 is made of a tube 117 shown in FIG. 34(a) which is formed of fluorine, polyethylene or polyolefine base resin such as PTFE and PFA. A spiral groove 118 is formed on the circumference of the tube 117 and a coil member 119 is wound along the bottom of the spiral groove 118 as shown in FIG. 34(b) so that the erecting tube 112 is formed as shown in FIG. 33. Meanwhile, it is permissible to form a thin elastic adhesive layer on the coil member 119 in order to strengthen the fitting between the coil member 119 and the tube 117 although the adhesive layer is not shown.

The spiral groove 118 and the coil member 119 are provided in the range in which the erecting tube 112 is curved when the erecting tube 112 is erected.

The operation of the erecting tube will be described below.

When an operator wants to control the direction of the protrusion of a medical treatment instrument using the medical treatment instrument erecting device provided at the front end of the endoscope cover assembly, he pulls the erecting wire 114 by operating the erecting tube driving device. Then, the wire fixing member 113 connected to the erecting wire 114 is pulled toward the wire introducing hole 57 and accompanied with this action, the erecting tube 112 is curved and erected.

Here, assume that a plain tube which contains no coil member 119 provided on the erecting tube 112 or groove is curved. If a tube which is unlikely to be curved is curved successively, a bending stress is concentrated to a certain point along the axis so that the tube is buckled at this point. The fact that a tube is buckled means the phenomenon in which the tube cannot maintain its circular sectional shape any more and then is crushed in one direction so that the crushed portions stretch in a direction perpendicular to that direction.

However, because the coil member 119 is wound on the circumference of the erecting tube 112 in the present embodiment, a force for deforming the erecting tube by concentration of bending stress is eliminated by means of the coil member 119, maintaining the sectional shape of the erecting tube to be circle. For this reason, even if the erecting tube is curved successively, the erecting tube 112 does not undergo crushing, so that it is possible to control a medical treatment instrument inserted through the erecting tube in a desired direction.

Figure 35A:
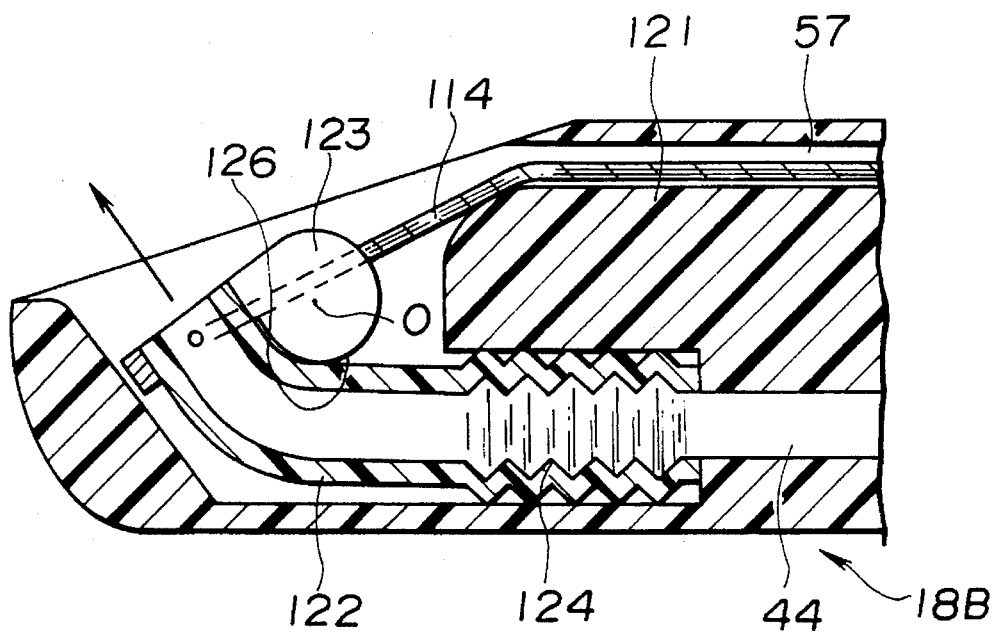
FIGS. 35(a) and 35(b) are is a sectional views of the front end of the insertion section covering portion in the modified example of the ninth embodiment.
Figure 35B:
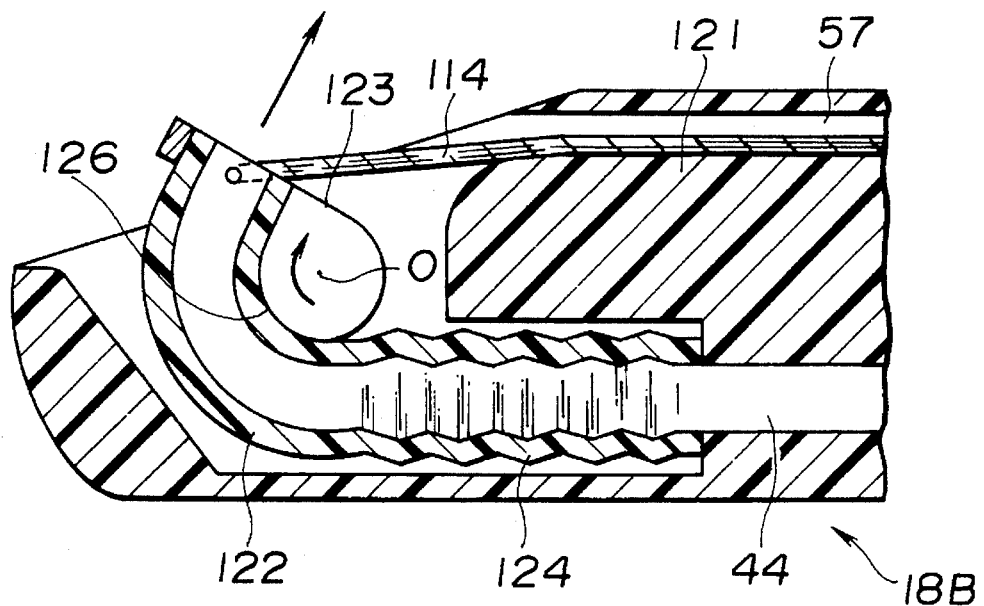

FIG. 35 shows a medical treatment instrument erecting device provided on the front end of the insertion section covering portion 18B in the modified example of the ninth embodiment. FIG. 35(a) shows the time when the erecting device is placed down and FIG. 35(b) shows the time when the erecting device is erected.

The insertion section covering portion 18B shown in FIG. 35 has an erecting device different from that shown in FIG. 33. The construction and the operation of the present embodiment are the same as the ninth embodiment, and thus only different points will be described while the same reference numerals are attached.

The insertion section covering portion 18B of the present modified example has a front end cover component 121 instead of the front end cover component 111 shown in FIG. 33. In the front end cover component 121, the beginning end of the erecting tube 122 is bonded to a front end opening of the medical treatment instrument channel 44 to communicate with the medical treatment instrument channel 44.

The front end of the erecting tube 122 is connected to a part of a rotating member 123 which is rotatable around the point 0 in FIG. 35. Bellow grooves 124 are formed on the rear end of the erecting tube 122. The erecting wire 114 is connected to the rotating member 123. A ring-like tube guide 126 is formed on the rotating member 123 to allow the erecting tube 122 to be wound therearound.

The operation of the present embodiment will be described below.

When an operator pulls the erecting wire 114, the rotating member 123 rotates with respect to the point 0. Accompanied by this action, the erecting tube 122 is extracted forward and wound around the tube guide 126 having a curved surface of a uniform curvature provided on the rear side of the rotating member 123.

A displacement of the extracted portion of the erecting tube 122 is absorbed by an elongation of the bellow grooves 124. If the erecting tube 122 is curved, because the tube 122 is wound around the tube guide 126 of the rotating member 123, no bending stress is concentrated on a single point. Bending stress is dissipated uniformly, and thus the tube 122 is not buckled, so that it is possible to control a medical treatment instrument in a desired direction and further perform operation for inserting and removing a medical treatment instrument under this condition.

It is permissible to use a construction in which the embodiments described above are combined.

FIGS. 36 and 37 are related to the tenth embodiment of the present invention. FIG. 9(a) is a perspective view showing the construction of the front end of the insertion section covering portion. FIG. 9(b) is a side sectional view of the insertion section covering portion. FIG. 37 is a longitudinal sectional view showing the construction of the front end cover component.

The present embodiment has an insertion section covering portion 18C containing a front end cover component 31C shown in FIG. 36 instead of the insertion section covering portion 18 of the second embodiment. The construction and the operation of the present embodiment are the same as the second embodiment, and thus only different points will be described while the same reference numerals are attached.

Figure 36A:
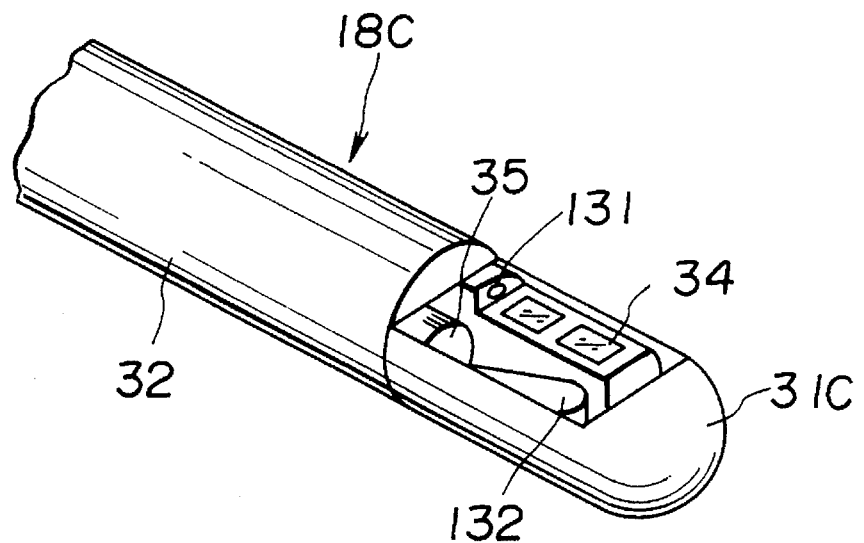
FIGS. 36(a) and 36(b) is a perspective view showing the construction of the front end of the insertion section covering portion related to the tenth embodiment.

As shown in FIG. 36(a), the front end cover component 31 of the insertion section covering portion 18C is made of hard resin and the like and the front end cover component 31C contains the observational opening 34 and the channel opening 35. In the observational opening 34, the transparent cover glass 43 and a water feeding nozzle 35 which communicates with the water feeding pipe 131 are disposed. The observational window and the illumination window of the endoscope inserted into the inside of the cover face the observational opening 34, thereby making it possible to irradiate light to an inspection portion and observe the inspection portion. By feeding water to the cover glass by means of the water feeding nozzle 35, it is possible to clean the cover glass 43 in order to secure the field of view.

In the front end cover component 31C, an erecting base 132 which constitutes an erecting device is provided in front of the channel opening 35.

Figure 36B:
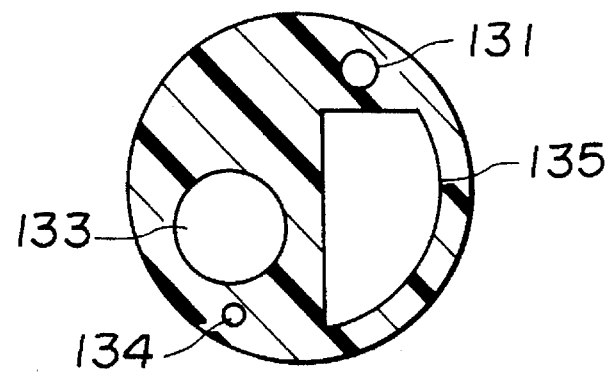

As shown in FIG. 36(b) showing a sectional view taken perpendicular to the longitudinal axis of the insertion section covering portion 18C, the insertion section covering portion 18C is made of a multi-lumen tube constituted of four lumens. A channel lumen 133 which is one of the four lumens is formed of a slippery material and communicates with the medical treatment instrument inserting port 36. In the channel lumen 133, it is permissible to make a teflon tube (not shown) run through the inside of the channel lumen 133.

Instead of the suction pipe 26, a pressurized fluid pipe 134 is provided below the channel lumen 133. An endoscope lumen 135 which runs through the endoscope insertion section is provided beside the channel lumen 133. The water feeding pipe 131 is provided above the endoscope lumen 135. The optical system provided on the front end of the endoscope insertion section is arranged just below the cover glass 43 (see FIG. 36(a)) provided on the front end of the endoscope lumen 135.

The pressurized fluid pipe 134 communicates with a fluid mouth metal (not shown) provided on the mouth portion 33.

Figure 37A:
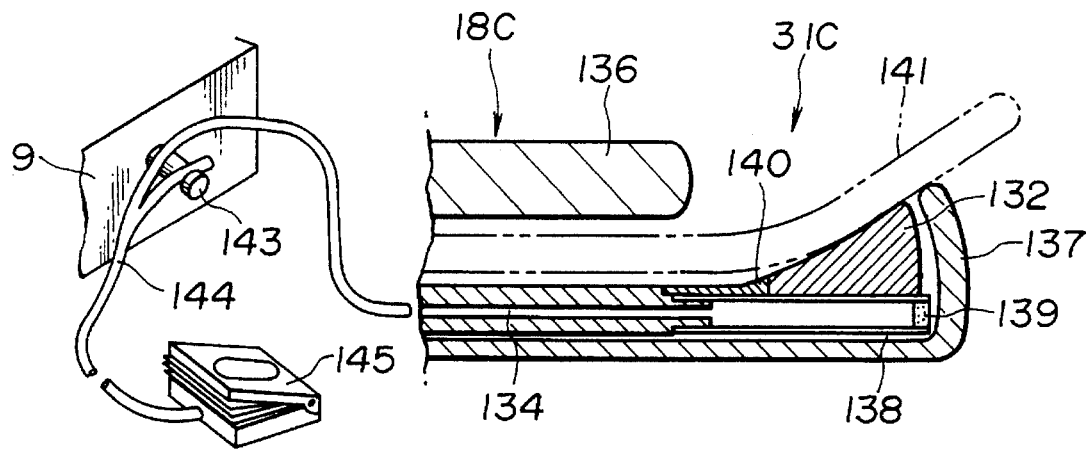
FIGS. 37(a) and 37(b) are sectional views showing the construction of the front end cover component.

The fluid control unit 9 contains a pressure control valve 143 shown in FIG. 37(a) for controlling the opening/closing of the pressure tube 144 which communicates with the fluid mouth metal of the mouth portion 33. A pressure control device 145 is connected to an end of the pressure tube 144. The pressure control device 145 is of foot pump type and adapted to supply fluid (for example, air) to the pressure tube 144 by operator's pressing it by the foot.

The pressure control device 145 may be constructed so as to be operated manually by a syringe which is connected to the fluid mouth metal as well as by the foot pump. Additionally, it is possible to use an electric pump for the pressure control device 145 as described later and perform the operation for giving instructions for driving the electric pump through switches provided on the operating unit.

As shown in FIG. 37(a) showing a sectional view taken along the longitudinal axis of the front end cover component 31C, the front end cover component 31C has a hard member 136 and an end cap 137. At the front end of the pressurized fluid pipe 134, a tube balloon 138 constituting an erecting device is installed just below the erecting base 132 and the end of the tube balloon is sealed by means of an air tight plug 139.

As shown in FIG. 37(a), the erecting base 132 is bonded to the hard member 136 via a thin portion 140 which is flexible to provide a cheap construction. The erecting base 132 may be rotatably fixed via a shaft so that it is erected.

Next, the operation of the tenth embodiment will be explained.

To perform medical treatment through the endoscope, an endoscope operator inserts a medical treatment instrument 141 from the medical treatment instrument inserting port 36, passes it through the channel lumen 133, the front end cover component 31C and the erecting base 132, and then makes the medical treatment instrument 141 protrude into the body cavity as shown in FIG. 37(a).

Figure 37B:
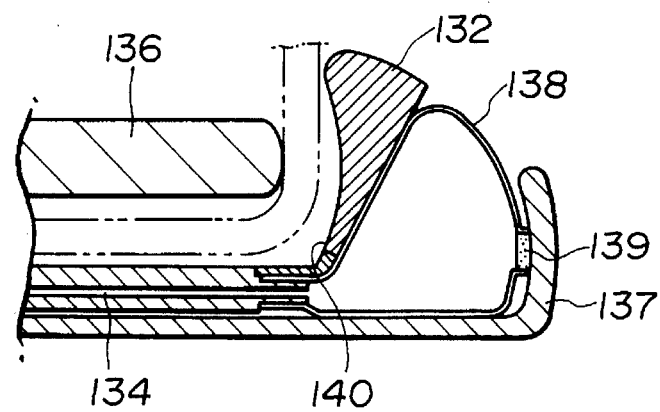

By pressing the control pressure device 145 by the foot to introduce the end of the medical treatment instrument to a desired treatment portion, pressurized fluid (for example, air) is fed through the pressure tube 144 and the pressurized fluid pipe 134 and the pressurized fluid expands the tube balloon 138 provided at the end as shown in FIG. 37(b). Due to this expansion, the thin portion 140 is bent so that the erecting base 132 above the tube balloon 138 is erected interlocking with the movement of the thin portion 140.

Thus, by employing the endoscope cover assembly having channels of the present embodiment, it is possible to provide a simpler means for introducing a medical treatment instrument as compared with the wire extraction type in which the erecting base is erected by pulling the wire and thus realize a cheap endoscope cover assembly having channels.

Next, a plurality of insertion section covering portions having different direction changing means and the cover-system endoscope which is selectively combined with the cover-type endoscope 4 will be described below.

Of the plurality of the insertion section covering sections, two types of the insertion section covering portions will be described below.

Figure 38A:
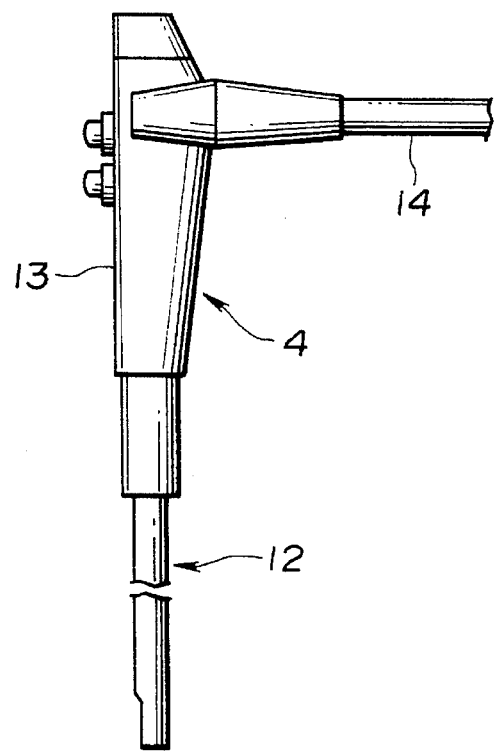
FIGS. 38(a), 38(b) and 38(c) are explanatory drawings related to combinations of the main body of the endoscope and a plurality of the insertion section covering portions.

In the two insertion section covering portions 18C, 18D shown in FIG. 38(a), the medical treatment instrument direction changing means are basically different and selectively used depending on a medical treatment instrument to be used and the purpose of use. The description of the same construction as the first, second and tenth embodiments is omitted while the same reference numerals are attached. The entire construction of the endoscope in the present embodiment is the same as that of the second embodiment.

Figure 38C:
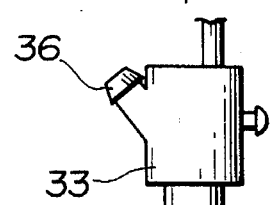
Figure 38C:
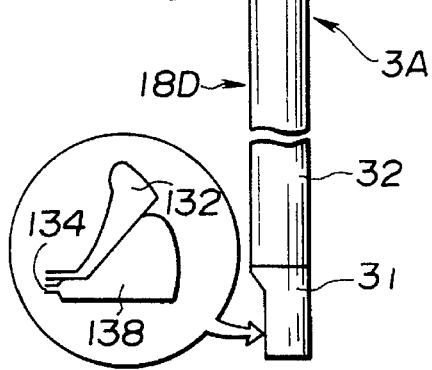
Figure 38B:
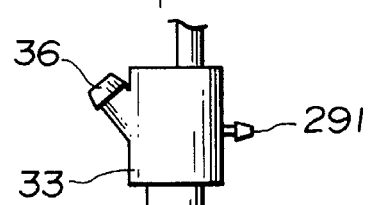
Figure 38B:
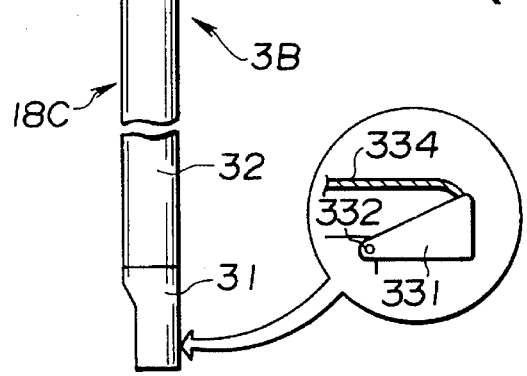

The first insertion section covering portion 18D has the same construction as shown in FIG. 37 and is provided with the tube balloon 138 which constitutes the direction changing means as shown in FIG. 38(b). The tube balloon 138 communicates with the pressure control device 145 through the fluid mouth metal 291 provided on the mouth portion 33 and the pressure tube 144.

In the second insertion section covering portion 18C, the front end cover component 31 is provided with the erecting device 325 which acts as the direction changing means shown in FIG. 5 like the first embodiment. The erecting device 325 has the erecting base 331 which is rotatably fixed via the rotating shaft 32 as shown in FIG. 38(c). The erecting base 331 is erected when the erecting wire 334 is pulled.

In the first insertion section covering portion 18C, a force for rising the erecting base 132 is small, however, it is sufficiently enough to erect a bile duct contrast tube which is one of the medical treatment instruments and frequently used. According to this construction, the number of the components of the erecting device is small and the erecting device is assembled easily. Thus, the production cost is low.

Additionally, the force for rising the erecting base 132 may be smaller and thus the sectional size of the pressurized fluid pipe may be reduced. Further, the sizes of the erecting base 132 and the tube balloon 138 can be reduced so that it is possible to construct a small size direction changing means.

For this reason, it is possible to reduce the diameter of the insertion section covering portion 18C and the size of the front end cover component 31. This type can be used in narrow cavities and is easy to operate for inserting the medical treatment instrument.

On the other hand, when a stone crushing basket requiring a greater erecting force, which is one of the medical treatment instrument, is used, the first insertion section covering portion 18D is used and the wire extraction type in which the erecting wire 334 is pulled is employed, thereby lowering the cost for entire endoscope inspection.

Figure 39A:
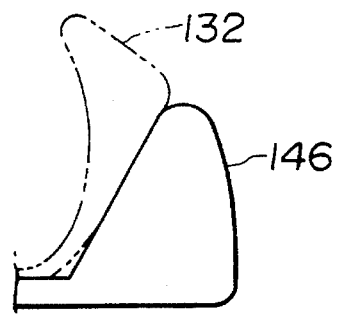
FIGS. 39(a) and 39(b) are a drawings showing the construction of a tube balloon related to the tenth embodiment.
Figure 39B:
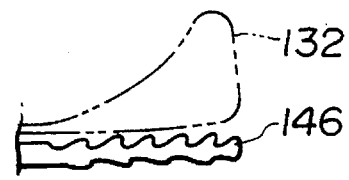

FIG. 39 shows the construction of the tube balloon related to the modified example of the tenth embodiment.

The modified example shown in FIG. 39(*a*) is a non-expansive balloon 146 the initial condition of which is formed so that the shape is expanded. According to this construction, when the balloon is contracted, it is crumpled as shown in FIG. 39(*b*). However, by pressurizing fluid, the shape is restored to its original shape shown in FIG. 39(*a*) so as to erect the erecting base 132. With such a balloon, the possibility that the balloon is broken because it is expanded too much is reduced as compared with an expansive balloon.

Figure 40A:
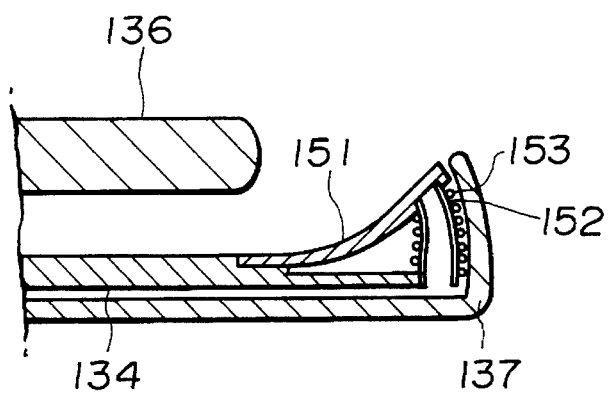
FIGS. 40(a) and 40(b) are sectional views showing the construction of the front end cover component related to the eleventh embodiment.
Figure 40B:
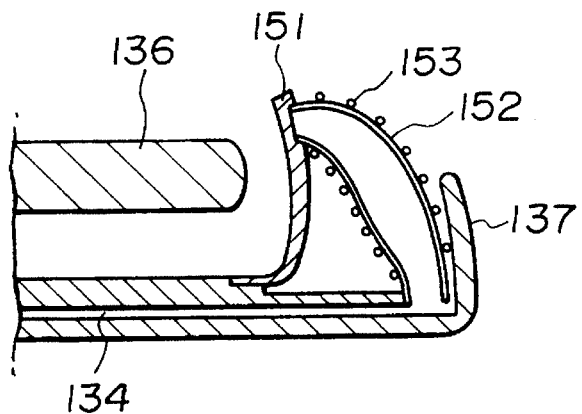

Next, the eleventh embodiment will be described. FIG. 40 is a sectional view showing the construction of the front end cover component related to the eleventh embodiment of the present invention. The eleventh embodiment has almost the same construction as the tenth embodiment. Thus, only different construction will be explained and the description of the entire construction is omitted while the same reference numerals are attached to the same construction.

In the front end cover component of the eleventh embodiment, as shown in FIG. 40, an erecting base 151 which is thin and flexible is provided on the hard member 136. A tube balloon 152 is connected air-tightly below the erecting base 151. One opening of the tube balloon 152 is connected to the opening of the pressurized fluid pipe 134 air-tightly. Further, a coil 153 is provided on the circumference of the tube balloon 152. It is permissible to construct the coil 153 by building a plurality of rings instead of spring type. The other construction is the same as the tenth embodiment.

As regards the operation of the eleventh embodiment which is constructed as described above, when fluid is pressurized via the pressurized fluid pipe 134, the tube balloon 152 is expanded to erect the erecting base 151. At this time, the coil 153 restricts the expansion along the circumference of the balloon 152 and thus the tube balloon 152 is not expanded along the circumference so much and instead, the tube balloon 152 is expanded along the axis, erecting the erecting base 151.

In the eleventh embodiment, it is possible to expand the balloon only in a target direction. Thus the quantity of the pressurized fluid can be reduced to obtain a desired erecting angle and further, the response of the balloon can be improved. The operation and the effect of this embodiment are the same as the tenth embodiment.

When the erecting base is erected by means of the balloon shown in the tenth embodiment, if operating fluid is a pressurized fluid, some operation for pressurizing certain quantity of fluid may be sometimes required in the pressure control device 145 in order to obtain a pressure required for starting the erection of the erecting base. This problem can be solved by providing the pressure control device with a mechanism for giving preliminary pressure to the pressure control device regardless of whether the pressure control device is of foot type, manual type or electric type. By providing this mechanism, it is possible to secure an operation having an excellent response even if a compressible fluid is used.

Figure 41:
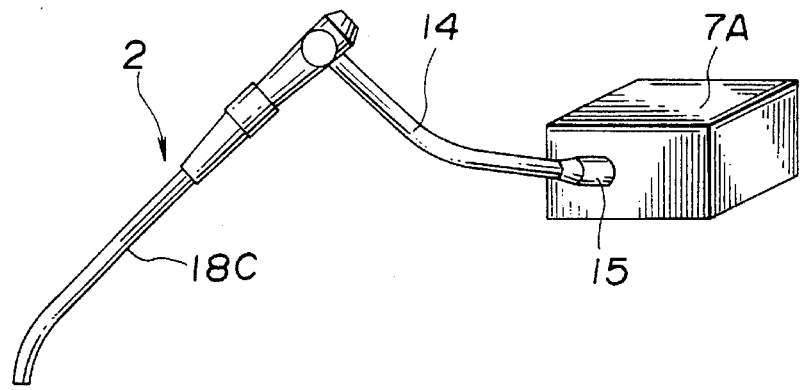
FIG. 41 is a drawing showing the cover-system endoscope according to the twelfth embodiment connected to a light source unit.

Next, the twelfth embodiment will be described with reference to FIGS. 41 and 42. The endoscope of the present embodiment has a light source shown in FIG. 41 instead of the light source shown in FIG. 8. The cover-system endoscope 2 is connected to the light source unit 7A through the universal cord 14 and the connector 15 for use. The cover-system endoscope 2 has the insertion section covering portion 18C as shown in FIG. 37. The description of the same construction and the operation as the tenth embodiment is omitted while the same reference numerals are attached.

Figure 42:
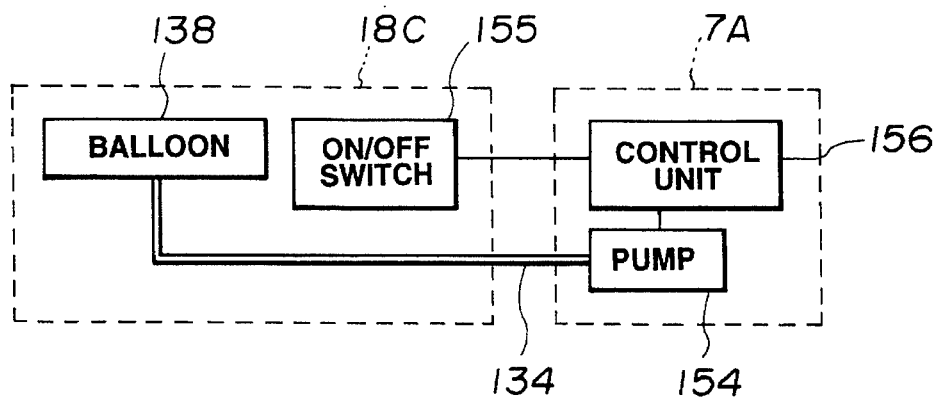
FIG. 42 is a diagram showing the balloon and the light source unit connected.

For this reason, as shown in FIG. 42, an air feeding pump 154 is provided within the light source unit 7A to expand the tube balloon 138 for erecting the erecting base 132 which is contained in the insertion section covering portion 18C. The air feeding pump 154 communicates with the tube balloon 138 via the fluid pressure device 134.

The insertion section covering portion 18C is equipped with an ON/OFF switch for starting and stopping the pump 154. A control unit 156 which is disposed in the light source unit 7A controls the start and stop of the air feeding pump 154 by means of signals dispatched from the switch 155.

According to the present embodiment, in the light source unit 7A, a pump 154 is provided to expand the balloon 138 for driving the erecting base 132 of the insertion section covering portion 18C and when the insertion section covering portion is connected to the light source unit, the pressurized fluid pipe which extends to the balloon is also connected to the pump in the light source unit. Thus, according to the present embodiment, by operating the ON/OFF switch 155 provided on the insertion section covering portion 18C, it is possible to expand the balloon 138 to erect a medical treatment instrument easily.

Figure 43:
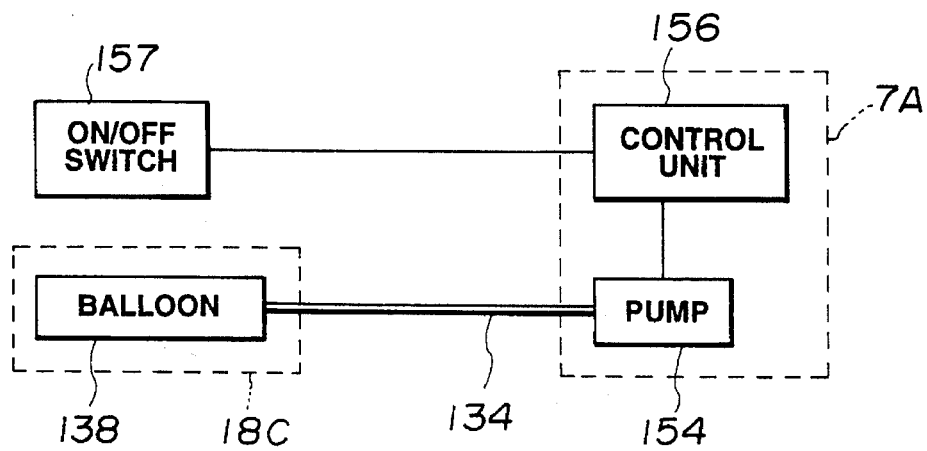
FIG. 43 is a diagram showing another connection of the balloon and the light source unit.

FIG. 43 shows a modified example of the twelfth embodiment.

Instead of the switch 155 which is provided integratedly on the insertion section covering portion 18C to start and stop the air feeding pump 154 as shown in FIG. 43, a dedicated switch 157 such as a foot switch is provided separately.

It is permissible to use the air feeding pump incorporated in the fluid control unit 9 instead of it that the air feeding pump 154 is provided within the light source unit 7A.

Figure 44:
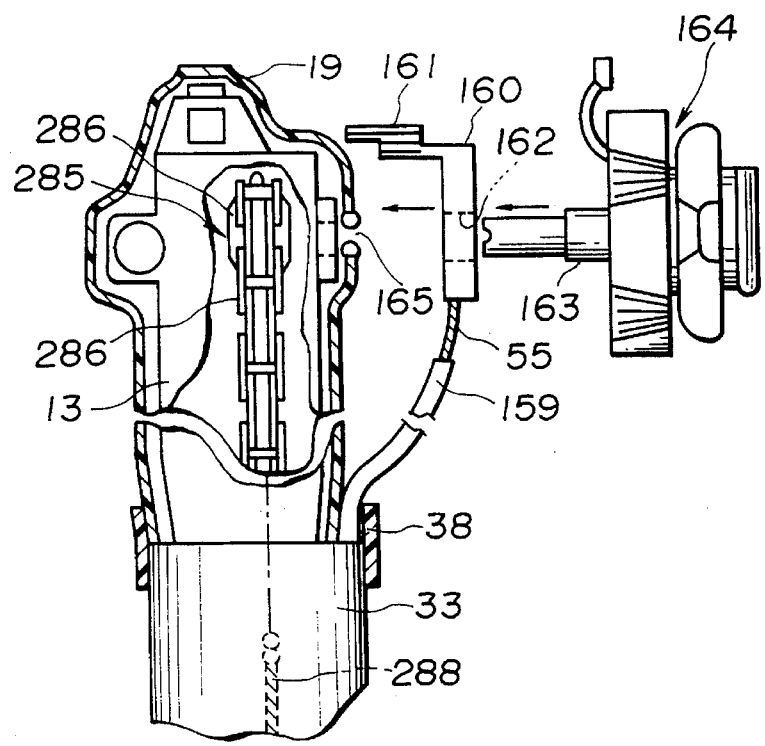
FIG. 44 is a drawing showing the construction of the erection control unit according to the thirteenth embodiment.

FIG. 44 is related to the thirteenth embodiment, showing the construction of the erection control unit.

The cover-system endoscope of the present embodiment employs an erection control unit which is provided coaxially with a curve operating knob provided within the endoscope 4 instead of the medical treatment instrument erecting lever 37 of the second embodiment. The description of the same construction and operation as the second embodiment is omitted while the same reference numerals are attached and only different points will be described below.

From the side of the beginning end of the mouth portion 33 of the insertion section covering portion 18, the wire tube 159 which runs through the wire introducing hole 57 extends and the erecting wire 55 extends from the wire tube 159.

The beginning end of the erecting wire is connected to the erection control knob 160 which acts as a driving means. The erection control knob 160 comprises a finger lever 161 which protrudes from the main body which is formed, for example, in a circular shape and a hole provided in the center of the main body.

On the other hand, a curve/erection control center shaft 163 which protrudes from the curve control knob 164 is mounted on the side of the operating unit 13 of the endoscope 4. As shown in FIG. 44, the curve/erection control center shaft 163 is connected to a curve control mechanism 285.

The curve control mechanism 285 has a sprocket 286 with which the center shaft 163 of the curve control knob 164 is engaged or threadedly engaged. A chain 287 is set in the sprocket 286. The chain 287 extends from the operating unit to the portion in which the operating unit is connected to the endoscope insertion section 12 and the beginning end of the curve control wire 288 is connected to the final end of the chain 287. The curve control wire 288 is connected to a curve top of a curving section (not shown).

When the curve control knob 164 is operated, the sprocket 286 is rotated and interlocking with the rotation of the sprocket 286, the chain 287 and the curve control wire 288 are pulled or pushed. Consequently, the curving section of the endoscope 4 is operated.

The curve/erection control center shaft 163 is rotatably engaged with the hole 162 of the erection control knob 160 and the hole 162 is disposed between the curve control knob 164 and the operating unit 13. After the control center shaft 163 which protrudes from the curve control knob 164 is inserted through the hole 162 in the erection control knob 160, the shaft 163 is inserted into the operating unit 13 through the shaft mounting hole in the operating unit covering portion 19.

The construction and the operation of this embodiment are the same as the thirteenth embodiment and thus the description and the drawing of the same construction are omitted while the same reference numerals are attached.

With the construction described above, the insertion section covering portion 18 and the operating unit covering portion 19 are mounted on the cover-type endoscope 4. The wire tube 159 which extends from the mouth portion 33, the erecting wire 55 and the erection control knob 160 are located on the side having the shaft mounting hole 165 of the operating unit 13. The curve/erection control center shaft 53 of the curve control knob 164 is inserted through the hole 162 in the erection control knob 160, further inserted through the shaft mounting hole 165 and then connected to the curve control mechanism. Consequently, by rotating the erection control knob 160 around the curve/erection control center shaft 163, the erecting wire can be pulled or pushed, so that the erecting tube 52 is erected and placed down respectively.

Because the curve/erection control center shaft 163 is provided on the curve control knob 164 side, the operating unit cover 19 is easy to mount on the operating unit 13. Additionally, because the erection control knob 160 is detachable, it is easy to mount and remove the cover.

In this embodiment, the erecting mechanism is not restricted to the erecting tube 52 and it is permissible to use an erecting mechanism of the other embodiment.

According to the present embodiment, the erection control device is rotatably mounted through the curve control knob 164 of the endoscope control unit 13, and thus the same erecting operability can be obtained. The erection control knob 160 can be removed easily so that it is possible to throw away the erecting wire and the erection control knob 160 together with the cover.

Additionally, because the position for curve operation is very near the position for erection control, it is easy to switch the two operation.

Further, the present embodiment allows existing curve shafts on which the curve control knob is mounted to be used and the construction is simple, thereby reducing the cost for parts and assembly.

FIG. 45 shows the construction of the erection control device related to the fourteenth embodiment.

The erection control device of the present embodiment is different from the thirteenth embodiment and the curve/erection control center shaft 169 protrudes to the operating unit 13 side.

Figure 45A:
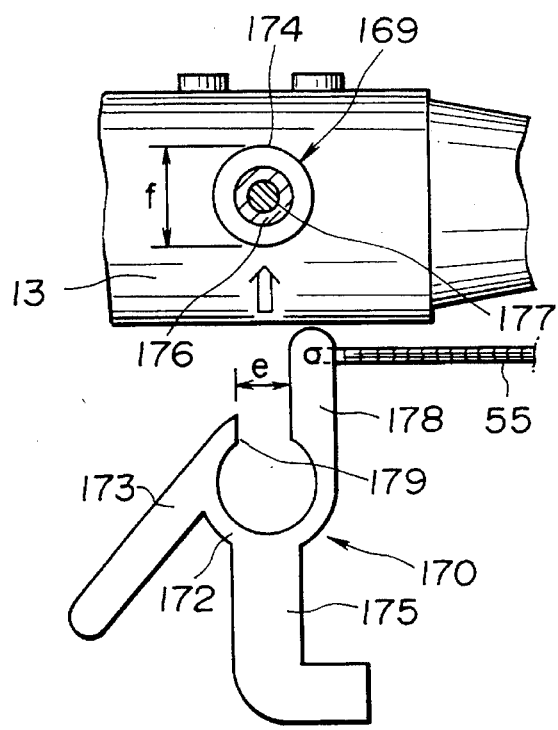
FIGS. 45(a) and 45(b) are is related to the fourteenth embodiment.

As shown in FIG. 45(a), the present embodiment contains a medical treatment instrument erecting lever 170 instead of the erection control knob 160. In the present embodiment, the curve/erection control center shaft 169 comprises a center shaft and a plurality of ring-like shafts which are concentric with the center shaft in order to control curving up/down and to the right and left and control erection. A ring-like fixing shaft 174 is fixed around the curve/erection control center shaft 169. Inside the fixing shaft 174, the up/down curve/erection control center shaft 176 and the right/left curve/erection control center shaft 177 are rotatably provided. A up/down curve control knob and a right/left curve control knob (not shown) are fixed to the shafts 176 and 177. Meanwhile, the up-down/right-left curve control knob may be fixed or detachable.

As shown in FIG. 45(a), the medical treatment instrument erecting lever 170 is formed to have three arms extending from a C-ring shaped center in which a fixing groove 179 allowing the medical treatment instrument erecting lever 170 to be mounted from the side of the fixing shaft 174. The medical treatment instrument erecting lever 170 comprises the arm 178, a main lever 175 which extends almost parallel to and opposite to the arm 178 and an auxiliary lever 173 which extends obliquely with respect to the main lever with a hinge section 172 interposed. The operator's end of the erecting wire 55 is fixed near the front end of the arm 178 of the medical treatment instrument erecting lever 170.

The entrance width e of the fixing groove 179 is smaller than the outside diameter f of the fixing shaft 174 and when the medical treatment instrument erecting lever 170 is mounted, the fixing groove 179 is elastically opened. Thus, once the medical treatment instrument erecting lever 170 is mounted, it cannot be removed from the fixing shaft 174 until the fixing groove is forcibly opened.

The construction and the operation of this embodiment are the same as the thirteenth embodiment, and thus the description and the entire construction are omitted while the same reference numerals are attached.

With the construction described above, after the insertion section covering portion 18 is mounted on the cover-type endoscope 4, the medical treatment instrument erecting lever 170 is attached to the fixing shaft 174. After that, the operating unit covering portion 19 is placed over entirely the operating unit 13. When the cover 3 is mounted on the cover-type endoscope 4, after required inspections are finished, the operating unit covering portion 19 is removed and then the medical treatment instrument erecting lever 170 is removed from the fixing shaft 174. At this time, if the main lever 175 and the auxiliary lever 173 are gripped, the fixing groove 179 is expanded so that it is possible to remove the medical treatment instrument erecting lever 170 from the shaft 174. After that, the insertion section covering portion 18 is removed from the cover-type endoscope 4 and thrown out.

Because the erecting wire 55 is integrated with the medical treatment instrument erecting lever 170 in the present embodiment, it is possible to throw away the endoscope cover assembly 3 and the medical treatment instrument erecting lever 170 together, thereby always keeping the operating unit 13 clean. For this reason, it is unnecessary to clean and disinfect the operating unit 13.

The medical treatment instrument erecting lever 170 of the present embodiment can be fit or removed easily from the side of the fixing shaft 174 even if the curve control knob is not detachable. Thus, it is possible to prepare for fitting the endoscope cover assembly before use, remove it after use and throw it out easily. The construction and the operation of the present embodiment are the same as the thirteenth embodiment and thus the description of them is omitted.

In the present embodiment, it is permissible to construct the erecting wire 55 and the medical treatment instrument erecting lever 170 so that they are detachable.

Figure 45B:
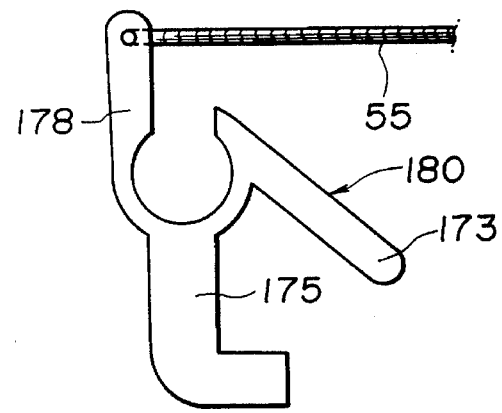

FIG. 45(b) shows a medical treatment instrument erecting lever 180 related to the modified example of the fourteenth embodiment. In the medical treatment instrument erecting lever 180, the arm 178 and the auxiliary lever 175 are disposed on a side opposite to those of FIG. 45(a). The construction and the operation of the present embodiment are the same as the fourteenth embodiment and thus the description of them is omitted.

Figure 46A:
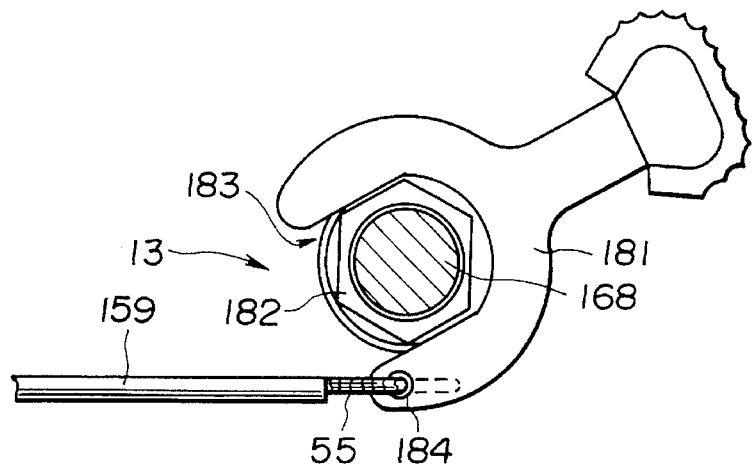
Figure 46B:
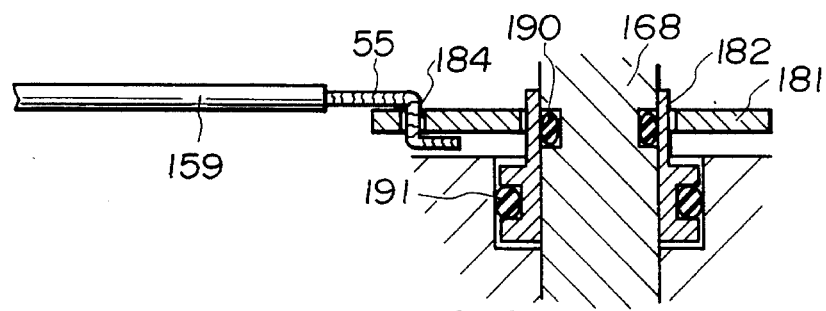
FIG. 46(b) is a sectional view of the erection control unit.

FIG. 46 is related to the fifteenth embodiment of the present invention. FIG. 46(a) is a top view of the erection control device and FIG. 46(b) is a sectional view of the erection control device.

In the fifteenth embodiment, instead of the curve/erection control center shaft 163, a curve control center shaft and an erection control center shaft are rotatably disposed separately. Additionally, instead of the erection control knob 160, a medical treatment instrument erecting knob 181 is provided as shown in FIG. 46(a).

As shown in FIG. 46(b), the separated shafts described above comprise a curve control center shaft 168 which is connected to a curving mechanism (not shown) and a ring-like erection control center shaft 182 which is slidably disposed around the curve control center shaft 168.

The description of the same construction and operation as the thirteenth embodiment is omitted while the same reference numerals are attached.

According to the present embodiment, one or more flat surfaces (hexagon in FIG. 46(a)) are formed on part of the circumference of the erection control center shaft 182 on which the erection control knob 181 is detachably mounted.

As shown in FIG. 46(b) showing a sectional view taken along the axis of the shaft, the erection control center shaft 182 is slidably mounted on the curve control center shaft 168. 0-rings 190, 191 are located between the shafts 168 and 182 and between the erection control center shaft 182 and the operating unit 13 so as to maintain water tightness from outside and cause a certain level of sliding resistance.

The erection control knob 181 has an arm for rotating the knob and on one end of the arm, a jaw in which a cutout 183 is formed is provided. The cutout 183 of the erection control knob 181 has flat surfaces which correspond to the flat surfaces of the erection control center shaft 182 and then is engaged therewith to prevent the knob from being rotated.

The erecting wire 55 is inserted into a wire fixing hole 184 disposed near the front end of one piece of the jaw of the erection control knob 181 and bent toward the shaft 168 to be connected to the erection control knob 181.

In the present embodiment also, a curve control knob (not shown) is fixed to the curve control center shaft 168.

With the construction described above, when the erection control knob 181 is engaged with the erection control center shaft 182 and the erection control knob 181 is turned, the erection control center shaft is rotated together. Because the erection control center shaft 182 is given a certain level of sliding resistance against the curve control center shaft 168 and the operating unit 13, even if the fingers are released from the erection control knob 181 during erection control, it is possible to maintain the position of the knob.

According to the present embodiment, the erection knob can be fit and removed easily and due to the sliding resistance caused around the knob, it is possible to operate the endoscope as easily as conventional endoscope systems. According to the present embodiment, the knob position is maintained even if the fingers are released from the knob during erection control. The operability of the present embodiment is the same as the thirteenth embodiment.

According to the present embodiment, the erecting wire 55 is fixed to the erection control knob 181 in the shape of a crank, so that the pulling strength of the wire 55 is increased and the wire 55 is more difficult to remove than the construction in which the wire 55 is folded back.

Further, if the erecting wire 55 is fixed in the shape of the letter Z as shown in FIG. 46(c), the pulling strength is further increased.

Figure 47A:
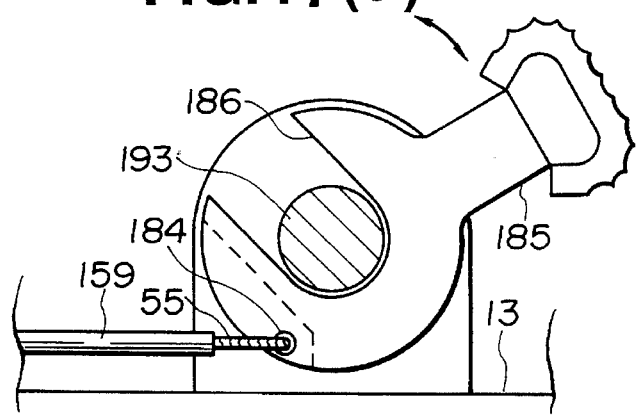
FIGS. 47(a) and 47(b) are related to the sixteenth embodiment.
Figure 47B:
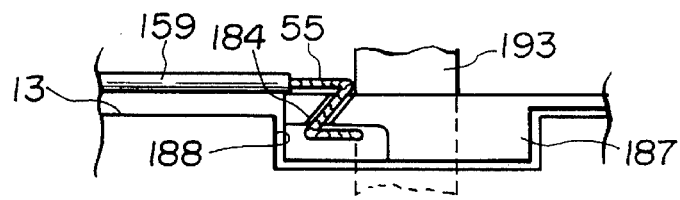

FIG. 47 is related to the sixteenth embodiment of the present invention. FIG. 47(a) is a top view of the erection control device and FIG. 47(b) is a side view of (a).

The present embodiment contains an erection control knob 185 instead of the erection control knob 181 of the fifteenth embodiment and further a curve/erection control center shaft 193 instead of the shafts 168, 182. The erection control knob 185 has an arm and a jaw like the knob 181. One end of the cutout 186 in the jaw is open and the other end is formed in the shape of a semicircle so as to rotatably engage with the shaft 168. In the erection control knob 185, as shown in FIG. 47(b), a protruded section 187 is formed on the jaw except a portion to which the erecting wire 55 is connected. In the operating unit 13, a groove 188 with which the protruded section 187 of the erection control knob 185 is engaged is formed around the curve/erection control center shaft 193. The groove 188 is formed so that one end is open and the other end is in the shape of a semicircle. A curve control knob (not shown) is fixed to the curve/erection control center shaft 193.

According to the construction described above, by sliding the erection control knob 185 with the opening of the cutout 186 of the erection control knob 185 facing the opening of the groove 188 of the operating unit 13, the erection control knob 185 is removed from the curve/erection control center shaft 193. If the erection control knob 185 is mounted on the curve/erection control center shaft 193 by sliding and then the erection control knob 185 is turned around the curve/erection control center shaft 193, the knob 185 becomes unremovable from the shaft 193.

If the erection control knob 185 is mounted on the curve/erection control center shaft 193 and then the erection control knob 185 is turned around the center shaft 193, the knob 185 becomes unremovable from the shaft 193. By turning the knob 185 counterclockwise from the state shown in FIG. 47(a), the erecting wire 55 is pulled so that the medical treatment instrument erecting base is erected. If the knob is reversed, the medical treatment instrument erecting base returns to its original position.

According to the present embodiment, although the erecting knob can be attached or detached easily, it does not get loose. The construction, the operation and the effect of this embodiment are the same as the first embodiment and thus the description of them is omitted.

Figure 48:
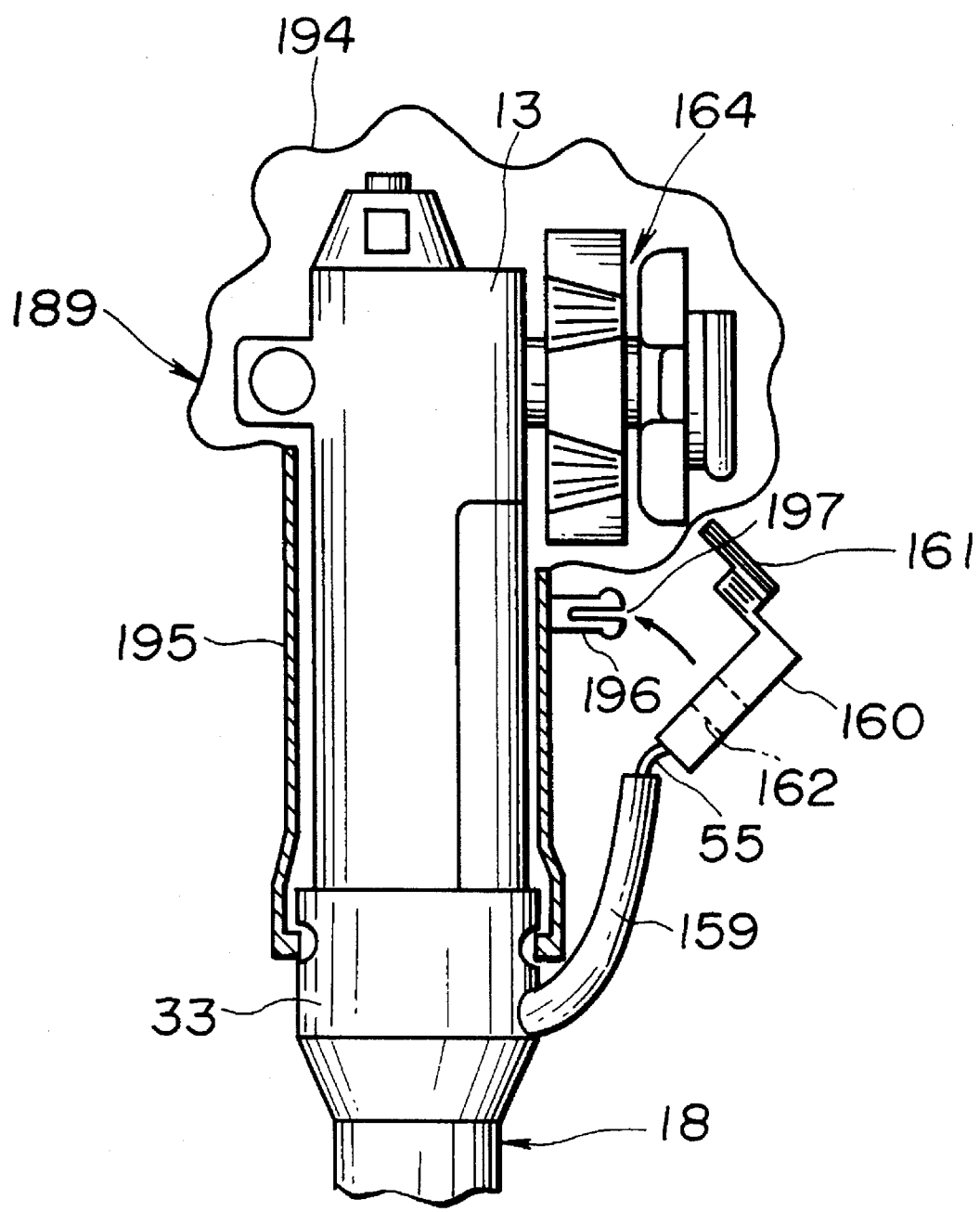
FIG. 48 is a drawing showing the construction of a medical treatment instrument erection control unit according to the seventeenth embodiment.

FIG. 48 is a construction drawing of the medical treatment instrument erection control device related to the seventeenth embodiment of the present invention.

According to the construction of the present embodiment, different from the thirteenth embodiment, the erection control knob is not mounted on the operating unit 13 but mounted on the operating unit covering portion 189. The description of the same construction and operation as the first embodiment is omitted while the same reference numerals are attached.

The operating unit covering portion 189 comprises a soft covering portion 194 and a hard covering portion 195 the end of which is engaged with the mouth portion 33 and which is connected to the soft covering portion 194. On the side of the hard covering portion 195, an erection control center shaft 196 is provided. A slit 197 is formed on the front end of the erection control center shaft 196. The diameter of the erection control center shaft 196 is relatively larger than that of a hole 162 in the erection control knob 160. The erection control center shaft 196 is located near the curve control knob 164. Meanwhile, the operating unit covering portion 189 may be reusable or semi-disposable.

According to the construction described above, the erection control center shaft 196 is engaged with the hole 162 in the erection control knob 160.

Although the diameter of the front end of the erection control center shaft 196 is larger than that of the hole 162, the diameter of the erection control center shaft 196 can be elastically reduced because the slit 197 is provided. Thus, after the erection control center shaft 196 is engaged with the hole 162 by forcing the hole 162 onto the erection control center shaft 196, the erection control knob 160 does not get loose even if the erection control knob 160 is turned around the erection control center shaft 196. The knob 160 can be removed only when it is pulled along the axis.

According to the present embodiment, because the erection control center shaft is provided on the operating unit covering portion, the knob can be fit or removed easily. Additionally, the erection control knob is disposed outside the operating unit covering portion, the knob can be operated more easily than the type in which the knob is covered with a cover. Further, according to the present embodiment, the erection control knob is disposed near the curve control knob, and thus the operability is almost the same as in conventional types.

Figure 49A:
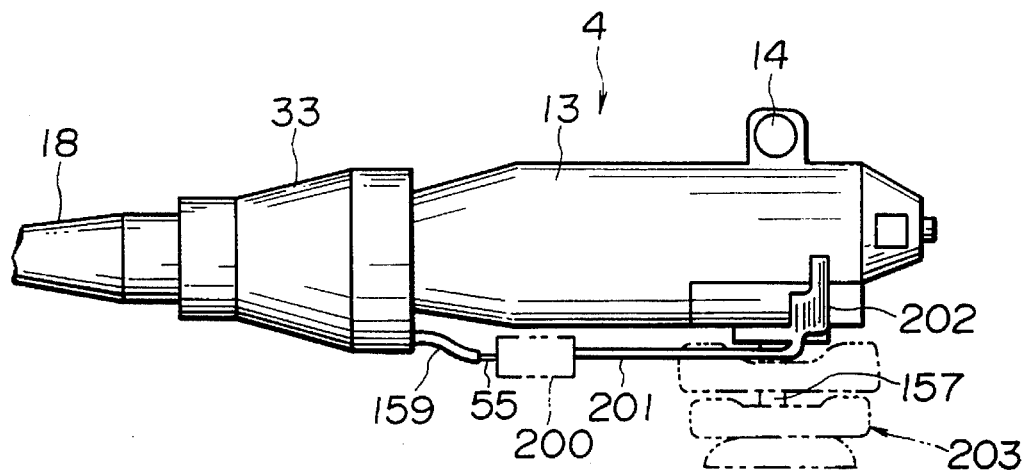
FIGS. 49(a) and 49(b) are side views showing the portion in which the rear end of the wire is connected to an erection control knob, according to the eighteenth embodiment.
Figure 49B:
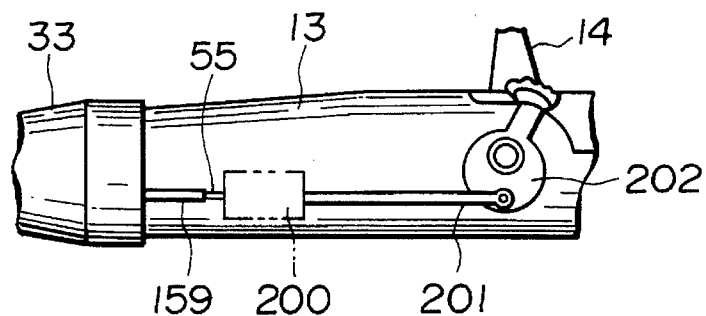
Figure 50:
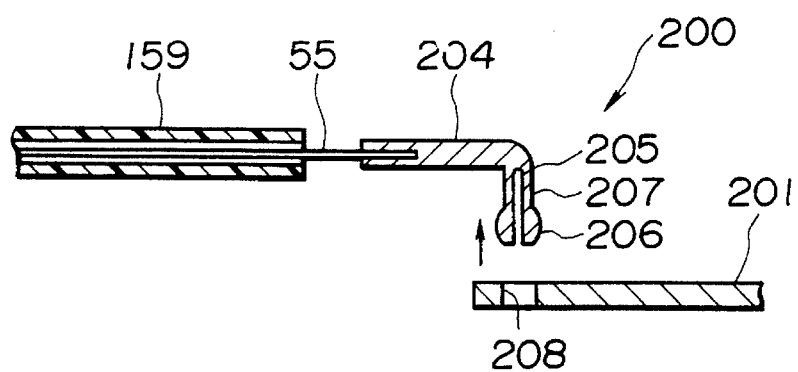
FIG. 50 is a sectional view showing the construction of the connecting portion.

FIGS. 49 and 50 are related to the eighteenth embodiment of the present invention. FIG. 49 is a side view showing a connecting portion in which the rear end of the wire is connected to the erection control knob and FIG. 50 is a sectional view showing the construction of that connecting portion.

Different from the thirteenth–seventeenth embodiments, the cover-system endoscope of the eighteenth embodiment contains the connecting portion which is interposed between the erecting wire and the erection control knob. The description of the same construction and operation as the thirteenth embodiment is omitted while the same reference numerals are attached and only different points will be described below.

FIGS. 49(a), (b) show the operating unit 13 of the cover-type endoscope which is inserted into the insertion section covering portion 18. FIG. 49(b) is a side view of FIG. 49(a) (viewed from below in these drawings, with the curve control knob removed).

The wire tube 159 extends backward from the mouth portion 33 of the insertion section covering portion 18. The erecting wire 55 runs through the wire tube 159.

The operator's end of the erecting wire 55 comes out from the wire tube 159 and is connected to the connecting wire through the connecting portion 200 and further the connecting wire 201 is connected to an erection control knob (hereinafter referred to as an erecting knob) 202 which erects and places down the aforementioned erecting device. The erection control knob 202 is provided on the operating unit 13 so that the knob protrudes and mounted on the curve control shaft 157 with which the curve control knob 203 is detachably engaged. The erection control knob 202 is rotatably provided concentrically with the curve control knob 203. The erection control knob 202 is located between the curve control knob 203 and the endoscope operating unit 13.

In the mouth portion 33, a position in which the wire 55 comes out is determined so that the beginning end of the erecting wire 55 is located on the side of the shaft 157 when the mouth portion 33 is fixed on the operating unit 13 (when a cover is mounted). The erecting wire 55 is positioned so that it runs along the wall of the operating unit 13.

Although the wire tube 159 is slightly slack inside the insertion section covering portion 18, the wire tube 159 is positioned at least at the front end cover component 31 and the mouth portion 33.

According to the present embodiment, the erecting wire is connected to a connecting member 204 near the operator's end and the connecting member 204 is attachable and detachable to/from the connecting wire 201 which is located on the cover-type endoscope 4 (see FIGS. 49 and 50).

FIG. 50 shows the construction of the connecting portion 200 shown by a two-dot chain line in FIG. 49.

The connecting member 204 which constitutes the connecting portion 200 is connected to the rear end of the erecting wire 55. The connecting member may be connected by soldering, caulking or welding. The other end of the connecting member 204 is bent and the end of the bent portion has a slot 205. The connecting member 204 comprises a large-diameter portion 206 which is located at the top and a small-diameter portion 207 which follows the top. On the other hand, a hole 208 is provided near the connecting end of the connecting wire 201. The diameter of this hole is smaller than that of the large-diameter portion 206 of the connecting member 204 but larger than that of the small-diameter portion 207.

Next, the operation of the present embodiment will be described below.

After the mouth portion 33 is fixed to the operating unit 13 of the cover-type endoscope 4, the large-diameter portion 206 and the small-diameter portion 207 of the connecting member 204 is fit into the hole 208 of the connecting wire 201. Although the diameter of the large-diameter portion 206 is larger than the hole 208, the diameter is elastically reduced by the slot 205 so as to allow the large-diameter portion 206 to enter through the hole 208.

Consequently, the erecting wire 55 is connected to the erection control knob 202 through the connecting wire 201 and by turning the erection control knob 202, the erecting wire 55 is pulled or pushed so as to erect and place down the erecting device at the front end of the insertion section. As for the procedure for inspection, after the insertion section covering portion 18 is mounted on the cover-type endoscope 4, the erecting wire 55 is connected to the connecting wire 201 and then the operating unit covering portion 19 is placed thereon. After that, a covered endoscope is inserted into the human body for inspection. If the inspection is finished, the endoscope is pulled out of the human body, the operating unit covering portion 19 is removed, the erecting wire 55 is disconnected, the insertion section covering portion 18 is removed and then those covers are thrown out.

Because, according to the present embodiment, no erection control device is provided on an endoscope cover assembly 3 which will be disposed, the erecting wire 55 is connected to the erection control device of the cover-type endoscope via the connecting portion. For this reason, the construction of the insertion section covering portion 18 is simple requiring not so high cost. Further, according to this embodiment, it is possible to realize as high an operability as conventional endoscopes.

Next, the nineteenth embodiment of the present invention will be described with reference to FIG. 51.

Different from the eighteenth embodiment, the nineteenth embodiment of the present invention has an adjusting means. The construction and the operation are the same as the eighteenth embodiment and thus only different points will be described while the same reference numerals are attached.

The erecting knob 209 which can rotate around the curve control shaft 157 has a connecting piece 210. The connecting piece 210 is provided with a slot 211 on the side of the end as shown in FIG. 51(b). In the slot 211, a small-diameter portion 220 which is located at the end and a large-diameter portion which follows the small-diameter portion are formed.

A connecting member 223 which is an adjusting means containing a plurality of spherical protrusions 222 is attached to the operator's end of the erecting wire 55. Indentations 224 having a smaller diameter than the protrusion 222 are provided between a plurality of the protrusions 222.

The slot 211 of the connecting piece 210 is formed so that the diameter of the small-diameter portion 220 is smaller than the outside diameter of the indentation 224 of the connecting member 223 and the diameter of the large-diameter portion 221 is smaller than the outside diameter of the protrusion 222.

Next, the operation of the present embodiment will be described.

Figure 51A:
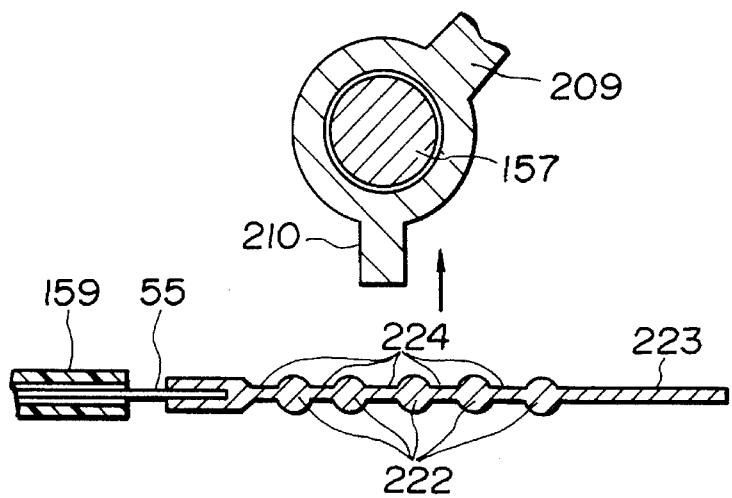
FIGS. 51(a) and 51(b) are drawings showing the construction of the connecting portion according to the nineteenth embodiment.
Figure 51B:
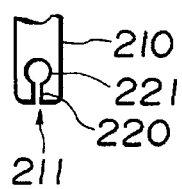

The indentation 224 of the connecting member 223 is pushed against the connecting piece 210 in the direction of the arrow shown in FIG. 51(a). Then, the small-diameter portion 220 of the slot 211 is expanded and the indentation 224 of the connecting member 223 is engaged with the large-diameter portion 221. After the engagement, the connecting member is not loose until the small-diameter portion 220 is expanded. Because the protrusion 222 of the connecting member 223 is larger than the large-diameter portion 221, the connecting member 223 does not slide along the axis and is fixed to the erecting knob 209 while maintaining a constant position.

Because a plurality of the indentations 224 are provided, even if the insertion length of the cover-type endoscope 4 or the insertion section covering portion 18 is different, it is possible to connect the erecting wire 55 to the erecting knob 209 at an appropriate position (with an appropriate length) like the third embodiment.

According to the present embodiment, it is possible to eliminate the dispersion of the insertion length of the cover-type endoscope 4 or the insertion section covering portion 18 and connect the erecting wire 55 to the erecting knob 209. Further, because no connecting wire 201 is provided, the construction of the operating unit 13 of the cover-type endoscope 4 can be simplified.

Figure 52A:
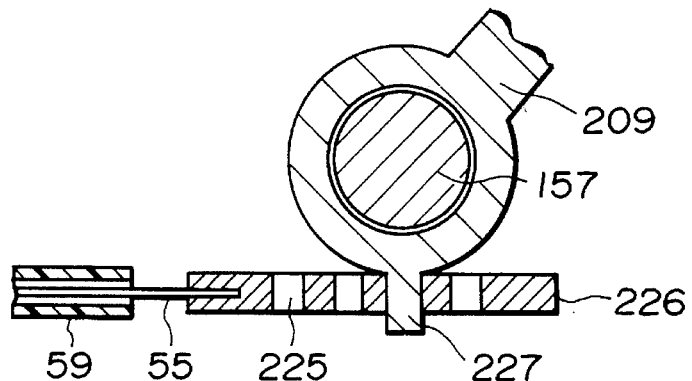
FIGS. 52(a) and 52(b) are drawings showing the construction of the connecting portion according to a modified example of the ninth embodiment.
Figure 52B:
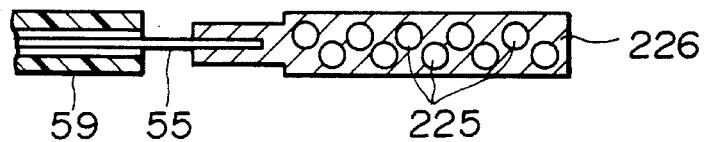

FIG. 52 is a sectional view showing an adjusting means related to the modified example of the nineteenth embodiment.

The description of the same construction and operation as the nineteenth embodiment is omitted while the same reference numerals are attached and thus only different points will be described below.

As shown in FIG. 52(a), the present modified example contains a connecting member 226 in which a plurality of holes 225 are disposed along the axis of the connecting member 226 instead of the connecting member 223 of the nineteenth embodiment. As shown in FIG. 52(a), the connecting piece 227 which protrudes from the erecting knob is engaged with the holes 225 of the connecting member 226. The construction, the operation and the effect of the present embodiment are the same as the nineteenth embodiment and thus the description of them is omitted.

Next, the 20th embodiment of the present invention will be described with reference to FIG. 53.

Instead of the adjusting means by engagement according to the nineteenth embodiment, the present embodiment includes an adjusting means by threaded engagement. The description of the same construction and operation as the nineteenth embodiment is omitted while the same reference numerals are attached.

According to the present embodiment, a circumferential threaded portion having protrusions and indentations are formed on a part of the erecting knob 235. On the other hand, the connecting member 237 fitted to the end of the erecting wire 55 includes a side threaded portion 238 which has a pitch corresponding to the protrusion/indentation pitch of the circumferential threaded portion 236.

A guiding member 239 which guides the connecting member 237 is provided on a part of the operating unit 13 and the distance between the guiding member 239 and the erecting knob 235 is determined so that the circumferential threaded portion 236 is mesh with the side threaded portion 238 when the connecting member 237 is moved along the guiding member 239 and placed below the erecting knob 235.

The distance between the circumferential surface 240 of the erecting knob 235 except the circumferential threaded portion 236 and the guiding member 239 is relatively larger than the width (height) of the connecting member 237.

The rotation range of the erecting knob 235 is restricted by protrusions 292 provided on the operating unit 13.

Next, the operation of the present embodiment will be described below.

Figure 53A:
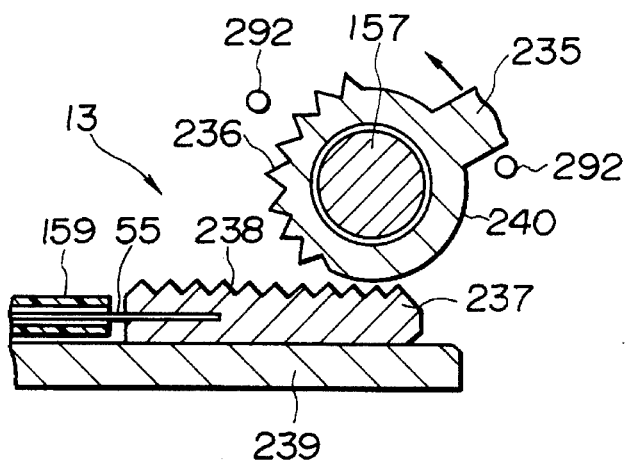
FIGS. 53(a) and 53(b) are sectional views showing the construction of the connecting portion according to the 20th embodiment.

If the erecting knob 235 is turned down as shown in FIG. 53(a), the circumferential surface 240 having no circumferential threaded portion 236 faces the guiding member 239. With this condition, the insertion section covering portion 18 is inserted into the cover-type endoscope 4.

If the connecting member 237 is placed along the guiding member 239, after the insertion section covering portion 18 is mounted on the cover-type endoscope 4, the circumferential threaded portion 238 of the connecting member 237 slidably faces the circumferential surface 240. Although, at this time, the connecting member 237 is located at such a position in which the medical treatment instrument erecting base 46 situated at the front end of the erecting wire 55 is placed down, the position of the connecting member 237 differs slightly depending on the dispersion of the insertion length of the cover-type endoscope or the insertion section covering portion 18.

When the endoscope insertion section (with the cover) is inserted into the human body, the insertion section may be sometimes bent along the shape of the body cavity. Then, in FIG. 53(a), the connecting member 237 slides slightly back or forth depending on the bending shape of the erecting wire 55 in a portion where the insertion section is inserted. However, regardless of how the insertion section is inserted, as shown in FIG. 53(a), any position of the circumferential threaded portion 238 of the connecting member 237 is located below the circumferential surface 240 of the erecting knob 235. Therefore, if the erecting knob 235 is turned to the erection side (direction of an arrow in FIG. 53(a)) as shown in FIG. 53(a), the circumferential threaded portion 236 is mesh with the side threaded portion 238, so that the connecting member 237 can be pushed or pulled depending on the rotation angle of the erecting knob 235.

That is, if the insertion length of the insertion section covering portion 18 or the cover-type endoscope 4 varies or the erecting wire is moved due to changes of the shape of a portion where the insertion section is inserted, it is possible to always maintain the erecting knob 235 down position, the operating position which erects the medical treatment instrument most and the amount of the stroke so that they are constant.

Figure 54:
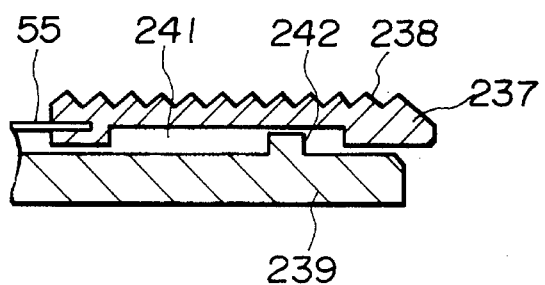
FIG. 54 is a sectional view showing the major parts related to the modified example of the 20th embodiment.

As the modified example shown in FIG. 54, it is permissible to construct the connecting member so that the maximum travel amount is restricted by providing a long indentation in the connecting member 237 and providing a protrusion 242 on the guiding member 239. In this case, the guiding member 239 can move up/down and outwardly/inwardly in these drawings.

Figure 53B:
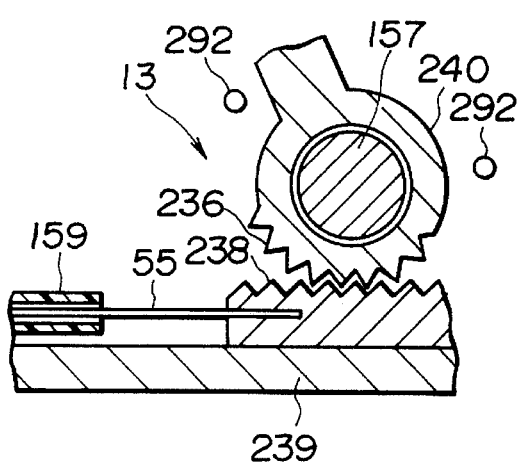

With the construction shown in FIG. 53 also, it is permissible to restrict the possible rotation range of the erecting knob 235 (for example, the operating unit is provided with a stopper or the like: not shown).

According to the present embodiment, in addition to the effect of the nineteenth embodiment, it is possible to always maintain the placing-down/erection control position and the amount of stroke even if the shape of the insertion section of the insertion section covering portion 18 is changed.

Figure 55A:
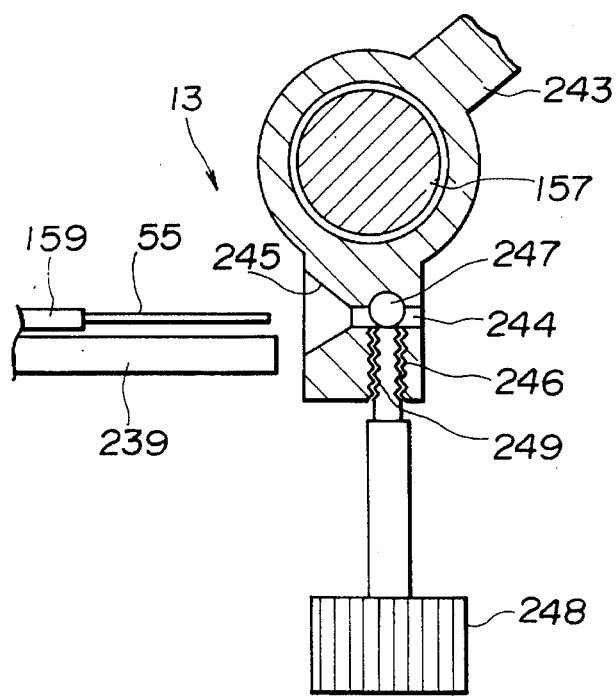
FIGS. 55(a) and 55(b) are sectional views showing the construction around the connecting portion according to the 21st embodiment.

Next, the 21st embodiment of the present invention will be described with reference to FIGS. 55(a), (b).

The erecting knob 243 has an introducing hole 244 through which the erecting wire 55 passes and the front end has a tapered opening. A female thread portion 246 is provided so as to communicate with a part of the introducing hole 244 and an indented portion 247 is provided on an extending line of the female thread portion 246 (in FIG. 55, the indented portion 247 is made in the introducing hole 244 by making a hole vertical to the axis of the female thread portion 246).

A male thread portion which corresponds to the female thread portion 246 is provided at the end of a connecting knob 248. A guiding member 239 is provided on the operating unit 13 so as to lead the erecting wire 55 which comes out of the wire tube 159 to the center of the opening 245 in the erecting knob 243. As regards the guiding member 239, it is permissible to dispose two pieces parallel to each other so as to interpose the wire tube 159 therebetween.

Next, the operation of the present embodiment will be described.

Figure 55B:
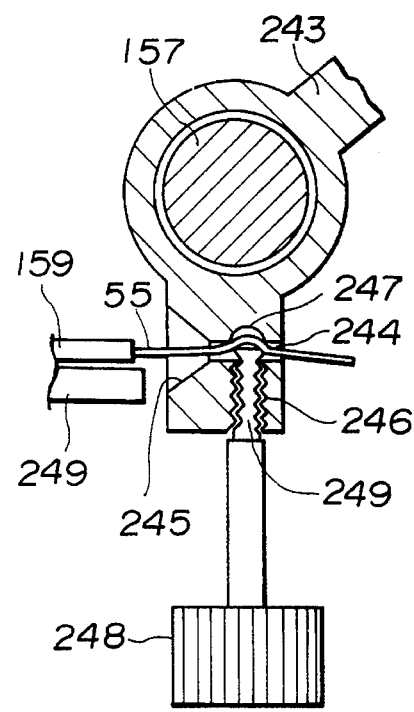

When the insertion section covering portion 18 is mounted on the cover-type endoscope 4, the ends of the wire tube 159 and the erecting wire 55 which extend from the mouth portion 33 of the insertion section covering portion 18 are introduced into the opening 245 of the erecting knob 245 along the guiding member 239. As shown in FIG. 55(b), the end of the erecting wire 55 runs through the introducing hole 244 in the erecting knob 243. At this time, the erecting wire 55 is located at such a position where the medical treatment instrument erecting base 46 provided at the end of the wire is placed down. If the connecting knob is tightened firmly, the male thread portion 249 pushes up a part of the erecting wire 55 into the indented portion 247 and fastens it.

According to the present embodiment, the cover can be produced at low cost because nothing is provided at the end of the erecting wire 55. The operation of the present embodiment is the same as the nineteenth embodiment.

Figure 56:
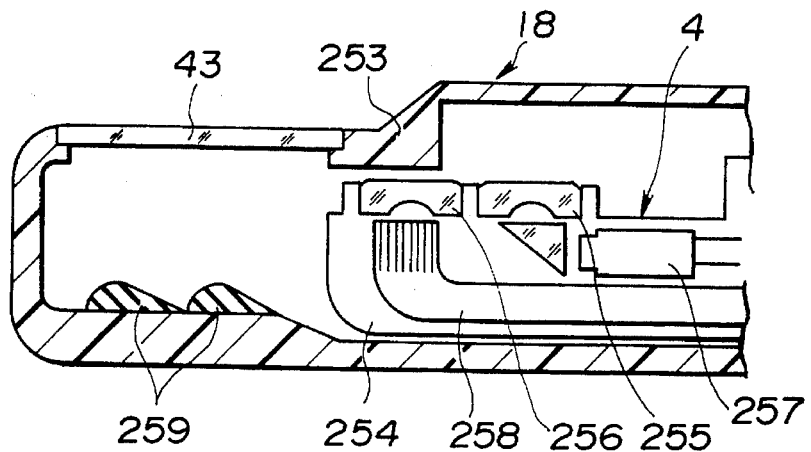
FIGS. 56 and 57 are related to the 22nd embodiment.
Figure 57:
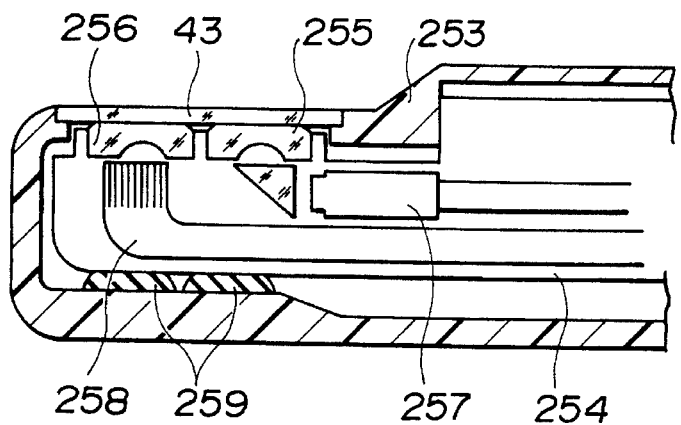

FIGS. 56 and 57 are related to the 22nd embodiment of the present invention. FIG. 56 is a longitudinal sectional view showing the construction of the front end part of the insertion section covering portion and FIG. 57 is a longitudinal sectional view showing the condition in which the insertion section covering portion is fit to the endoscope.

FIG. 56 shows the condition of the front end in which the insertion section covering portion is mounted on the cover-type endoscope. Different from the sectional view shown in FIG. 12, FIG. 56 is a longitudinal sectional view including the cover glass 43.

The insertion section covering portion 18 shown in FIG. 57 contains a front end cover component 253 instead of the front end cover component 31. The cover-type endoscope 4 shown in FIG. 57 contains a side view type front end component 254. The description of the same construction and operation as the second embodiment is omitted while the same reference numerals are attached and only different points will be explained.

As shown in FIG. 56, an observational lens 255 and an illumination lens 256 are disposed on the side of the endoscope front end component 254. Inside the endoscope front end component 254, an image pickup element 257 and an emission end of a light guide 258 are disposed at the positions which face the observational lens 255 and the illumination lens 256. The outside surfaces of the observational lens 255 and the illumination lens 256 are substantially flush with the side surface of the endoscope front end component 254.

In the endoscope front end component 254, the outside front opposite to the side in which the lenses 255, 256 are disposed is chamfered.

The light guide 258 transmits illumination light which is introduced through the insertion section 12 and supplied from the light source unit 7 and irradiates the illumination light through the illumination lens 256 to the side. The image pickup element 257 forms images of an object by receiving reflections of the illumination light through the observational lens 255.

On the other hand, within the front end cover component 253 of the insertion section covering portion 18, two urging members 259 which are composed of an elastic material such as elastomer containing rubber or the like are disposed on an inside wall which faces the transparent cover glass 43. The urging members 259 are arranged along the axis and formed so that the surfaces of the urging members slant from the beginning side to the front end side, and the tops of the slanting surfaces are formed in a spherical shape.

In the cover-type endoscope having the construction described above, if the cover-type endoscope 4 is mounted on the insertion section covering portion 18 as shown in FIG. 57, the surface which faces the side in which the observational lens 255 and the illumination lens 256 of the endoscope front end component 254 inserted into the front end cover component 253 are disposed presses the urging member 259 which acts as an urging means. The endoscope front end component 254 is urged by a repulsion of the urging member 259 toward the cover glass 43. Thus, the observational lens 255 and the illumination lens 256 are fit to the cover glass 43, thereby preventing a flaring reflection caused by the entering of the illumination light into the observational lens.

Although this example includes two pieces of the urging members 259 as shown in FIG. 57, the number of the urging members is not restricted to two pieces and even if one or three or more pieces of the urging members 259 are provided, the same effect can be obtained.

Figure 58:
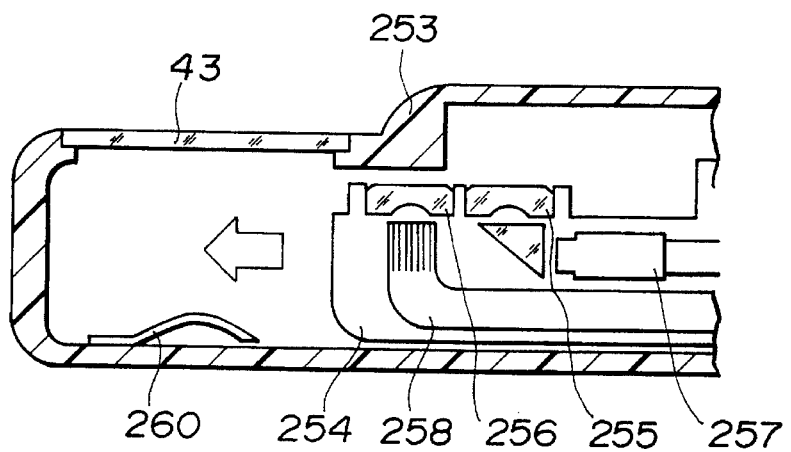
FIG. 58 is a sectional view showing the construction of the front end of the insertion section covering portion related to the 23rd embodiment.

Next, the 23rd embodiment will be described below. FIG. 58 is a sectional view showing the construction of the front end of an insertion section covering portion related to the 23rd embodiment. The construction of the 23rd embodiment is almost the same as that of the 22nd embodiment except the urging means.

As shown in FIG. 58, the 23rd embodiment includes a leaf spring 260 as the urging means instead of the urging member which is composed of an elastic material according to the 22nd embodiment. The other construction and the operation and the effect by this leaf spring are the same as those of the 22nd embodiment.

Figure 59:
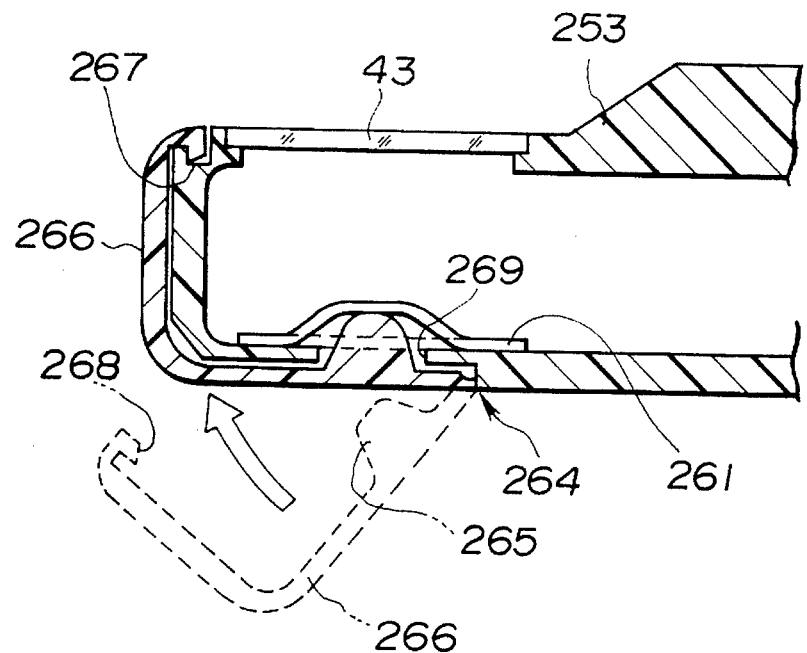
FIG. 59 is a sectional view showing the construction of the front end of the insertion section covering portion related to the 24th embodiment.

Next, the 24th embodiment will be described. FIG. 59 is a sectional view showing the construction of the front end of an insertion section covering portion related to the 24th embodiment. The 24th embodiment is the same as the 22nd embodiment except that the 22nd embodiment employs an elastic member as the urging means.

As shown in FIG. 59, according to the 24th embodiment, at the end of the front end cover component 253, an arm portion 266 is integratedly formed in the front end cover component 253 so that the arm 266 is movable via a hinge section 264. The arm 266 has a protrusion 265 which constitutes an urging means inside and is formed in the shape of the letter L, acting as a part of the front end cover component 253.

At the end of the arm 266, a locking pawl 268 which locks in a locking groove 267 provided at the end of the front end cover component 253 is provided.

Additionally, in the front end cover component 253, a hole section 269 through which the protrusion 265 passes is provided. On the inside face of the front end cover component 253, a waterproof sheet 261 which is composed of a material having waterproof and elastic properties such as a rubber sheet is provided so that the sheet covers the hole section 269. The waterproof sheet 261 seals water-tightly the ends of the inside surface of the hole section 269 as shown by a dashed line. Thus, dirt outside the cover-system endoscope never adhere to the cover-type endoscope by means of the waterproof sheet 261. The other construction is the same as that of the 22nd embodiment.

In the cover-system endoscope of the 24th embodiment having the construction described above, after the endoscope front end component 254 (not shown) is inserted into the front end cover component 253, by turning the arm 266 with respect to the hinge section 264, the locking pawl 268 is locked in the locking groove 267. Consequently, the protrusion 265 presses the hole section 269 and pushes up the endoscope front end component so that the observational lens 255 and the illumination lens 256 are fit to the cover glass 43. The other operation and the effect are the same as the 22nd embodiment.

Figure 60:
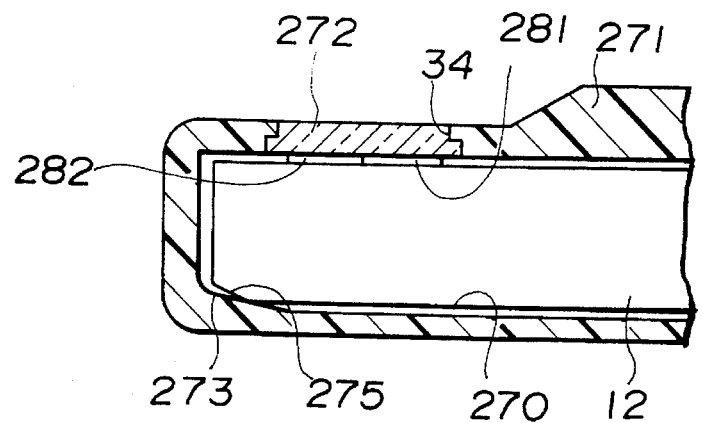
FIG. 60 is related to the 25th embodiment of the present invention and a sectional view taken along the axis of the insertion section showing the construction of the front end when the endoscope insertion section is inserted into the endoscope cover assembly.

FIG. 60 is related to the 25th embodiment of the present invention and a sectional view taken along the axis showing the construction of the front end when the endoscope insertion section is inserted into the endoscope cover assembly.

The present embodiment provides another construction concerning the urging means for the optical systems of the cover and the endoscope. In this embodiment, the front ends of the insertion section covering portion 18 and the cover-type endoscope 4 are different from those of the 22nd embodiment. The other construction and operation of the present embodiment are the same as the 22nd embodiment and thus the description of them is omitted while the same reference numerals are attached. Only different points will be described.

According to the 25th embodiment, within the insertion section covering portion 18, an endoscope inserting channel 270 for inserting the insertion section of the cover-type endoscope 4 is provided. Within the front end cover component 31, the endoscope inserting channel 270 is formed. The endoscope inserting channel 270 is formed up to the front end cover component 271 within the insertion section covering portion 18. On the side of the front end cover component 271, an observational opening 34 is provided and a lens cover 272 is disposed in the observational opening 34. The lens cover 272 is formed of transparent flexible elastomer.

On the side of the front end of the endoscope insertion section 12, an objective lens 281 and an illumination lens 282 are disposed. When the endoscope insertion section 12 is inserted into the endoscope inserting channel 270 of the insertion section covering portion 18, the objective lens 281 and the illumination lens 282 are positioned so that they face the lens cover 272. The objective lens 281 and the illumination lens 282 are disposed so that they slightly protrude from the circumference of the endoscope insertion section 12 and in particular, the illumination lens 282 is disposed so as to protrude a little more than the objective lens 281, so that the objective lens 281 and the illumination lens 282 can contact the lens cover 272 of the front end cover component 271 easily.

Within the front end cover component 271, at the end of the endoscope inserting channel 270, a guide slope portion 273 which is an urging means constructed of a slope rising toward the front end is provided.

On the other hand, at the end of the endoscope insertion section 12 to be inserted into the endoscope inserting channel 270, a guide contacting portion 275 constructed of a chamfered portion which contacts the guide slope portion and slides along the slope is provided.

When the endoscope insertion section 274 is inserted consecutively into the endoscope inserting channel 270 in the insertion section covering portion 18, the guide contacting portion 275 at the end of the endoscope insertion section 274 contacts the guide slope portion 273 at the end of endoscope inserting channel 270 and then the endoscope insertion section 274 is inserted along the guide slope portion while the section 274 is pushed to the lens cover 272. Consequently, the objective lens 281 and the illumination lens 282 are fit to the lens cover 272, thereby preventing halation. Additionally, in the present embodiment also, the hard members of the front ends of the cover and the endoscope are not longer or larger in diameter as compared with other embodiments and thus it is possible to prevent an occurrence of an insertion trouble.

In this invention, it is evident that different embodiments can be configured in a wide range on the basis of the spirit of the invention. This invention is not restricted by specific embodiments except that it is restricted by the accompanying claims.

What is claimed is:

1. An endoscope cover assembly for covering at least the insertion section of the main body of an endoscope containing an insertion section and an operating unit, the endoscope cover assembly having a medical treatment instrument channel through which a medical treatment instrument is to be inserted and further having a direction changing means for changing the direction of the protrusion of said medical treatment instrument introduced through said medical treatment instrument channel from an opening of said medical treatment instrument channel.

2. A cover-system endoscope comprising the main body of an endoscope having an insertion section and an operating unit; and an endoscope cover assembly for covering at least said insertion section of said main body of the endoscope, said endoscope cover assembly having a medical treatment instrument channel through which a medical treatment instrument is to be inserted, said endoscope cover assembly containing a direction changing means for changing the direction of the protrusion of said medical treatment instrument introduced through said medical treatment instrument channel from an opening of said medical treatment instrument channel.

3. A cover-system endoscope according to claim 2 wherein said direction changing means is disposed near the opening of said medical treatment instrument channel and the end portion of the side of said medical treatment instrument channel is an erecting base which is rotatably held.

4. A cover-system endoscope according to claim 2 comprising a driving means for operating said direction changing means in order to change the direction of the protrusion of said medical treatment instrument; and a transmitting means for transmitting the driving force of said driving means to said direction changing means.

5. A cover-system endoscope according to claim 4 wherein said transmitting means is connected to said driving means and which includes an adjusting means constructed so as to be capable of adjusting the connecting position.

6. A cover-system endoscope according to claim 5 wherein said adjusting means is constructed so as to be capable of adjusting the length of said transmitting means when said transmitting means is connected to said driving means.

7. A cover-system endoscope according to claim 6 wherein said driving means is an erection operating member which operates said direction changing means in order to change the direction of the protrusion of said medical treatment instrument; said transmitting means is an erecting wire which transmits the driving force for said erection control member to said direction changing means; and further said adjusting means comprises a plurality of first locking portions which are disposed on either said erecting wire or said erection control member and second locking portion which is engaged with any one of said plurality of first locking portions provided on either said erection control member or said erecting wire in which said first locking portions are not provided.

8. A cover-system endoscope according to claim 1 wherein said first locking portions contain a plurality of protrusions which are disposed at interval on said erecting wire; and said second locking portion is disposed on said erection control member and locks in between protrusions of said locking portion, said second locking portion consisting of a hole having a smaller diameter than said protrusion and a slot located in a continuous state with this hole.

9. A cover-system endoscope according to claim 8 wherein the protrusion of said first locking portion is formed in a spherical shape.

10. A cover-system endoscope according to claim 1 wherein said first locking portion comprises a connecting member which is connected to said erecting wire and contains a plurality of holes; and said second locking portion is a protrusion which is disposed on said erection control member, locking in any one of said plurality of holes provided on said first locking portion.

11. A cover-system endoscope according to claim 6 wherein said driving means is an erection control member which operates said direction changing means in order to change the direction of the protrusion of said medical treatment instrument; said transmitting means is an erecting wire which transmits the driving force for said erection control member to said direction changing means; and said adjusting means comprises a rack which is connected to said erecting wire and a threaded portion which is formed on said erection control member and meshes with said rack in order to adjust the length of said transmitting means by changing the position in which said rack meshes with said threaded portion.

12. A cover-system endoscope according to claim 6 wherein at least part of the circumference of said erection control member is circular and said threaded portion is formed on part of the circumference of the circle.

* * * * *